United States Patent
Boström et al.

(10) Patent No.: US 7,582,629 B2
(45) Date of Patent: Sep. 1, 2009

(54) DERIVATIVES OF ISOTHIAZOL-3(2H)-ONE 1,1-DIOXIDES AS LIVER X RECEPTOR MODULATORS

(75) Inventors: Jonas Boström, Mölndal (SE); Kay Brickmann, Mölndal (SE); Anders Broo, Mölndal (SE); Robert Judkins, Mölndal (SE); Lanna Li, Mölndal (SE); Pernilla Sandberg, Mölndal (SE); Marianne Swanson, Mölndal (SE); Christer Westerlund, Mölndal (SE); Patrik Holm, Pargas (FI)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 11/813,481

(22) PCT Filed: Jan. 9, 2006

(86) PCT No.: PCT/SE2006/000026

§ 371 (c)(1),
(2), (4) Date: Jan. 21, 2008

(87) PCT Pub. No.: WO2006/073363

PCT Pub. Date: Jul. 13, 2006

(65) Prior Publication Data

US 2008/0255122 A1  Oct. 16, 2008

(30) Foreign Application Priority Data

Jan. 10, 2005 (SE) ................. 0500053
Jul. 8, 2005 (SE) ................. 0501628

(51) Int. Cl.
*A61K 31/535* (2006.01)
*A61K 31/445* (2006.01)
*A61K 31/425* (2006.01)
*C07D 415/00* (2006.01)
*C07D 413/00* (2006.01)
*C07D 417/00* (2006.01)
*C07D 275/02* (2006.01)

(52) U.S. Cl. ........... 514/236.8; 514/326; 514/372; 544/133; 546/209; 548/213; 548/214

(58) Field of Classification Search ........... 514/236.8, 514/326, 372; 544/133; 546/209; 548/213, 548/214
See application file for complete search history.

(56) References Cited

U.S. PATENT DOCUMENTS

2003/0195238 A1  10/2003  Gil et al.
2009/0005353 A1*  1/2009  Broo et al. ............... 514/210.2

FOREIGN PATENT DOCUMENTS

| | | |
|---|---|---|
| EP | 1069110 | 1/2001 |
| JP | 2001163786 | 6/2001 |
| WO | 9708143 | 3/1997 |
| WO | 0021927 | 4/2000 |
| WO | 0054759 | 9/2000 |
| WO | 0103705 | 1/2001 |
| WO | 0174771 | 10/2001 |
| WO | 0246183 | 6/2002 |
| WO | 03031440 | 4/2003 |
| WO | 2004111022 | 12/2004 |
| WO | 2005005416 | 1/2005 |
| WO | 2005005417 | 1/2005 |
| WO | 2005035551 | 4/2005 |

OTHER PUBLICATIONS

Laffitte et al., "Activation of liver X receptor improves glucose tolerance through coordinate regulation of glucose metabolism in liver and adipose tissue," PNAS (2003) 100(9):5419-5424.
Notice of Co-Pending Applications: U.S. Appl. No. 11/813,489; U.S. Appl. No. 11/813,467; U.S. Appl. No. 11/813,458 and U.S. Appl. No. 11/813,470.
Office Action dated Dec. 22, 2008 received in copending U.S. Appl. No. 11/813,489.
Patani, George, A. Bioisosterism: A rational approach in drug design. Chem. Rev. 96 (1996) 3147-3176.
"Atherosclerosis." Retrieved online via Internet [Dec. 13, 2008] http://www.nlm.nih.gov/medlineplus/ency/article/000171.htm.
Office Action dated Dec. 22, 2008 received in copending U.S. Appl. No. 11/813,458.
Non-final Office Action dated Jun. 2, 2009 received in copending U.S. Appl. No. 11/813,470.

* cited by examiner

*Primary Examiner*—Kamal A Saeed
*Assistant Examiner*—Samantha L Shterengarts
(74) *Attorney, Agent, or Firm*—Pepper Hamilton LLP

(57) ABSTRACT

The present invention relates to certain novel compounds of the formula (I) to processes for preparing such compounds, to their the utility in modulation of nuclear hormone receptors Liver X Receptor (LXR) α (NR1H3) and/or β (NR1H2) and in treating and/or preventing clinical conditions including cardiovascular diseases such as atherosclerosis; inflammatory diseases, Alzheimer's disease, lipid disorders (dyslipidemias) whether or not associated with insulin resistance, type 2 diabetes and other manifestations of the metabolic syndrome, to methods for their therapeutic use and to pharmaceutical compositions containing them.

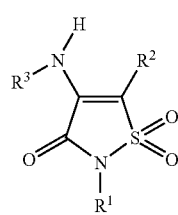

(I)

26 Claims, No Drawings

SEQUENCE LISTING

<160> NUMBER OF SEQ ID NOS: 15

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence:
    ABCA1 Forward Primer

<400> SEQUENCE: 1
aagggtttct ttgctcagat tgtc                                          24

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence:
    ABCA1 Reverse Primer

<400> SEQUENCE: 2
tgccaaaggg tggcaca                                                  17

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: ABCA1 Probe

<400> SEQUENCE: 3

-continued

```
ccagctgtct ttgtttgcat tgccc                                            25

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:
      ABCG1 Forward Primer

<400> SEQUENCE: 4
ccatgaatgc cagcagctac t                                                21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:
      ABCG1 Reverse Primer

<400> SEQUENCE: 5
cactgacacg cacacggact                                                  20

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: ABCG1 Probe

<400> SEQUENCE: 6
tgccgcaatg acggagccc                                                   19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:
      FAS Forward Primer

<400> SEQUENCE: 7
ggcatcattg ggcactcctt                                                  20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:
      FAS Reverse Primer

<400> SEQUENCE: 8
gctgcaagca cagcctctct                                                  20

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: FAS Probe

<400> SEQUENCE: 9
ccatctgcat agccacaggc aacctc                                           26
```

-continued

```
<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:
      SREBP1c Forward Primer

<400> SEQUENCE: 10
ggagccatgg attgcacatt                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:
      SREBP1c Reverse Primer

<400> SEQUENCE: 11
cctgtctcac ccccagcata                                              20

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence:
      SREBP1c Probe

<400> SEQUENCE: 12
cagctcatca acaaccaaga cagtgacttc c                                 31

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:
      36B4 Forward Primer

<400> SEQUENCE: 13
gaggaatcag atgaggatat ggga                                         24

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:
      36B4 Reverse Primer

<400> SEQUENCE: 14
aagcaggctg acttggttgc                                              20

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: 36B4 Probe

<400> SEQUENCE: 15
tcggtctctc gactaatccc gccaa                                        25
```

DERIVATIVES OF ISOTHIAZOL-3(2H)-ONE 1,1-DIOXIDES AS LIVER X RECEPTOR MODULATORS

CROSS-REFERENCE TO RELATED APPLICATIONS

This application is the U.S. National Stage filing of International Application Serial No. PCT/SE2006/000026 filed Jan. 9, 2006, which claims priority to Swedish Application No. 0501628-2 filed Jul. 8, 2005, and to Swedish Application No. 0500053-4 filed Jan. 10, 2005, each of which is incorporated herein by reference in its entirety.

FIELD OF THE INVENTION

The present invention relates to certain novel substituted 4-(arylamino or heteroarylamino)isothiazol-3(2H)-one 1,1-dioxides, to processes for preparing such compounds, to their the utility in modulation of nuclear hormone receptors Liver X Receptor (LXR) α (NR1H3) and/or β (NR1H2) and in treating and/or preventing clinical conditions including cardiovascular diseases such as atherosclerosis; inflammatory diseases, Alzheimer's disease, lipid disorders (dyslipidemias) whether or not associated with insulin resistance, type 2 diabetes and other manifestations of the metabolic syndrome, to methods for their therapeutic use and to pharmaceutical compositions containing them.

BACKGROUND OF THE INVENTION

Abnormalities of cholesterol and fatty acid homeostasis, that are reflected as diverse dyslipidemias, are causal of atherosclerosis and consequently cardiovascular disease (CVD). This disease is one of the major health problems in industrialized countries and is reaching the same prevalence in adults in developing nations. Most studies show that statins reduce low density lipoproteins (LDL) cholesterol by 25-30% and the relative risk of coronary events by approximately 30%. While this beneficial effect is significant, effectively 70% of the treated cohort remains with unchanged risk. This has prompted intense research in order to identify other common abnormalities of lipid metabolism that if efficiently treated could improve the results of current CVD therapy.

The nuclear hormone receptors LXR α and β use oxysterols as natural ligands. They appear to act as cholesterol sensors with target genes that are required for cholesterol efflux from macrophages, like ATP binding cassette transporter A1 (ABCA1) and apoE, as well as gene products, like cholesterol ester transferase protein (CETP) and phospholipid transport protein (PLTP), that are required for the function of high density lipoprotein (HDL) in the reverse cholesterol transport. In the liver, LXR ligands seem to stimulate the hepatobiliary secretion of cholesterol, a pathway controlled by the ABCG5 and ABCG8. The same cholesterol transporters appear to reduce cholesterol absorption in enterocytes, therefore influencing total body cholesterol balance. These effects of LXR stimulation could help to explain its remarkable anti-atherosclerotic properties observed in animal models.

Recently the synthetic LXR ligands GW3965 (Glaxo) and T-0901317 (Tularik) were reported to increase glucose tolerance in fat fed obese mouse, which was interpreted to result from reduced hepatic gluconeogenesis and increased glucose uptake in adipocytes (Lafitte B A et al. Proc Natl Acad Sci U S A. 2003 Apr. 29; 100(9):5419-24). Activation of LXR's improves glucose tolerance through coordinated regulation of glucose metabolism in liver and adipose tissue.

JP2001163786A discloses the synthesis of certain novel 2-(substituted alkyl)-4-(substituent)-5-(substituent)isothiazol-3(2H)-one 1,1-dioxides wherein the 4- or 5-positions are substituted by e.g. H, lower alkyl or carboxyl. These compounds are reported to have matrixmetalloproteinase (MMP) inhibitory activity (especially matrixmetalloproteinase-13 (MMP-13) inhibitory activity) and aggrecanase inhibitory activity, and are useful in the prevention or treatment of arthritis (especially osteoarthritis) and for inhibiting metastasis, infiltration or proliferation of cancer (especially breast cancer).

EP1069110A1 discloses the synthesis of certain novel 2-(substituted alkyl)-4-(substituent)-5-(substituent)isothiazol-3(2H)-one 1,1-dioxides wherein the 4- or 5-positions are substituted by e.g. H, lower alkyl or carboxyl. These compounds are reported to have matrixmetalloproteinase-13 (MMP-13) inhibitory activity and aglycanase inhibitory activity, and are useful for treating arthritic disorders such as reumatoid arthritis.

WO9708143A1 discloses the synthesis of 2-(substituted alkyl)-4-(substituent)-5-(substituent)isothiazol-3(2H)-one 1,1-dioxides wherein the substituents in 4- or 5-positions are selectioned from nitro, cyano, trifluoromethyl, carbethoxy, carbomethoxy, carbopropoxy, acetyl, carbamoyl, carbamoyl substituted with an alkyl of 1 to 3 carbon atoms, acetoxy, carboxy, hydroxy, amino, amino substituted with an alkyl of 1 to 3 carbon atoms, alkyl of 1 to 4 carbon atoms, alkoxy of 1 to 4 carbon atoms or halo, or the 4 and/or 5 positions are unsubstituted, and their use for reducing levels of Tumor Necrosis Factor (TNF) in mammals.

In the application WO05/005417 it is disclosed that certain novel 1-(substituted alkyl)-3 amino-4 phenyl-1H-pyrrole-2,5-dione derivatives have utility in the modulation of nuclear hormone receptors Liver X Receptor (LXR) α (NR1H3) and/or β (NR1H2) and in treating and/or preventing clinical conditions including cardiovascular diseases.

In the application WO05/005416 it is disclosed that certain novel 5-thioxo-1,5-dihydro-2H-pyrrol-2-one and 1H-pyrrole-2,5-dithione derivatives have utility in the modulation of nuclear hormone receptors Liver X Receptor (LXR) α (NR1H3) and/or β (NR1H2) and in treating and/or preventing clinical conditions including cardiovascular diseases.

WO05/035551 discloses certain novel 2-(substituent)-4-(substituent)-5-(substituent)isothiazol-3(2H)-one 1,1-dioxides. These compounds are reported to modulate the activity of a target protein such as a phosphatase.

The term "LXR modulator" as used herein, refers to the ability of a compound to modulate the biological activity of LXRα and/or LXRβ via increase or decrease of the function and/or expression of LXRα and/or LXRβ, where LXRα and/or LXRβ function may include transcription regulatory activity and/or protein-binding. Modulation may occur in vitro or in vivo. Modulation, as described herein, includes antagonism, agonism, partial antagonism and/or partial agonism of a function or characteristic associated with LXRα and/or LXRβ, either directly or indirectly, and/or the upregulation or downregulation of LXRα and/or LXRβ expression, either directly or indirectly. More specifically, such an LXR modulator either enhances or inhibits the biological activities of LXR via the function and/or expression of LXR. If such a modulator partially or completely enhances the biological activities of LXR via the function and/or expression of LXR, it is a partial or full LXR agonist, respectively. It is the object of the present invention to provide LXR modulators. Another object of this invention is to provide LXR modulator compounds being LXR agonists.

It should be noted that to show activity in the specific Test Methods described herein, the LXR modulator compound must bind to the ligand binding domain of the LXR and recruit either the specific peptide derived from the co-activator protein, SRC1, to the modulator compound-bound LXR complex in the described Co-activator recruitment assay, or one or more of the nuclear hormone receptor co-factors present in the U2OS cell-based method described herein. The compounds of this invention that form an LXR-modulator compound-complex may recruit at least one or more of the other >80 known different nuclear hormone receptor cofactors in any other cell-based method prepared and assayed according to known procedures. Compounds according to Formula I, that do not recruit the SRC1-derived peptide or any of the co-factors present in the in cell-based method described herein, is however anticipated to bind to LXR and the LXR-modulator compound-complex so formed will recruit at least one or more of the other >80 known different nuclear receptor cofactors present in other cellular system. The LXR modulator compound-complex may also displace co-repressors, such as NcOR, with simultaneous recruitment of a co-activator or may only displace a co-repressor without co-activator recruitment, leading to partial activation of certain LXR regulated genes. Recruiter peptides derived from any of these other nuclear hormone receptor cofactors may be similarly prepared and assayed according to known procedures.

DESCRIPTION OF THE INVENTION

According to a first aspect of the invention there is provided a compound of formula I:

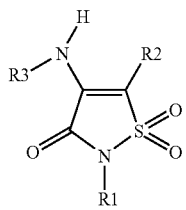

formula I or a pharmaceutically acceptable salt or solvate thereof, or a solvate of such a salt, wherein $R^1$ represents X which is optionally substituted by one or more of the following: F, OH, CN, $NR^aR^a$, $OR^b$, $SR^b$, $S(O)R^b$, $SO_2R^bC(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$ or $NR^aC(O)NR^aR^a$;

cycloalkyl or heterocyclyl each optionally substituted by one or more of the following: F, OH, CN, $NR^aR^a$, $OR^b$, $SR^b$, $S(O)R^b$, $SO_2R^bC(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$ or $NR^aC(O)NR^aR^a$;

phenyl or heteroaryl each optionally substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$ or $NR^aC(O)NR^aR^a$;

cycloalkylY or heterocyclylY wherein cycloalkyl or heterocyclyl each optionally is substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$ or $NR^aC(O)NR^aR^a$;

phenylY or heteroarylY wherein phenyl or heteroaryl each optionally is substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^cC(O)R^b$, $C(O)OR^a$, $OC(O)R^b$, $SO_2NR^aR^a$, $NR^aSO_2R^b$, $NR^aC(O)OR^b$, $OC(O)NR^aR^a$ or $NR^aC(O)NR^aR^a$;

$R^2$ represents phenyl which is optionally substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$;

$R^3$ represents aryl or $Het^1$ wherein aryl or $Het^1$ each optionally is substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, Q, $Het^2$, R, $Het^3$, QZ, $Het^2Z$, RZ, $Het^3Z$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$;

$Het^4$ or T wherein $Het^4$ or T each optionally is substituted on the aromatic ring by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, Q, $Het^2$, R, $Het^3$, QZ, $Het^2Z$, RZ, $Het^3Z$, or $C_1$-$C_4$alkyl which is optionally substituted by one or more of the following: F, OH, CN, $NR^aR^a$, $OR^b$, $SR^b$, $S(O)R^b$, $SO_2R^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$, and wherein Het$^4$ or T each optionally is substituted on the non-aromatic ring by one or more of the following: F, OH, CN, NR$^a$R$^a$, OR$^b$, SR$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^a$, NR$^a$C(O)OR$^b$, OC(O)NR$^a$R$^a$, NR$^a$C(O)NR$^a$R$^a$, thioxo, Q, Het$^2$, R, Het$^3$, QZ, Het$^2$Z, RZ, Het$^3$Z, or C$_1$-C$_4$alkyl which is optionally substituted by one or more of the following: F, OH, CN, NR$^a$R$^a$, OR$^b$SR$^b$S(O)R$^b$SO$_2$R$^b$C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

The following definitions shall apply throughout the specification and the appended claims unless specifically stated otherwise:

The term "X" denotes a straight or branched, saturated or unsaturated alkyl group having 1 to 6 carbon atoms wherein said alkyl group may optionally be interrupted by one of the following: O, S, SiR$^b$R$^b$R$^b$, S(O), SO$_2$, C(O), NR$^a$, OC(O), C(O)O, NR$^a$C(O), C(O)NR$^a$, SO$_2$NR$^a$ or NR$^a$SO$_2$. It shall be understood that when X is present more than once in the same compound then the value may be the same or different. Examples of said "X" include, but are not limited to, methyl, ethyl, propyl, isopropyl, butyl, tert-butyl, isobutyl, pentyl, hexyl, vinyl, isopropenyl, allyl, but-2-enyl, ethynyl, 2-propynyl, 2-methoxyethyl, 3-methylpropyl, methylthiomethyl, 3-hydroxypropyl, 2-(2-methoxyethoxy)ethyl, 3-(2-methoxyethoxy)propyl, 2,2-dimethylpropyl, 2-hydroxyethyl, 2,2,2-trifluoroethyl, 2,3-dihydroxypropyl, 2-cyanoethyl and methyl ethanoylglycinate.

The term "Y" denotes a straight or branched, saturated or unsaturated alkylene group having 1 to 3 carbon atoms wherein said alkylene group binds to nitrogen in 2-position in the isothiazol-3(2H)-one 1,1-dioxide, and may optionally be interrupted or ended by one of the following: O, S, SiR$^b$R$^b$, S(O), SO$_2$, C(O), OC(O), C(O)O, NR$^c$C(O), C(O)NR$^c$, NR$^c$ and/or Y is optionally substituted by one or more of the following independently selected from: OH, F, CN, NR$^a$R$^a$, C$_1$-C$_4$alkyl, OR$^b$, SR$^b$, SiR$^b$R$^b$R$^b$, S(O)R$^b$ or SO$_2$R$^b$. In the definition of "Y" the term "ended by O, S, SiR$^b$R$^b$, S(O), SO$_2$, C(O), OC(O), C(O)O, NR$^c$C(O), C(O)NR$^c$, NR$^c$" means that the alkylene group has as the last position O, S, SiR$^b$R$^b$, S(O), SO$_2$, C(O), OC(O), C(O)O, NR$^c$C(O), C(O)NR$^c$ or NR$^c$ before it binds further to phenyl, heteroaryl, cycloalkyl or heterocyclyl. Examples of said "Y" include, but are not limited to, methylene, ethylene, propylene, 2-methylethylene, and 1-methylethylene.

The term "Z" denotes a straight or branched, saturated or unsaturated alkylene group having 1 to 6 carbon atoms wherein said alkylene group binds to aryl, Het$^1$, Het$^4$ or T and one of the following: Q, Het$^2$, R or Het$^3$, and may optionally be interrupted or ended by one of the following: O, S, SiR$^b$R$^b$, S(O), SO$_2$, C(O), OC(O), C(O)O, NR$^a$C(O), C(O)NR$^a$, NR$^a$, SO$_2$NR$^a$, NR$^a$SO$_2$, or is one of the following: O, S, SiR$^b$R$^b$, S(O), SO$_2$, C(O), OC(O), C(O)O, NR$^a$C(O), C(O)NR$^a$, NR$^a$, SO$_2$NR$^a$, NR$^a$SO$_2$ and/or Z is optionally substituted by one or more of the following independently selected from: OH, F, CN, NR$^c$R$^c$, C(O)R$^c$, OR$^b$, SR$^c$, SiR$^b$R$^b$R$^b$, S(O)R$^c$, SO$_2$R$^c$, phenyl, phenylC$_1$-C$_3$alkyl, or C$_1$-C$_4$alkyl which is optionally substituted by one or more of the following independently selected from: F, OH, NR$^a$R$^a$, SR$^b$, SiR$^b$R$^b$R$^b$, S(O)R$^b$, SO$_2$R$^b$, OR$^b$. In the definition of "Z" the term "ended by O, S, SiR$^b$R$^b$, S(O), SO$_2$, C(O), OC(O), C(O)O, NR$^a$C(O), C(O) NR$^a$, NR$^a$, SO$_2$NR$^a$, NR$^a$SO$_2$" means that the alkylene group has as the last position O, S, SiR$^b$R$^b$, S(O), SO$_2$, C(O), OC(O), C(O)O, NR$^a$C(O), C(O)NR$^a$, NR$^a$, SO$_2$NR$^a$ or NR$^a$SO$_2$ before it binds further to aryl, Het$^1$, Het$^4$, T, Q, Het$^2$, R or Het$^3$. Examples of said "Z" include, but are not limited to, methylene, ethylene, propylene, butylene, pentylene, hexylene, O, S, S(O), SO$_2$, C(O), OC(O), C(O)O, C(O)CH$_2$, CH$_2$C(O), C(O)(C$_1$-C$_4$alkyl), NHC(O), C(O)NH, NH, SO$_2$NH, NHSO$_2$, N(C$_1$-C$_4$alkyl)C(O), C(O)N(C$_1$-C$_4$alkyl), N(C$_1$-C$_4$alkyl), SO$_2$N(C$_1$-C$_4$alkyl), N(C$_1$-C$_4$alkyl)SO$_2$, 1-methylpropylene, 2-methylpropylene and 3-methylpropylene. In the definition of Z it is to be understood that specific values bind in the order written, i.e. from left to right. For example, when Z is C(O)CH$_2$ then C(O) in said C(O)CH$_2$ binds to aryl, Het$^1$, Het$^4$ or T and CH$_2$ in said C(O)CH$_2$ binds to Q, Het$^2$, R or Het$^3$.

The term "Q" denotes a saturated or unsaturated non-aromatic monocyclic ring composed of 3, 4, 5, 6, 7 or 8 carbon atoms, which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^a$, C(O)OR$^a$, OC(O)R$^b$, NR$^a$SO$_2$R$^b$, SO$_2$NR$^a$R$^a$, NR$^a$C(O)OR$^b$, OC(O) NR$^a$R$^a$ or NR$^a$C(O)NR$^a$R$^a$. Examples of said "Q" include, but are not limited to, cyclopropyl, cyclobutyl, cyclopentyl, cyclohexyl, cycloheptyl, cyclooctanyl, cyclobutenyl, cyclopentenyl, cyclohexenyl, cycloheptenyl, cyclooctenyl, cyclopentadienyl, cyclohexadienyl and cyclooctadienyl.

The term "R" denotes a phenyl group which is optionally substituted by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O) R$^b$, SO$_2$NR$^a$R$^a$, NR$^a$SO$_2$R$^b$, NR$^a$C(O)OR$^b$, OC(O)NR$^a$R$^a$, OSO$_2$R$^b$NR$^a$C(O)N$^a$R$^a$, SO$_2$NHC(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

The term "T" denotes an aromatic or partly aromatic bicarbocyclic ring system composed of 8, 9 or 10 carbon atoms. T binds to nitrogen in 4-position on the isothiazol-3(2H)-one 1,1-dioxide through the aromatic part of the bicyclic ring. Examples of said "T" include, but are not limited to, bicyclo [4,2,0]octa-1,3,5-triene, azulene, indene, indane, naphtalene, 1,2-dihydronaphtalene, 1,4-dihydronaphtalene and 1,2,3,4-tetrahydronaphtalene.

The term "C$_1$alkyl" denotes an alkyl group having 1 carbon atom. An example of said alkyl includes, but is not limited to, methyl.

The term "C$_1$-C$_3$alkyl" denotes a straight or branched, saturated or unsaturated alkyl group having 1 to 3 carbon atoms. Examples of said alkyl include, but are not limited to, methyl, ethyl, propyl, isopropyl, vinyl, isopropenyl, allyl, ethynyl, and 2-propynyl.

The term "C$_1$-C$_4$alkyl" denotes a straight or branched, saturated or unsaturated alkyl group having 1 to 4 carbon atoms. Examples of said alkyl include, but are not limited to, methyl, ethyl, propyl, isopropyl, tert-butyl, vinyl, isopropenyl, allyl, but-2-enyl, ethynyl, 2-propynyl, and but-2-ynyl.

The term "halogen" denotes fluoro, chloro, bromo and iodo groups.

The term "cycloalkyl" denotes a saturated or unsaturated non-aromatic monocyclic ring composed of 3, 4, 5, 6, 7 or 8 carbon atoms. Examples of said "cycloalkyl" include, but are not limited to, cyclopropyl, cyclobutyl, cyclopentyl, cyclohexyl, cycloheptyl, cyclooctanyl, cyclobutenyl, cyclopentenyl, cyclohexenyl, cycloheptenyl, cyclooctenyl, cyclopentadienyl, cyclohexadienyl and cyclooctadienyl.

The term "heterocyclyl" denotes a saturated or unsaturated non-aromatic 3, 4, 5, 6, 7, or 8 membered monocyclic ring in which one or more of the atoms in the ring is an element other than carbon independently selected from one or more of for example nitrogen, oxygen or sulfur. The term "sulfur" shall be understood to include sulphoxide (S(O)) and sulphone (SO$_2$). The term "nitrogen" shall be understood to include nitrogen oxide (NO). Examples of said "heterocyclyl" include, but are not limited to, aziridine, azetidine, 2-pyrroline, 3-pyrroline, pyrrolidine, imidazoline, piperidine, piperazine, 2-pyrazoline, oxirane, oxetane, tetrahydrofuran, tetrahydropyran, 1,4-dioxane, 1,3-dioxolane, 1,2-oxathiolane, morpholine, 3-pyrazoline, pyrazolidine, 2H-pyrane, 4H-pyrane, 1,4-dithiane, 1,4-oxathiane and thiomorpholine.

The term "heteroaryl" denotes an aromatic 5 or 6 membered monocyclic ring in which one or more of the atoms in the ring is an element other than carbon independently selected from one or more of for example nitrogen, oxygen and sulfur. The term "sulfur" shall be understood to include sulphoxide (S(O)) and sulphone (SO$_2$). The term "nitrogen" shall be understood to include nitrogen oxide (NO). Examples of said "heteroaryl" include, but are not limited to, furan, pyrrole, pyrazine, pyrazole, imidazole, triazole, pyrimidine, pyridazine, pyridine, pyridine-1-oxide, isoxazole, oxazole, isothiazole, thiazole, thiophene, 1,2,4-triazole, furazane, 1,2,3-oxadiazole, 1,2,4-oxadiazole, 1,2,5-oxadiazole, 1,3,4-oxadiazole, 1,2,5-thiadiazole, 1,2,4-thiadiazole and 1,2,3-thiadiazole.

The term "aryl" denotes a phenyl group which binds to nitrogen in 4-position on the isothiazol-3(2H)-one 1,1-dioxide.

The term "Het$^1$" denotes an aromatic 5 or 6 membered monocyclic ring in which one or more of the atoms in the ring is an element other than carbon independently selected from one or more of, for example nitrogen, oxygen and sulfur. The term "sulfur" shall be understood to include sulphoxide (S(O)) and sulphone (SO$_2$). The term "nitrogen" shall be understood to include nitrogen oxide (NO). Het$^1$ binds to nitrogen in 4-position on the isothiazol -3(2H)-one 1,1-dioxide. Examples of said "Het$^1$" include, but are not limited to, furan, pyrrole, pyrazine, pyrazole, imidazole, triazole, pyrimidine, pyridazine, pyridine, pyridine-1-oxide, isoxazole, oxazole, isothiazole, thiazole, thiophene, 1,2,4-triazole, furazane, 1,2,3-oxadiazole, 1,2,4-oxadiazole, 1,2,5-oxadiazole, 1,3,4-oxadiazole, 1,2,5-thiadiazole, 1,2,4-thiadiazole and 1,2,3-thiadiazole.

The term "Het$^2$" denotes a saturated or unsaturated non-aromatic 3, 4, 5, 6, 7, 8, 9 or 10 membered monocyclic ring in which one or more of the atoms in the ring is an element other than carbon independently selected from one or more of for example nitrogen, oxygen or sulfur, and wherein the ring optionally is substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$. The term "sulfur" shall be understood to include sulphoxide (S(O)) and sulphone (SO$_2$). The term "nitrogen" shall be understood to include nitrogen oxide (NO). Examples of said "Het$^2$" include, but are not limited to aziridine, azetidine, 2-pyrroline, 3-pyrroline, pyrrolidine, imidazoline, piperidine, piperazine, 2-pyrazoline, oxirane, oxetane, tetrahydrofuran, tetrahydropyran, 1,4-dioxane, 1,3-dioxolane, 1,2-oxathiolane, morpholine, 3-pyrazoline, pyrazolidine, 2H-pyrane, 4H-pyrane, 1,4-dithiane, 1,4-oxathiane, azepane and thiomorpholine.

The term "Het$^3$" denotes an aromatic 5 or 6 membered monocyclic ring in which one or more of the atoms in the ring is an element other than carbon independently selected from one or more of for example nitrogen, oxygen and sulfur, and which is substituted by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, OC(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$. The term "sulfur" shall be understood to include sulphoxide (S(O)) and sulphone (SO$_2$). The term "nitrogen" shall be understood to include nitrogen oxide (NO). Examples of said "Het$^3$" include, but are not limited to, furan, pyrrole, pyrazine, pyrazole, imidazole, triazole, pyrimidine, pyridazine, pyridine, pyridine-1-oxide, isoxazole, oxazole, isothiazole, thiazole, thiophene, 1,2,4-triazole, furazane, 1,2,3-oxadiazole, 1,2,4-oxadiazole, 1,2,5-oxadiazole, 1,3,4-oxadiazole, 1,2,5-thiadiazole, 1,2,4-thiadiazole and 1,2,3-thiadiazole.

The term "Het$^4$" denotes an aromatic or partly aromatic 8, 9 or 10 membered bicyclic ring system in which one or more of the atoms in the ring optionally is an element other than carbon independently selected from one or more of for example nitrogen, oxygen and sulfur. Het$^4$ binds to nitrogen in 4-position on the isothiazol-3(2H)-one 1,1-dioxide through the aromatic part of the bicyclic ring. The term "sulfur" shall be understood to include sulphoxide (S(O)) and sulphone (SO$_2$). The term "nitrogen" shall be understood to include nitrogen oxide (NO). Examples of said "Het$^4$" include, but are not limited to, thieno[2,3-b]furan, benzo[b]furan, benzo[c]furan, indole, isoindole, indolizine, 3H-indole, indoline, isoindoline, benzo[b]thiophene, benzo[c]thiophene, 1H-indazole, 2,3-dihydro-1H-indazole, benzimidazole, 1,3-benzoxazole, 1,3-dihydro-2,1-benzisoxazole, 1,2-benzisoxazole, 1,3-benzothiazole, 1,2-benzisothiazole, 1,3-dihydro-2,1-benzisothiazole, purine, quinoline, 3,4-dihydroquinoline, 1,2-dihydroquinoline, 1,2,3,4-tetrahydroquinoline, isoquinoline, 3,4-dihydroisoquinoline, 1,2-dihydroisoquinoline, 1,2,3,4-tetrahydroisoquinoline, 4H-quinolizine, quinoxaline, quinazoline, cinnoline, phtalazine, 1,8-naphtyridine, chroman and isochroman.

R$^a$ independently represents H or a straight or branched, saturated or unsaturated C$_1$-C$_4$alkyl chain optionally substituted by one or more F.

R$^b$ independently represents a straight or branched, saturated or unsaturated C$_1$-C$_4$alkyl chain optionally substituted by one or more F.

R$^c$ independently represents H or a straight or branched, saturated or unsaturated C$_1$-C$_3$alkyl chain optionally substituted by one or more F.

It shall be understood that when a substituent bears more than one of $R^a$, $R^b$ or $R^c$ then each of these will be the same or different. For example, $NR^aR^a$ includes amino, alkylamino and dialkylamino. Furthermore, it shall be understood that when different substituents in the same compound bear more than one of $R^a$, $R^b$ or $R^c$ then these will be the same or different.

Further values of $R^1$, $R^2$ and $R^3$ in compounds of formula I now will follow. It will be understood that such values may be used where appropriate with any of the definitions, claims or embodiments defined hereinbefore or hereinafter.

In a first group of compounds of formula I $R^1$ represents

X which is optionally substituted by one or more of the following: F, OH, CN, $NR^aR^a$, $OR^b$, $SR^b$, $S(O)R^b$, $SO_2R^bC(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$ or $NR^aC(O)NR^aR^a$;

cycloalkyl or heterocyclyl each optionally substituted by one or more of the following: F, OH, CN, $N^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NHC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$ or $NR^aC(O)NR^aR^a$;

phenyl or heteroaryl each optionally substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^a$-$C(O)NR^aR^a$, $SO_2NHC(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$ or $NR^aC(O)NR^aR^a$;

cycloalkylY or heterocyclylY wherein cycloalkyl or heterocyclyl each optionally is substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$ or $NR^aC(O)NR^aR^a$;

phenylY or heteroarylY wherein phenyl or heteroaryl each optionally is substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$ or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$ or $NR^aC(O)NR^aR^a$;

$R^2$ represents phenyl which is optionally substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$;

$R^3$ represents aryl or $Het^1$ wherein aryl or $Het^1$ each optionally is substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, Q, $Het^2$, R, $Het^3$, QZ, $Het^2Z$, RZ, $Het^3Z$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$;

$Het^4$ or T wherein $Het^4$ or T each optionally is substituted on the aromatic ring by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, Q, $Het^2$, R, $Het^3$, QZ, $Het^2Z$, RZ, $Het^3Z$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$, and wherein $Het^4$ or T each optionally is substituted on the non-aromatic ring by one or more of the following: F, OH, CN, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, thioxo, Q, $Het^2$, R, $Het^3$, QZ, $Het^2Z$, RZ, $Het^3Z$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

In a second group of compounds of formula I $R^1$ represents

X which is optionally substituted by one or more of the following: F, OH, CN, $NR^aR^a$, $OR^b$, $SR^b$, $S(O)R^b$, $SO_2R^b$, $C(O)R^b$, or $C_1$-$C_4$alkyl which is optionally substituted by one or more of the following: F, OH, CN, $NR^aR^b$, $OR^b$, $SR^b$, $S(O)R^b$, $SO_2R^b$ or $C(O)R^b$;

cycloalkyl or heterocyclyl each optionally substituted by one or more of the following: F, OH, CN, $NR^aR^a$, $OR^b$, $SR^b$, $S(O)R^b$, $SO_2R^b$, $C(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$ or $C(O)R^b$;

phenyl or heteroaryl each optionally substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$ or $C(O)R^b$;

cycloalkylY or heterocyclylY wherein cycloalkyl or heterocyclyl each optionally is substituted by one or more of the following: F, OH, CN, $NR^aR^a$, $OR^b$, $SR^b$, $S(O)R^b$, $SO_2R^b$, $C(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$ or $C(O)R^b$;

phenylY or heteroarylY wherein phenyl or heteroaryl each optionally is substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$ or $C(O)R^b$;

$R^2$ represents phenyl which is optionally substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$ or $C(O)R^b$, $R^3$ is the same as in the first group of compounds of formula I.

In a third group of compounds of formula I $R^1$ represents

X which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$ or $NR^aC(O)NR^aR^a$;

$R^2$ is the same as in the second group of compound of formula I, $R^3$ is the same as in the first group of compound of formula I.

In a fourth group of compounds of formula I $R^1$ represents

X which is optionally substituted by one or more of the following: F, OH, CN, $NR^aR^a$, $OR^b$, $SR^b$, $S(O)R^b$, $SO_2R^b$, $C(O)R^b$ or $C_1$-$C_4$alkyl which is optionally substituted by one or more of the following: F, OH, CN, $NR^aR^a$, $OR^b$, $SR^b$, $S(O)R^b$, $SO_2R^b$ or $C(O)R^b$;

$R^2$ is the same as in the second group of compound of formula I, $R^3$ is the same as in the first group of compound of formula I.

In a fifth group of compounds of formula I $R^1$ is the same as in the first group of compounds of formula I, $R^2$ is the same as in the first group of compounds of formula I, $R^3$ represents aryl or $Het^1$ wherein aryl or $Het^1$ each is substituted by one of the following: Q, $Het^2$, R or $Het^3$ and wherein aryl or $Het^1$ each is optionally substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

In a sixth group of compounds of formula I $R^1$ is the same as in the first group of compounds of formula I, $R^2$ is the same as in the first group of compounds of formula I, $R^3$ represents aryl or $Het^1$ wherein aryl or $Het^1$ each optionally is substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, QZ, $Het^2Z$, RZ, $Het^3Z$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

In a seventh group of compounds of formula I $R^1$ is the same as in the first group of compounds of formula I, $R^2$ is the same as in the first group of compounds of formula I, $R^3$ represents $Het^4$ or T wherein $Het^4$ or T each optionally is substituted on the aromatic ring by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, Q, $Het^2$, R, $Het^3$, QZ, $Het^2Z$, RZ, $Het^3Z$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$, and wherein $Het^4$ or T each optionally is substituted on the non-aromatic ring by one or more of the following: F, OH, CN, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, thioxo, Q, $Het^2$, R, $Het^3$, QZ, $Het^2Z$, RZ, $Het^3Z$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

In an $8^{th}$ group of compounds of formula I $R^1$ is the same as in the second group of compounds of formula I, $R^2$ is the same as in the second group of compounds of formula I, $R^3$ represents aryl or $Het^1$ wherein aryl or $Het^1$ each is substituted by one of the following: Q, $Het^2$, R or $Het^3$ and wherein aryl or $Het^1$ each is optionally substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following: F, OH, CN, $NR^aR^a$, $OR^b$, $SR^b$, $S(O)R^b$ $SO_2R^bC(O)R^b$, $C(O)NR^aR^a$, $NR^aC(O)R^bC(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

In a $9^{th}$ group of compounds of formula I $R^1$ is the same as in the second group of compounds of formula I, $R^2$ is the same as in the second group of compounds of formula I, $R^3$ represents aryl or $Het^1$ wherein aryl or $Het^1$ each optionally is substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, QZ, Het$^2$Z, RZ, Het$^3$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

In a 10$^{th}$ group of compounds of formula I
R$^1$ is the same as in the second group of compounds of formula I,
R$^2$ is the same as in the second group of compounds of formula I,
R$^3$ represents
Het$^4$ or T
wherein Het$^4$ or T each optionally is substituted on the aromatic ring by one or more of the following: halogen (Cl, F, I, Br), OH, CN, NO$_2$, NR$^a$R$^a$, OR$^b$, SR$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, Q, Het$^2$, R, Het$^3$, QZ, Het$^2$Z, RZ, Het$^3$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)N$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$, and wherein Het$^4$ or T each optionally is substituted on the non-aromatic ring by one or more of the following: F, OH, CN, NR$^a$R$^a$, OR$^b$, SR$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, thioxo, Q, Het$^2$, R, Het$^3$, QZ, Het$^2$Z, RZ, Het$^3$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

In an 11$^{th}$ group of compounds of formula I
R$^1$ is the same as in the third group of compounds of formula I,
R$^2$ is the same as in the third group of compounds of formula I,
R$^3$ represents
aryl or Het$^1$ wherein aryl or Het$^1$ each is substituted by one of the following: Q, Het$^2$, R or Het$^3$ and wherein aryl or Het$^1$ each is optionally substituted by one or more of the following:
halogen (Cl, F, I, Br), OH, CN, NO$_2$, NR$^a$R$^a$, OR$^b$, SR$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following: F, OH, CN, NR$^a$R$^a$, OR$^b$, SR$^b$, S(OR$^b$, SO$_2$R$^b$, C(OR$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

In a 12$^{th}$ group of compounds of formula I
R$^1$ is the same as in the third group of compounds of formula I,
R$^2$ is the same as in the third group of compounds of formula I,
R$^3$ represents
aryl or Het$^1$ wherein aryl or Het$^1$ each optionally is substituted by one or more of the following: halogen (Cl, F, I, Br), OH, CN, NO$_2$, NR$^a$R$^a$, OR$^b$, SR$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, QZ, Het$^2$Z, RZ, Het$^3$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

In a 13$^{th}$ group of compounds of formula I
R$^1$ is the same as in the third group of compounds of formula I,
R$^2$ is the same as in the third group of compounds of formula I,
Het$^4$ or T
wherein Het$^4$ or T each optionally is substituted on the aromatic ring by one or more of the following: halogen (Cl, F, I, Br), OH, CN, NO$_2$, NR$^a$R$^a$, OR$^b$, SR$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, Q, Het$^2$, R, Het$^3$, QZ, Het$^2$Z, RZ, Het$^3$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$, and wherein Het$^4$ or T each optionally is substituted on the non-aromatic ring by one or more of the following: F, OH, CN, NR$^a$R$^a$, OR$^b$, SR$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, thioxo, Q, Het$^2$, R, Het$^3$, QZ, Het$^2$Z, RZ, Het$^3$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

In a 14$^{th}$ group of compounds of formula I
R$^1$ is the same as in the fourth group of compounds of formula I,
R$^2$ is the same as in the fourth group of compounds of formula I,
R$^3$ represents
aryl or Het$^1$ wherein aryl or Het$^1$ each is substituted by one of the following: Q, Het$^2$, R or Het$^3$ and wherein aryl or Het$^1$ each is optionally substituted by one or more of the following: halogen (Cl, F, I, Br), OH, CN, NO$_2$, NR$^a$R$^a$, OR$^b$, SR$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

In a 15$^{th}$ group of compounds of formula I
R$^1$ is the same as in the fourth group of compounds of formula I,
R$^2$ is the same as in the fourth group of compounds of formula I,
R$^3$ represents
aryl or Het$^1$ wherein aryl or Het$^1$ each optionally is substituted by one or more of the following: halogen (Cl, F, I, Br), OH, CN, NO$_2$, NR$^a$R$^a$, OR$^b$, SR$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, SO$_2$NHC(O)R$^b$QZ, Het$^2$Z, RZ, Het$^3$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

In a 16$^{th}$ group of compounds of formula I

R$^1$ is the same as in the fourth group of compounds of formula I,

R$^2$ is the same as in the fourth group of compounds of formula I,

R$^3$ represents

Het$^4$ or T wherein Het$^4$ or T each optionally is substituted on the aromatic ring by one or more of the following: halogen (Cl, F, I, Br), OH, CN, NO$_2$, NR$^a$R$^a$, OR$^b$, SR$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, Q, Het$^2$, R, Het$^3$, QZ, Het$^2$Z, RZ, Het$^3$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$, and wherein Het$^4$ or T each optionally is substituted on the non-aromatic ring by one or more of the following: F, OH, CN, NR$^a$R$^a$, OR$^b$, SR$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, thioxo, Q, Het$^2$, R, Het$^3$, QZ, Het$^2$Z, RZ, Het$^3$Z, or C$_1$-C$_4$alkyl which is optionally substituted by one or more of the following: F, OH, CN, NR$^a$R$^a$, OR$^b$, SR$^b$, S(O) R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

Further Embodiments of the Invention

According to another embodiment of the invention there is provided a compound of general formula (I)

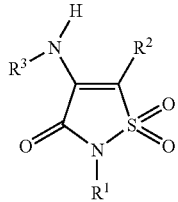

formula (I)

or a pharmaceutically acceptable salt thereof, wherein

R$^1$ represents

X which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$ or NR$^a$C(O)NR$^a$R$^a$;

cycloalkyl or heterocyclyl each optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

phenyl or heteroaryl each optionally substituted by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

cycloalkylY or heterocyclylY wherein cycloalkyl or heterocyclyl each optionally is substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$; phenylY or heteroarylY wherein phenyl or heteroaryl each optionally is substituted by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^c$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

R$^2$ represents phenyl which is optionally substituted by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$;

R$^3$ represents aryl or Het$^1$ wherein aryl or Het$^1$ each optionally is substituted by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, Q, Het$^2$, R, Het$^3$, QZ, Het$^2$Z, RZ, Het$^3$Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$;

Het$^4$ or T wherein Het$^4$ or T each optionally is substituted on the aromatic ring by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, (O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$NR$^a$C(O)NR$^a$R$^a$, SO$_2$NHC(O)R$^b$, Q, Het$^2$, R, Het$^3$, QZ, Het$^2$Z, RZ, Het$^3$Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$, and wherein Het$^4$ or T each optionally is substituted on the non-aromatic ring by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, thioxo, Q, Het$^2$, R, Het$^3$, QZ, Het$^2$Z, RZ, Het$^3$Z, or C$_1$-C$_4$alkyl which is optionally substituted by one or more of the following independently selected from: F, OH, CN, NR$^a$R$^{a1}$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

Further values of R$^1$, R$^2$ and R$^3$ will now follow. It will be understood that such values may be used where appropriate with any of the definitions, claims or embodiments defined hereinbefore or hereinafter.

In a first embodiment of the invention there is provided a class of compounds of formula (I) wherein R$^1$ represents X which is optionally substituted by one or more of the following independently selected from: F, OH, CN, NR$^a$R$^a$R$^b$OR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$ or NR$^a$C(O)NR$^a$R$^a$;

cycloalkyl or heterocyclyl each optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

phenyl or heteroaryl each optionally substituted by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O) OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$; cycloalkylY or heterocyclylY wherein cycloalkyl or heterocyclyl each optionally is substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O) OR$^a$, OC(O)R$^b$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

phenylY or heteroarylY wherein phenyl or heteroaryl each optionally is substituted by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^c$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

R$^2$ represents phenyl which is optionally substituted by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O) NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$;

R$^3$ represents aryl or Het$^1$ wherein aryl or Het$^1$ each optionally is substituted by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, Q, Het$^2$, R, Het$^3$, QZ, Het$^2$Z, RZ, Het$^3$Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$;

Het$^4$ or T wherein Het$^4$ or T each optionally is substituted on the aromatic ring by one or more of the following independently selected from: halogen (Cl, F, I, Br), OH, CN, NO$_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, Q, $Het^2$, R, $Het^3$, QZ, $Het^2Z$, RZ, $Het^3Z$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$, and wherein $Het^4$ or T each optionally is substituted on the non-aromatic ring by one or more of the following independently selected from: F, OH, CN, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, thioxo, Q, $Het^2$, R, $Het^3$, QZ, $Het^2Z$, RZ, $Het^3Z$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

In a second embodiment of the invention there is provided a class of compounds of formula (I) wherein $R^1$ represents X which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$ or $C(O)R^b$;

cycloalkyl or heterocyclyl each optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$ or $C(O)R^b$;

phenyl or heteroaryl each optionally substituted by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$ or $C(O)R^b$;

cycloalkylY or heterocyclylY wherein cycloalkyl or heterocyclyl each optionally is substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$ or $C(O)R^b$;

phenylY or heteroarylY wherein phenyl or heteroaryl each optionally is substituted by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$ or $C(O)R^b$;

$R^2$ represents phenyl which is optionally substituted by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$ or $C(O)R^b$.

$R^3$ is the same as for the first embodiment.

In a third embodiment of the invention there is provided a class of compounds of formula (I) wherein $R^1$ represents X which is optionally substituted by one or more of the following independently selected from: F, OH, CN, $NR^aR^a$, $OR^b$, $SR^b$, $SiR^bR^bR^b$, $S(O)R^b$, $SO_2R^bC(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$ or $NR^aC(O)NR^aR^a$, $R^2$ is the same as for the second embodiment, and $R^3$ is the same as for the first embodiment.

In a fourth embodiment of the invention there is provided a class of compounds of formula (I) wherein $R^1$ represents X which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, or $C_1$-$C_4$alkyl which is optionally substituted by one or more of the following independently selected from: F, OH, CN, $NR^aR^a$, $OR^bSR^b$, $SiR^bR^bR^b$, $S(O)R^b$, $SO_2R^b$ or $C(O)R^b$, $R^2$ is the same as for the second embodiment, and $R^3$ is the same as for the first embodiment.

In a fifth embodiment of the invention there is provided a class of compounds of formula (I) wherein $R^1$ is the same as for the first embodiment, $R^2$ is the same as for the first embodiment, and $R^3$ represents aryl or $Het^1$ wherein aryl or $Het^1$ each is substituted by one of the following: Q, $Het^2$, R or $Het^3$ and wherein aryl or $Het^1$ each is optionally substituted by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

In a sixth embodiment of the invention there is provided a class of compounds of formula (I) wherein $R^1$ is the same as for the first embodiment, $R^2$ is the same as for the first embodiment, and $R^3$ represents aryl or $Het^1$ wherein aryl or $Het^1$ each optionally is substituted by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, QZ, $Het^2Z$, RZ, $Het^3Z$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

In a seventh embodiment of the invention there is provided a class of compounds of formula (I) wherein $R^1$ is the same as for the first embodiment,
$R^2$ is the same as for the first embodiment, and
$R^3$ represents
$Het^4$ or T
wherein $Het^4$ or T each optionally is substituted on the aromatic ring by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, Q, $Het^2$, R, $Het^1$, QZ, $Het^2Z$, RZ, $Het^1$ Z, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$, and wherein $Het^4$ or T each optionally is substituted on the non-aromatic ring by one or more of the following independently selected from: F, OH, CN, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, thioxo, Q, $Het^2$, R, $Het^3$, QZ, $Het^2Z$, RZ, $Het^3Z$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$ In a 8$^{th}$ embodiment of the invention there is provided a class of compounds of formula (I) wherein
$R^1$ is the same as for the second embodiment,
$R^2$ is the same as for the second embodiment, and
$R^3$ represents
aryl or $Het^1$ wherein aryl or $Het^1$ each is substituted by one of the following: Q, $Het^2$, R or $Het^3$ and wherein aryl or $Het^1$ each is optionally substituted by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

In a 9$^{th}$ embodiment of the invention there is provided a class of compounds of formula (I) wherein
$R^1$ is the same as for the second embodiment,
$R^2$ is the same as for the second embodiment, and
$R^3$ represents
aryl or $Het^1$ wherein aryl or $Het^1$ each optionally is substituted by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2N^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, QZ, $Het^2Z$, RZ, $Het^3Z$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)$ $NR^aR^a$ or $NR^aC(O)NR^aR^a$.

In a 10$^{th}$ embodiment of the invention there is provided a class of compounds of formula (I) wherein
$R^1$ is the same as for the second embodiment,
$R^2$ is the same as for the second embodiment, and
$R^3$ represents
$Het^4$ or T
wherein $Het^4$ or T each optionally is substituted on the aromatic ring by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, Q, $Het^2$, R, $Het^3$, QZ, $Het^2Z$, RZ, $Het^3Z$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$,
and wherein $Het^4$ or T each optionally is substituted on the non-aromatic ring by one or more of the following independently selected from: F, OH, CN, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, thioxo, Q, $Het^2$, R, $Het^1$, QZ, $Het^2Z$, RZ, $Het^3Z$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

In a 11$^{th}$ embodiment of the invention there is provided a class of compounds of formula (I) wherein
$R^1$ is the same as for the third embodiment,
$R^2$ is the same as for the third embodiment, and
$R^3$ represents
aryl or $Het^1$ wherein aryl or $Het^1$ each is substituted by one of the following: Q, $Het^2$, R or $Het^3$ and wherein aryl or $Het^1$ each is optionally substituted by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

In a 12$^{th}$ embodiment of the invention there is provided a class of compounds of formula (I) wherein
$R^1$ is the same as for the third embodiment,
$R^2$ is the same as for the third embodiment, and
$R^3$ represents
aryl or $Het^1$ wherein aryl or $Het^1$ each optionally is substituted by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, QZ, $Het^2Z$, RZ, $Het^3Z$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

In a 13th embodiment of the invention there is provided a class of compounds of formula (I) wherein
$R^1$ is the same as for the third embodiment,
$R^2$ is the same as for the third embodiment, and
$R^3$ represents
$Het^4$ or T
wherein $Het^4$ or T each optionally is substituted on the aromatic ring by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, Q, $Het^2$, R, $Het^3$, QZ, $Het^2Z$, RZ, $Het^3Z$, or $C_1$-$C_4$alkyl which is optionally substituted by one or more of the following independently selected from: F, OH, CN, $NR^aR^a$, $OR^b$, $SR^bSiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$, and wherein $Het^4$ or T each optionally is substituted on the non-aromatic ring by one or more of the following independently selected from: F, OH, CN, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, thioxo, Q, $Het^2$, R, $Het^3$, QZ, $Het^2Z$, RZ, $Het^3Z$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

In a 14th embodiment of the invention there is provided a class of compounds of formula (I) wherein
$R^1$ is the same as for the fourth embodiment,
$R^2$ is the same as for the fourth embodiment, and
$R^3$ represents
aryl or $Het^1$ wherein aryl or $Het^1$ each is substituted by one of the following: Q, $Het^2$, R or $Het^3$ and wherein aryl or $Het^1$ each is optionally substituted by one or more of the following: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

In a 15th embodiment of the invention there is provided a class of compounds of formula (I) wherein
$R^1$ is the same as for the fourth embodiment,
$R^2$ is the same as for the fourth embodiment, and
$R^3$ represents
aryl or $Het^1$ wherein aryl or $Het^1$ each is optionally substituted by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, QZ, $Het^2Z$, RZ, $Het^3Z$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

In a 16th embodiment of the invention there is provided a class of compounds of formula (I) wherein
$R^1$ is the same as for the fourth embodiment,
$R^2$ is the same as for the fourth embodiment, and
$R^3$ represents
$Het^4$ or T
wherein $Het^4$ or T each optionally is substituted on the aromatic ring by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, Q, $Het^2$, R, $Het^3$, QZ, $Het^2Z$, RZ, $Het^3Z$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$, and wherein $Het^4$ or T each optionally is substituted on the non-aromatic ring by one or more of the following independently selected from: F, OH, CN, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, thioxo, Q, $Het^2$, R, $Het^3$, QZ, $Het^2Z$, RZ, $Het^3Z$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

The compounds of formula I have activity as medicaments. In particular the compounds of formula I are LXR agonists.

Specific compounds of the invention are one or more of the following:

2-tert-butyl-4-[(4-morpholin-4-ylphenyl)amino]-5-phenyl-isothiazol-3(2H)-one 1,1-dioxide 2-tert-butyl-4-[(4-methoxyphenyl)amino]-5-phenylisothiazol-3(2H)-one 1,1-dioxide 2-tert-butyl-5-phenyl-4-[(4-piperidin-1-ylphenyl)amino]isothiazol-3(2H)-one 1,1-dioxide 2-tert-butyl-4-[(4-isopropoxyphenyl)amino]-5-phenyl-isothiazol-3(2H)-one 1,1-dioxide 2-tert-butyl-5-phenyl-4-[(4-pyrrolidin-1-ylphenyl)amino]isothiazol-3(2H)-one 1,1-dioxide tert-butyl {4-[(2-tert-butyl-1,1-dioxido-3-oxo-5-phenyl-2,3-dihydroisothiazol-4-yl)amino]phenyl}carbamate 4-[(4-isopropoxyphenyl)amino]-2-isopropyl-5-phenyl-isothiazol-3(2H)-one 1,1-dioxide 2-isopropyl-5-phenyl-4-[(4-piperidin-1-ylphenyl)amino]isothiazol-3(2H)-one 1,1-dioxide 4-[(4-azepan-1-ylphenyl)amino]-2-tert-butyl-5-phenyl-isothiazol-3(2H)-one 1,1-dioxide 2-isopropyl-4-[(4-morpholin-4-ylphenyl)amino]-5-phenyl-isothiazol-3(2H)-one 1,1-dioxide 2-butyl-4-[(4-methoxyphenyl)amino]-5-phenylisothiazol-3(2H)-one 1,1-dioxide 4-[(2-acetyl-1-benzofuran-5-yl)amino]-2-butyl-5-phenyl-isothiazol-3(2H)-one 1,1-dioxide
2-tert-butyl-4-[(6-morpholin-4-ylpyridin-3-yl)amino]-5-phenylisothiazol-3(2H)-one 1,1-dioxide
2-butyl-4-{[4-(difluoromethoxy)phenyl]amino}-5-phenyl-isothiazol-3(2H)-one 1,1-dioxide
2-butyl-4-[(4-morpholin-4-ylphenyl)amino]-5-phenyl-isothiazol-3(2H)-one 1,1-dioxide tert-butyl 6-[(2-butyl-1,1-dioxido-3-oxo-5-phenyl-2,3-dihydroisothiazol-4-yl)amino]-3,4-dihydroisoquinoline-2(1H)-carboxylate
2-butyl-4-[(3-chloro-4-morpholin-4-ylphenyl)amino]-5-phenylisothiazol-3(2H)-one 1,1-dioxide
2-butyl-5-(3-chlorophenyl)-4-[(4-morpholin-4-ylphenyl)amino]isothiazol-3(2H)-one 1,1-dioxide
2-ethyl-4-[(4-morpholin-4-ylphenyl)amino]-5-phenyl-isothiazol-3(2H)-one 1,1-dioxide
4-[(2-acetyl-1,2,3,4-tetrahydroisoquinolin-6-yl)amino]-2-butyl-5-phenylisothiazol-3(2H)-one 1,1-dioxide
2-butyl-4-[(4-hydroxyphenyl)amino]-5-phenylisothiazol-3(2H)-one 1,1-dioxide
2-butyl-4-(1H-indol-5-ylamino)-5-phenylisothiazol-3(2H)-one 1,1-dioxide
5-[(2-butyl-1,1-dioxido-3-oxo-5-phenyl-2,3-dihydroisothiazol-4-yl)amino]-N,N-dimethyl-1-benzofuran-2-carboxamide
2-[4-(difluoromethoxy)benzyl]-4-[(4-morpholin-4-ylphenyl)amino]-5-phenylisothiazol-3(2H)-one 1,1-dioxide
2-butyl-5-(3-chlorophenyl)-4-{[4-(difluoromethoxy)phenyl]amino}isothiazol-3(2H)-one 1,1-dioxide
2-butyl-5-phenyl-4-{[4-(trifluoromethoxy)phenyl]amino}isothiazol-3(2H)-one 1,1-dioxide
2-butyl-4-{[4-(hydroxymethyl)phenyl]amino}-5-phenyl-isothiazol-3(2H)-one 1,1-dioxide
4-{[4-(benzyloxy)phenyl]amino}-2-butyl-5-phenylisothiazol-3(2H)-one 1,1-dioxide
4-{[4-(4-benzylpiperazin-1-yl)phenyl]amino}-2-butyl-5-phenylisothiazol-3 (2H)-one 1,1-dioxide
2-[4-(difluoromethoxy)benzyl]-4-[(4-methoxyphenyl)amino]-5-phenylisothiazol-3(2H)-one 1,1-dioxide
4-(1-benzofuran-5-ylamino)-2-butyl-5-phenylisothiazol-3(2H)-one 1,1-dioxide
2-butyl-5-(4-chlorophenyl)-4-{[4-(difluoromethoxy)phenyl]amino}isothiazol-3(2H)-one 1,1-dioxide
2-butyl-5-phenyl-4-(1H-1,2,4-triazol-3-ylamino)isothiazol-3(2H)-one 1,1-dioxide
2-butyl-4-[(5-methyl-1-phenyl-1H-pyrazol-3-yl)amino]-5-phenylisothiazol-3(2H)-one 1,1-dioxide
2-butyl-4-[(6-methoxypyridin-3-yl)amino]-5-phenylisothiazol-3(2H)-one 1,1-dioxide
4-[(2-acetyl-1-benzofuran-5-yl)amino]-2-(2-ethoxyethyl)-5-phenylisothiazol-3(2H)-one 1,1-dioxide
2-[4-(difluoromethoxy)benzyl]-4-{[4-(difluoromethoxy)phenyl]amino}-5-phenylisothiazol-3(2H)-one 1,1-dioxide
2-butyl-5-phenyl-4-[(2-thioxo-2,3-dihydro-1,3-benzothiazol-6-yl)amino]isothiazol-3(2H)-one 1,1-dioxide
2-methyl-4-[(4-morpholin-4-ylphenyl)amino]-5-phenyl-isothiazol-3(2H)-one 1,1-dioxide
4-[(4-methoxyphenyl)amino]-2-methyl-5-phenylisothiazol-3(2H)-one 1,1-dioxide
4-[(4-cyclohexylphenyl)amino]-2-(2-methoxyethyl)-5-phenylisothiazol-3(2H)-one 1,1-dioxide
4-[(2-acetyl-1-benzofuran-5-yl)amino]-2-methyl-5-phenyl-isothiazol-3(2H)-one 1,1-dioxide
2-(2-methoxyethyl)-5-phenyl-4-(5,6,7,8-tetrahydronaphthalen-1-ylamino)isothiazol-3(2H)-one 1,1-dioxide
4-(1H-indol-5-ylamino)-2-(2-methoxyethyl)-5-phenyl-isothiazol-3(2H)-one 1,1-dioxide
4-[(4-fluorophenyl)amino]-2-methyl-5-phenylisothiazol-3(2H)-one 1,1-dioxide
2-[(6-aminopyridin-3-yl)methyl]-4-[(4-morpholin-4-ylphenyl)amino]-5-phenylisothiazol-3(2H)-one 1,1-dioxide
N-({4-[(2-butyl-1,1-dioxido-3-oxo-5-phenyl-2,3-dihydroisothiazol-4-yl)amino]phenyl}sulfonyl)acetamide
ethyl 5-[(2-butyl-1,1-dioxido-3-oxo-5-phenyl-2,3-dihydroisothiazol-4-yl)amino]-3-methyl-1-benzothiophene-2-carboxylate
5-[(2-butyl-1,1-dioxido-3-oxo-5-phenyl-2,3-dihydroisothiazol-4-yl)amino]-1-benzofuran-2-carboxylic acid
tert-butyl 5-[(2-butyl-1,1-dioxido-3-oxo-5-phenyl-2,3-dihydroisothiazol-4-yl)amino]-1-benzofuran-2-carboxylate
4-[(2-acetyl-1-benzofuran-5-yl)amino]-2-ethyl-5-[4-(trifluoromethyl)phenyl]isothiazol-3(2H)-one 1,1-dioxide
2-(2-methoxyethyl)-4-[(3-morpholin-4-yl-1H-1,2,4-triazol-5-yl)amino]-5-phenylisothiazol-3(2H)-one 1,1-dioxide
ethyl 5-{[2-(2-methoxyethyl)-1,1-dioxido-3-oxo-5-phenyl-2,3-dihydroisothiazol-4-yl]amino}-3-methyl-1-benzothiophene-2-carboxylate
4-[(5-cyclohexyl-2-methoxyphenyl)amino]-2-(2-methoxyethyl)-5-phenylisothiazol-3(2H)-one 1,1-dioxide
4-[(4-hydroxyphenyl)amino]-2-(2-methoxyethyl)-5-phenyl-isothiazol-3(2H)-one 1,1-dioxide
4-(1H-benzimidazol-2-ylamino)-2-butyl-5-phenylisothiazol-3(2H)-one 1,1-dioxide
2-[(6-aminopyridin-3-yl)methyl]-4-{[4-(difluoromethoxy)phenyl]amino}-5-phenylisothiazol-3(2H)-one 1,1-dioxide
2-methyl-4-[(6-morpholin-4-ylpyridin-3-yl)amino]-5-phenylisothiazol-3(2H)-one 1,1-dioxide
2-butyl-5-phenyl-4-(1,2,3,4-tetrahydroisoquinolin-6-ylamino)isothiazol-3(2H)-one 1,1-dioxide
5-[(2-butyl-1,1-dioxido-3-oxo-5-phenyl-2,3-dihydroisothiazol-4-yl)amino]-1H-isoindole-1,3(2H)-dione
2-butyl-4-[(2,5-diethoxy-4-morpholin-4-ylphenyl)amino]-5-phenylisothiazol-3(2H)-one 1,1-dioxide
2-(2-methoxyethyl)-4-[(4-morpholin-4-ylphenyl)amino]-5-phenylisothiazol-3(2H)-one 1,1-dioxide
4-{[4-(difluoromethoxy)phenyl]amino}-2-(2-methoxyethyl)-5-phenylisothiazol-3(2H)-one 1,1-dioxide
2-ethyl-4-[(4-morpholin-4-ylphenyl)amino]-5-[4-(trifluoromethyl)phenyl]isothiazol-3(2H)-one 1,1-dioxide
6-[(2-butyl-1,1-dioxido-3-oxo-5-phenyl-2,3-dihydroisothiazol-4-yl)amino]-N-methyl-3,4-dihydroisoquinoline-2(1H)-carboxamide
4-{[4-(difluoromethoxy)phenyl]amino}-2-methyl-5-phenylisothiazol-3(2H)-one 1,1-dioxide
4-[(2-acetyl-1-benzofuran-5-yl)amino]-2-ethyl-5-[4-(trifluoromethyl)phenyl]isothiazol-3(2H)-one 1,1-dioxide or a pharmaceutically acceptable salt or solvate thereof, or a solvate of such a salt.

In one aspect of the invention, there is provided a compound according to formula (I) in which $R^1$ is selected from methyl, ethyl, isopropyl, n-butyl, tert-butyl, 2-methoxyethyl, 6-aminopyridin-3-ylmethyl, 6-difluoromethoxyphenyl or 6-difluoromethoxybenzyl;

$R^2$ is selected from phenyl, 3-chlorophenyl, 4-chlorophenyl or 4-trifluoromethylphenyl; and $R^3$ is selected from 4-methoxyphenyl, 4-hydroxyphenyl, 4-isopropoxyphenyl, 4-difluoromethoxyphenyl, 4-trifluoromethoxyphenyl, 4-fluorophenyl, 4-hydroxymethylphenyl, 1-benzyloxyphenyl, 4-cyclohexylphenyl, 4-morpholin-4-ylphenyl, 4-piperidin-1-ylphenyl, 4-pyrrolidin-1-ylphenyl, 4-azepan-1-ylphenyl, 4-benzylpiperazin-1-ylphenyl, 4-(tertbutoxycarbonylamino)phenyl, 4-(N-acetylsulfonamide)phenyl, 2-dimethylaminocarbonyl-1-benzofuran-5-yl, 2-acetyl-1-benzofuran-5-yl, 2-tertbutoxycarbonyl-1-benzofuran-5-yl, 2-carboxy-1-benzofuran-5-yl, 1-benzofuran-5-yl, 2-ethoxycarbonyl-3-methyl-1-benzothiophene-5-yl, 1H-indol-5-yl, 6-morpholin-4-ylpyridin-3-yl, 6-methoxypyridin-3-yl, 5-cyclohexyl-2-methoxyphenyl, 3-chloro-4-morpholin-4-ylphenyl, 2,5-diethoxy-4-morpholin-4-ylphenyl, 2-acetyl-1,2,3,4-tetrahydroisoquinolin-6-yl, 2-methylaminocarbonyl-3,4-dihydroisoquinoline-2(1H)-6-yl, 1,2,3,4-tetrahydroisoquinolin-6-yl, 2-tertbutoxycarbonyl-3,4-dihydroisoquinoline-2(1H)-6-yl, 5,6,7,8-tetrahydronaphtalen-1-yl, 2-thioxo-2,3-dihydro-1,3-benzothiazol-6-yl, 1H-isoindole-1,3(2H)-dione-5-yl, 1H-benzimidazol-2-yl, 1H-1,2,4-triazol-3-yl, 3-morpholin-4-yl-1H-1,2,4-triazol-5-yl or 5-methyl-1-phenyl-pyrazol-3-yl.

In another aspect of the invention, there is provided a compound according to formula (V) in which $R^1$ is selected from methyl, ethyl, isopropyl, n-butyl, tert-butyl, 2-methoxyethyl, 6-aminopyridin-3-ylmethyl, 6-difluoromethoxyphenyl or 6-difluoromethoxybenzyl, and $R^2$ is selected from phenyl, 3-chlorophenyl, 4-chlorophenyl or 4-trifluoromethylphenyl.

In another aspect of the invention, there is provided a compound according to formula (VI) in which $R^1$ is selected from methyl, ethyl, isopropyl, n-butyl, tert-butyl, 2-methoxyethyl, 6-aminopyridin-3-ylmethyl, 6-difluoromethoxyphenyl or 6-difluoromethoxybenzyl, $R^2$ is selected from phenyl, 3-chlorophenyl, 4-chlorophenyl or 4-trifluoromethylphenyl and L is a leaving group such as for instance Cl, Br, I, p-toluensulfonate, methanesulfonate (MsO) or trifluoromethanesulfonate (OTf).

According to a further embodiment of the invention $R^1$ and $R^3$ are the same as for any claims, aspects or embodiments of the invention and $R^2$ is unsubstituted phenyl.

According to an alternative aspect of the invention $R^1$ and $R^2$ are as for any aspect, claim or embodiment hereinbefore or hereinafter, and $R^3$ represents aryl which is substituted by one of the following independently selected from: Q, $Het^2$, R or $Het^3$ and wherein aryl is optionally substituted by one or more of the following: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^a$-$C(O)NR^aR^a$, $SO_2NHC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

According to an alternative aspect of the invention $R^1$ and $R^2$ are as for any aspect, claim or embodiment hereinbefore or hereinafter, and $R^3$ represents aryl which is substituted by Q or $Het^2$ and wherein aryl is optionally substituted by one or more of the following: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^a$-$C(O)NR^aR^a$, $SO_2NHC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

According to an alternative aspect of the invention $R^1$ is as for any aspect, claim or embodiment hereinbefore or hereinafter, $R^2$ is unsubstituted phenyl, and $R^3$ represents aryl which is substituted by one of the following independently selected from: Q, $Het^2$, R or $Het^3$ and wherein aryl is optionally substituted by one or more of the following: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^a$-$C(O)NR^aR^a$, $SO_2NHC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

According to an alternative aspect of the invention $R^1$ is as for any aspect, claim or embodiment hereinbefore or hereinafter, $R^2$ is unsubstituted phenyl, and $R^3$ represents aryl which is substituted by Q or $Het^2$ and wherein aryl is optionally substituted by one or more of the following: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^a$-$C(O)NR^aR^a$, $SO_2NHC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

According to an alternative aspect of the invention $R^1$ and $R^2$ are as for any aspect, claim or embodiment hereinbefore or hereinafter, and $R^3$ represents $Het^1$ which is substituted by one of the following independently selected from: Q, $Het^2$, R or $Het^3$ and wherein $Het^1$ is optionally substituted by one or more of the following: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^a$-$C(O)NR^aR^a$, $SO_2NHC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

According to an alternative aspect of the invention $R^1$ and $R^2$ are as for any aspect, claim or embodiment hereinbefore or hereinafter, and $R^3$ represents $Het^1$ which is substituted by $Het^2$ or R and wherein $Het^1$ is optionally substituted by one or more of the following: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^a$-$C(O)NR^aR^a$, $SO_2NHC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

According to an alternative aspect of the invention R$^1$ is as for any aspect, claim or embodiment hereinbefore or hereinafter, R$^2$ is unsubstituted phenyl, and R$^3$ represents Het$^1$ which is substituted by one of the following independently selected from: Q, Het$^2$, R or Het$^3$ and wherein Het$^1$ is optionally substituted by one or more of the following: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

According to an alternative aspect of the invention R$^1$ is as for any aspect, claim or embodiment hereinbefore or hereinafter, R$^2$ is unsubstituted phenyl, and R$^3$ represents Het$^1$ which is substituted by Het$^2$ or R and wherein Het$^1$ is optionally substituted by one or more of the following: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

According to an alternative aspect of the invention R$^1$ and R$^2$ are as for any aspect, claim or embodiment hereinbefore or hereinafter, and R$^3$ represents aryl which optionally is substituted by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, QZ, Het$^2$Z, RZ, Het$^3$Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

According to an alternative aspect of the invention R$^1$ and R$^2$ are as for any aspect, claim or embodiment hereinbefore or hereinafter, and R$^3$ represents aryl which optionally is substituted by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

According to an alternative aspect of the invention R$^1$ is as for any aspect, claim or embodiment hereinbefore or hereinafter, R$^2$ is unsubstituted phenyl, and R$^3$ represents aryl which optionally is substituted by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, QZ, Het$^2$Z, RZ, Het$^3$Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

According to an alternative aspect of the invention R$^1$ is as for any aspect, claim or embodiment hereinbefore or hereinafter, R$^2$ is unsubstituted phenyl, and R$^3$ represents aryl which optionally is substituted by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

According to an alternative aspect of the invention R$^1$ and R$^2$ are as for any aspect, claim or embodiment hereinbefore or hereinafter, and R$^3$ represents Het$^1$ which optionally is substituted by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, QZ, Het$^2$Z, RZ, Het$^3$Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

According to an alternative aspect of the invention R$^1$ and R$^2$ are as for any aspect, claim or embodiment hereinbefore or hereinafter, and R$^3$ represents Het$^1$ which optionally is substituted by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$ or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

According to an alternative aspect of the invention R$^1$ is as for any aspect, claim or embodiment hereinbefore or hereinafter, R$^2$ is unsubstituted phenyl, and R$^3$ represents Het$^1$ which optionally is substituted by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, QZ, Het$^2$Z, RZ, Het$^3$Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

According to an alternative aspect of the invention R$^1$ is as for any aspect, claim or embodiment hereinbefore or hereinafter, R$^2$ is unsubstituted phenyl, and R$^3$ represents Het$^1$ which optionally is substituted by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$ or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

According to an alternative aspect of the invention R$^1$ and R$^2$ are as for any aspect, claim or embodiment hereinbefore or hereinafter, and R$^3$ represents Het$^4$ which optionally is substituted on the aromatic ring by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)$_b$, SO$_2$NR$^a$R$^a$, NR$^a$SO$_2$R$^b$, NR$^a$C(O)OR$^b$, OC(O)NR$^a$R$^a$, OSO$_2$R$^b$NR$^a$C(O)$_a$R$^a$, SO$_2$NHC(O)R$^b$, Q, Het$^2$, R, Het$^3$, QZ, Het$^2$Z, RZ, Het$^3$Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$ NR$^a$R$^a$, NR$^a$C(O)OR$^b$, OC(O)NR$^a$R$^a$ or NR$^a$C(O)NR$^a$R$^a$, and wherein Het$^4$ optionally is substituted on the non-aromatic ring by one or more of the following independently selected from: F, OH, CN, NR$^a$R$^a$, OR$^b$, SR$^{b1}$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, thioxo, Q, Het$^2$, R, Het$^3$, QZ, Het$^2$Z, RZ, Het$^3$Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

According to an alternative aspect of the invention R$^1$ and R$^2$ are as for any aspect, claim or embodiment hereinbefore or hereinafter, and R$^3$ represents Het$^4$ which optionally is substituted on the aromatic ring by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$, and wherein Het$^4$ optionally is substituted on the non-aromatic ring by one or more of the following independently selected from: F, OH, CN, NR$^a$, OR$^b$, SR$^b$, SiR$^b$R$^b$R$^b$ R$^b$R$^b$, S(O)R$^b$, C(O)OR$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, thioxo, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

According to an alternative aspect of the invention R$^1$ is as for any aspect, claim or embodiment hereinbefore or hereinafter, R$^2$ is unsubstituted phenyl, and R$^3$ represents Het$^4$ which optionally is substituted on the aromatic ring by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, Q, Het$^2$, R, Het$^3$, QZ, Het$^2$Z, RZ, Het$^3$Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$, and wherein Het$^4$ optionally is substituted on the non-aromatic ring by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, thioxo, Q, Het$^2$, R, Het$^3$, QZ, Het$^2$Z, RZ, Het$^3$Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

According to an alternative aspect of the invention R$^1$ is as for any aspect, claim or embodiment hereinbefore or hereinafter, R$^2$ is unsubstituted phenyl, and R$^3$ represents Het$^4$ which optionally is substituted on the aromatic ring by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$, and wherein Het$^4$ optionally is substituted on the non-aromatic ring by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, thioxo, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)$R^b$, SO$_2$$R^b$, C(O)$R^b$, C(O)NR$^a$R$^a$, NR$^a$C(O)$R^b$, C(O)OR$^a$, OC(O)$R^b$, NR$^a$SO$_2$$R^b$, SO$_2$NR$^a$R$^a$, NR$^a$C(O)OR$^b$, OC(O)NR$^a$R$^a$ or NR$^a$C(O)NR$^a$R$^a$.

According to an alternative aspect of the invention R$^1$ and R$^2$ are as for any aspect, claim or embodiment hereinbefore or hereinafter, and R$^3$ represents T which optionally is substituted on the aromatic ring by one or more of the following independently selected from: halogen (Cl, F, I, Br), OH, CN, NO$_2$, NR$^a$R$^a$, OR$^b$, SR$^b$, SiR$^b$R$^b$R$^b$, S(O)$R^b$, SO$_2$$R^b$, C(O)$R^b$, phenylC$_1$alkyl, C(O)NR$^a$R$^a$, NR$^a$C(O)$R^b$, C(O)OR$^a$, OC(O)$R^b$, SO$_2$NR$^a$R$^a$, NR$^a$SO$_2$$R^b$, NR$^a$C(O)OR$^b$, OC(O)NR$^a$R$^a$, OSO$_2$$R^b$, NR$^a$-C(O)NR$^a$R$^a$, SO$_2$NHC(O)$R^b$, Q, Het$^2$, R, Het$^3$, QZ, Het$^2$Z, RZ, Het$^3$Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)$R^b$, SO$_2$$R^b$, C(O)$R^b$, C(O)NR$^a$R$^a$, NR$^a$C(O)$R^b$, C(O)OR$^a$, OC(O)$R^b$, NR$^a$SO$_2$$R^b$, SO$_2$NR$^a$R$^a$, NR$^a$C(O)OR$^b$, OC(O)NR$^a$R$^a$ or NR$^a$C(O)NR$^a$R$^a$, and wherein T optionally is substituted on the non-aromatic ring by one or more of the following independently selected from: F, OH, CN, NR$^a$R$^a$, OR$^b$, SR$^b$, SiR$^b$R$^b$R$^b$, S(O)$R^b$, SO$_2$$R^b$, C(O)$R^b$, phenylC$_1$alkyl, C(O)NR$^a$R$^a$, NR$^a$C(O)$R^b$, C(O)OR$^a$, OC(O)$R^b$, SO$_2$NR$^a$R$^a$, NR$^a$SO$_2$$R^b$, NR$^a$C(O)OR$^b$, OC(O)NR$^a$R$^a$, NR$^a$C(O)NR$^a$R$^a$, thioxo, Q, Het$^2$, R, Het$^3$, QZ, Het$^2$Z, RZ, Het$^3$Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)$R^b$, SO$_2$$R^b$, C(O)$R^b$, C(O)NR$^a$R$^a$, NR$^a$C(O)$R^b$, C(O)OR$^a$, OC(O)$R^b$, NR$^a$SO$_2$$R^b$, SO$_2$NR$^a$R$^a$, NR$^a$C(O)OR$^b$, OC(O)NR$^a$R$^a$ or NR$^a$C(O)NR$^a$R$^a$.

According to an alternative aspect of the invention R$^1$ and R$^2$ are as for any aspect, claim or embodiment hereinbefore or hereinafter, and R$^3$ represents T which optionally is substituted on the aromatic ring by one or more of the following independently selected from: halogen (Cl, F, I, Br), OH, CN, NO$_2$, NR$^a$R$^a$, OR$^b$, SR$^b$, SiR$^b$R$^b$R$^b$, S(O)$R^b$, SO$_2$$R^b$, C(O)$R^b$, phenylC$_1$alkyl, C(O)NR$^a$R$^a$, NR$^a$C(O)$R^b$, C(O)OR$^a$, OC(O)$R^b$, SO$_2$NR$^a$R$^a$, NR$^a$SO$_2$$R^b$, NR$^a$C(O)OR$^b$, OC(O)NR$^a$R$^a$, OSO$_2$$R^b$, NR$^a$-C(O)NR$^a$R$^a$, SO$_2$NHC(O)$R^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)$R^b$, SO$_2$$R^b$, C(O)$R^b$, C(O)NR$^a$R$^a$, NR$^a$C(O)$R^b$, C(O)OR$^a$, OC(O)$R^b$, NR$^a$SO$_2$$R^b$, SO$_2$NR$^a$R$^a$, NR$^a$C(O)OR$^b$, OC(O)NR$^a$R$^a$ or NR$^a$C(O)NR$^a$R$^a$, and wherein T optionally is substituted on the non-aromatic ring by one or more of the following independently selected from: F, OH, CN, NR$^a$R$^a$, OR$^b$, SR$^b$, SiR$^b$R$^b$R$^b$, S(O)$R^b$, SO$_2$$R^b$, C(O)$R^b$, phenylC$_1$alkyl, C(O)NR$^a$R$^a$, NR$^a$C(O)$R^b$, C(O)OR$^a$, OC(O)$R^b$, SO$_2$NR$^a$R$^a$, NR$^a$SO$_2$$R^b$, NR$^a$C(O)OR$^b$, OC(O)NR$^a$R$^a$, NR$^a$C(O)NR$^a$R$^a$, thioxo, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)$R^b$, SO$_2$$R^b$, C(O)$R^b$, C(O)NR$^a$R$^a$, NR$^a$C(O)$R^b$, C(O)OR$^a$, OC(O)$R^b$, NR$^a$SO$_2$$R^b$, SO$_2$NR$^a$R$^a$, NR$^a$C(O)OR$^b$, OC(O)NR$^a$R$^a$ or NR$^a$C(O)N-R$^a$R$^a$, and wherein T optionally is substituted on the non-aromatic ring by one or more of the following independently selected from: F, OH, CN, NR$^a$R$^a$, OR$^b$, SR$^b$, SiR$^b$R$^b$R$^b$, S(O)$R^b$, SO$_2$$R^b$, C(O)$R^b$, phenylC$_1$alkyl, C(O)NR$^a$R$^a$, NR$^a$C(O)$R^b$, C(O)OR$^a$, OC(O)$R^b$, SO$_2$NR$^a$R$^a$, NR$^a$SO$_2$$R^b$, NR$^a$C(O)OR$^b$, OC(O)NR$^a$R$^a$, NR$^a$C(O)NR$^a$R$^a$, thioxo, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)$R^b$, SO$_2$$R^b$, C(O)$R^b$, C(O)NR$^a$R$^a$, NR$^a$C(O)$R^b$, C(O)OR$^a$, OC(O)$R^b$, NR$^a$SO$_2$$R^b$, SO$_2$NR$^a$R$^a$, NR$^a$C(O)OR$^b$, OC(O)NR$^a$R$^a$ or NR$^a$C(O)NR$^a$R$^a$.

According to an alternative aspect of the invention R$^1$ is as for any aspect, claim or embodiment hereinbefore or hereinafter, R$^2$ is unsubstituted phenyl, and R$^3$ represents T which optionally is substituted on the aromatic ring by one or more of the following independently selected from: halogen (Cl, F, I, Br), OH, CN, NO$_2$, NR$^a$R$^a$, OR$^b$, SR$^b$, SiR$^b$R$^b$R$^b$, S(O)$R^b$, SO$_2$$R^b$, C(O)$R^b$, phenylC$_1$alkyl, C(O)NR$^a$R$^a$, NR$^a$C(O)$R^b$, C(O)OR$^a$, OC(O)$R^b$, SO$_2$NR$^a$R$^a$, NR$^a$SO$_2$$R^b$, NR$^a$C(O)OR$^b$, OC(O)NR$^a$R$^a$, OSO$_2$$R^b$, NR$^a$-C(O)NR$^a$R$^a$, SO$_2$NHC(O)$R^b$, Q, Het$^2$, R, Het$^3$, QZ, Het$^2$Z, RZ, Het$^3$Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)$R^b$, SO$_2$$R^b$, C(O)$R^b$, C(O)NR$^a$R$^a$, NR$^a$C(O)$R^b$, C(O)OR$^a$, OC(O)$R^b$, NR$^a$SO$_2$$R^b$, SO$_2$NR$^a$R$^a$, NR$^a$C(O)OR$^b$, OC(O)NR$^a$R$^a$ or NR$^a$C(O)NR$^a$R$^a$, and wherein T optionally is substituted on the non-aromatic ring by one or more of the following independently selected from: F, OH, CN, NR$^a$R$^a$, OR$^b$, SR$^b$, SiR$^b$R$^b$R$^b$, S(O)$R^b$, SO$_2$$R^b$, C(O)$R^b$, phenylC$_1$alkyl, C(O)NR$^a$R$^a$, NR$^a$C(O)$R^b$, C(O)OR$^a$, OC(O)$R^b$, SO$_2$NR$^a$R$^a$, NR$^a$SO$_2$$R^b$, NR$^a$C(O)OR$^b$, OC(O)NR$^a$R$^a$, NR$^a$C(O)NR$^a$R$^a$, thioxo, Q, Het$^2$, R, Het$^3$, QZ, Het$^2$Z, RZ, Het$^3$Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)$R^b$, SO$_2$$R^b$, C(O)$R^b$, C(O)NR$^a$R$^a$, NR$^a$C(O)$R^b$, C(O)OR$^a$, OC(O)$R^b$, NR$^a$SO$_2$$R^b$, SO$_2$NR$^a$R$^a$, NR$^a$C(O)OR$^b$, OC(O)NR$^a$R$^a$ or NR$^a$C(O)NR$^a$R$^a$.

According to an alternative aspect of the invention R$^1$ is as for any aspect, claim or embodiment hereinbefore or hereinafter, R$^2$ is unsubstituted phenyl, and R$^3$ represents T which optionally is substituted on the aromatic ring by one or more of the following independently selected from: halogen (Cl, F, I, Br), OH, CN, NO$_2$, NR$^a$R$^a$, OR$^b$, SR$^b$, SiR$^b$R$^b$R$^b$, S(O)$R^b$, SO$_2$$R^b$, C(O)$R^b$, phenylC$_1$alkyl, C(O)NR$^a$R$^a$, NR$^a$C(O)$R^b$, C(O)OR$^a$, OC(O)$R^b$, SO$_2$NR$^a$R$^a$, NR$^a$SO$_2$$R^b$, NR$^a$C(O)OR$^b$, OC(O)NR$^a$R$^a$, OSO$_2$$R^b$NR$^a$C(O)OR$^a$, SO$_2$NHC(O)$R^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)$R^b$, SO$_2$$R^b$, C(O)$R^b$, C(O)NR$^a$R$^a$, NR$^a$C(O)$R^b$, C(O)OR$^a$, OC(O)$R^b$, NR$^a$SO$_2$$R^b$, SO$_2$NR$^a$R$^a$, NR$^a$C(O)OR$^b$, OC(O)NR$^a$R$^a$ or NR$^a$C(O)NR$^a$R$^a$, and wherein T optionally is substituted on the non-aromatic ring by one or more of the following independently selected from: F, OH, CN, NR$^a$R$^a$, OR$^b$, SR$^b$, SiR$^b$R$^b$R$^b$, S(O)$R^b$, SO$_2$$R^b$, C(O)$R^b$, phenylC$_1$alkyl, C(O)N$^a$R$^a$, NR$^a$C(O)$R^b$, C(O)OR$^a$, OC(O)$R^b$, SO$_2$NR$^a$R$^a$, NR$^a$SO$_2$$R^b$, NR$^a$C(O)OR$^b$, OC(O)NR$^a$R$^a$, NR$^a$C(O)NR$^a$R$^a$, thioxo, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)$R^b$, SO$_2$$R^b$, C(O)$R^b$, C(O)NR$^a$R$^a$, NR$^a$C(O)$R^b$, C(O)OR$^a$, OC(O)$R^b$, NR$^a$SO$_2$$R^b$, SO$_2$NR$^a$R$^a$, NR$^a$C(O)OR$^b$, OC(O)NR$^a$R$^a$ or NR$^a$C(O)NR$^a$R$^a$.

The above aspects may be combined with any other aspects, embodiments or claims hereinbefore or hereinafter.

According to an alternative embodiment of the invention R$^1$ is selected from methyl, tert-butyl, 2-methoxyethyl, 4-(difluoromethoxy)benzyl or (6-aminopyridin-3-yl)methyl, R$^2$ is selected from phenyl, p-chlorophenyl or m-chlorophenyl, and R$^3$ is selected from 4-(difluoromethoxy)phenyl, 4-methoxyphenyl, 4-hydroxyphenyl, 4-isopropoxyphenyl, 4-[(tert-butoxycarbonyl)amino]phenyl, 4-(hydroxymethyl)phenyl, 4-(benzyloxy)phenyl, 4-fluorophenyl or 4-[(acetylamino)sulfonyl]phenyl.

According to an alternative embodiment of the invention R$^1$ is selected from methyl, ethyl, isopropyl, n-butyl, tert-butyl, 2-methoxyethyl, 4-(difluoromethoxy)benzyl or (6-aminopyridin-3-yl)methyl, R$^2$ is selected from phenyl, p-chlorophenyl or m-chlorophenyl, and R$^3$ is selected from 4-morpholin-4-ylphenyl, 3-chloro-4-morpholin-4-ylphenyl, 2,5-diethoxy-4-morpholin-4-ylphenyl, 4-pyrrolidin-1- ylphenyl, 4-piperidin-1-ylphenyl, 4-azepan-1-ylphenyl or 4-(4-benzylpiperazin-1-yl)phenyl.

According to an alternative embodiment of the invention $R^1$ is selected from methyl, ethyl, n-butyl or 2-methoxyethyl, $R^2$ is selected from phenyl or 4-(trifluoromethyl)phenyl, and $R^3$ is selected from 2-acetyl-1-benzofuran-5-yl, 1-benzofuran-5-yl, 2-(dimethylamino)-1-benzofuran-5-yl, 2-carboxy-1-benzofuran-5-yl, 2-(tert-butoxycarbonyl)-1-benzofuran-5-yl, 1H-indol-5-yl, 1H-benzimidazol-5-yl, 2-(ethoxycarbonyl)-3-methyl-1-benzothien-5-yl, 2-thioxo-2,3-dihydro-1,3-benzothiazol-6-yl, 1,3-dioxo-2,3-dihydro-1H-isoindol-5-yl, 1,2,3,4-tetrahydroisoquinolin-6-yl, 2-(tert-butoxycarbonyl)-1,2,3,4-tetrahydroisoquinolin-6-yl or 2-acetyl-1,2,3,4-tetrahydroisoquinolin-6-yl.

The above aspects may be combined with any other aspects, embodiments or claims hereinbefore or hereinafter.

In a further aspect of the invention there is provided a compound of general formula (V), (VI), (IX) or (X)

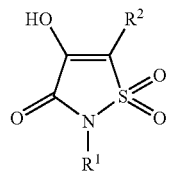
(V)

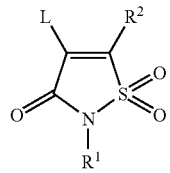
(VI)

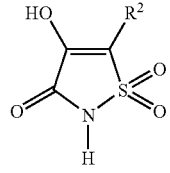
(IX)

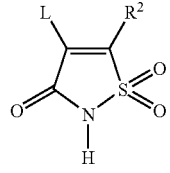
(X)

or a pharmaceutically acceptable salt thereof,
wherein $R^1$ is defined as for any aspects, embodiments or claims hereinbefore or hereinafter, $R^2$ is defined as for any aspects, embodiments or claims hereinbefore or hereinafter, and L is a suitable leaving group such as Cl, Br, I, p-toluensulfonate, methanesulfonate or trifluoromethanesulfonate, with the proviso that the following compounds are excluded: 4-hydroxy-5-phenylisothiazol-3(2H)-one 1,1-dioxide, 5-(4-aminophenyl)-4-hydroxy-2-methyl-isothiazol-3(2H)-one 1,1-dioxide, 4-hydroxy-2-methyl-5-(4-nitrophenyl)isothiazol-3(2H)-one 1,1-dioxide, 4-hydroxy-2-methyl-5-phenylisothiazol-3(2H)-one 1,1-dioxide, 5-(3,4-dichlorophenyl)-4-hydroxyisothiazol-3(2H)-one 1,1-dioxide, 2-benzyl-4-hydroxy-5-phenylisothiazol-3(2H)-one 1,1-dioxide, and 4-hydroxy-2-(4-methylphenyl)-5-phenylisothiazol-3(2H)-one 1,1-dioxide.

Certain compounds of the present invention may exist as tautomers or stereoisomers (e.g. racemate, enantiomer, diastereomer or E- or Z-isomer). It is to be understood that the present invention encompasses all such tautomers and stereoisomers.

Certain compounds of the present invention may exist as solvates or hydrates. It is to be understood that the present invention encompasses all such solvates or hydrates.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, nitric, methanesulphonic, sulphuric, phosphoric, trifluoroacetic, para-toluene sulfonic, 2-mesitylen sulfonic, citric, acetic, tartaric, fumaric, lactic, succinic, malic, malonic, maleic, 1,2-ethanedisulphonic, adipic, aspartic, benzenesulphonic, benzoic, ethanesulphonic or nicotinic acid. In addition a suitable pharmaceutically acceptable salt of a compound of the invention, is, for example, a base-addition salt of a compound of the invention which is sufficiently acidic, for example, a metal salt, for example, sodium, potassium, calcium, magnesium, zinc or aluminum, an ammonium salt, a salt with an organic base which affords a physiologically acceptable cation, which includes quartenery ammonium hydroxides, for example methylamine, ethylamine, diethylamine, trimethylamine, tert-butylamine, triethylamine, dibenzylamine, N,N-dibenzylethylamine, cyclohexylethylamine, tris-(2-hydroxyethyl)amine, hydroxyethyl diethylamine, (1R,2S)-2-hydroxyinden-1-amine, morpholine, N-methylpiperidine, N-ethylpiperidine, piperazine, methylpiperazine, adamantylamine, choline hydroxide, tetrabutylammonium hydroxide, tris-(hydroxymethyl)methylamine hydroxide, L-arginine, N-methyl D-glucamine, lysine or arginine.

The compound of the formula (I), or other compounds disclosed herein, may be administered in the form of a pro-drug which is broken down in the human or animal body to give a compound of the formula (I). Examples of pro-drugs include in vivo hydrolysable esters and in vivo hydrolysable amides of a compound of the formula (I).

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

Methods of Preparation

The compounds of the invention may be prepared as outlined in the Schemes below. However, the invention is not limited to these methods. The compounds may also be prepared as described for structurally related compounds in the prior art. The reactions can be carried out according to standard procedures or as described in the experimental section.

In the Schemes below the term "reagent" means a reagent that can transform a hydroxy group into a leaving group L. Examples of such leaving groups are for instance Cl, Br, I, methanesulfonate (OMs), p-toluensulfonate or trifluoromethanesulfonate (OTf). Furthermore, in all Schemes below $R^1$, $R^2$ and $R^3$ are as defined for any aspects, embodiments or claims hereinbefore or hereinafter.

Schemes I-VI illustrate different processes for synthesizing compounds of formula (I).

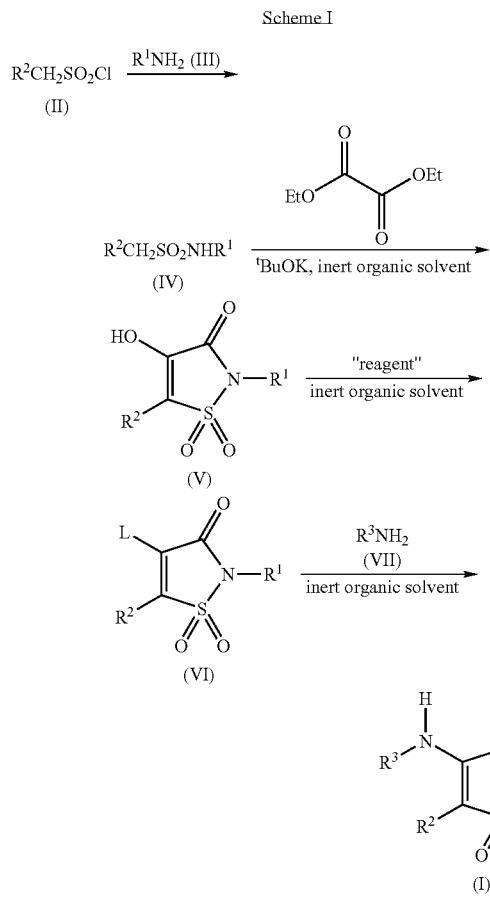

Scheme I describes a method of preparation of compounds according to formula (I), wherein $R^1$, $R^2$ and $R^3$ are as defined for any aspects or embodiments hereinbefore or hereinafter, and L is a leaving group such as for instance Cl, Br, I, p-toluensulfonate, methanesulfonate or trifluoromethanesulfonate, comprising the following steps:

a) A process for the preparation of a compound according to formula (I) comprising the step of reacting a compound of formula (VI)

with a compound of formula (VII)

$R^3NH_2$ (VII)

optionally in the presence of an inert organic solvent such as dimethylformamide.

b) A process for the preparation of a compound according to formula (VI)

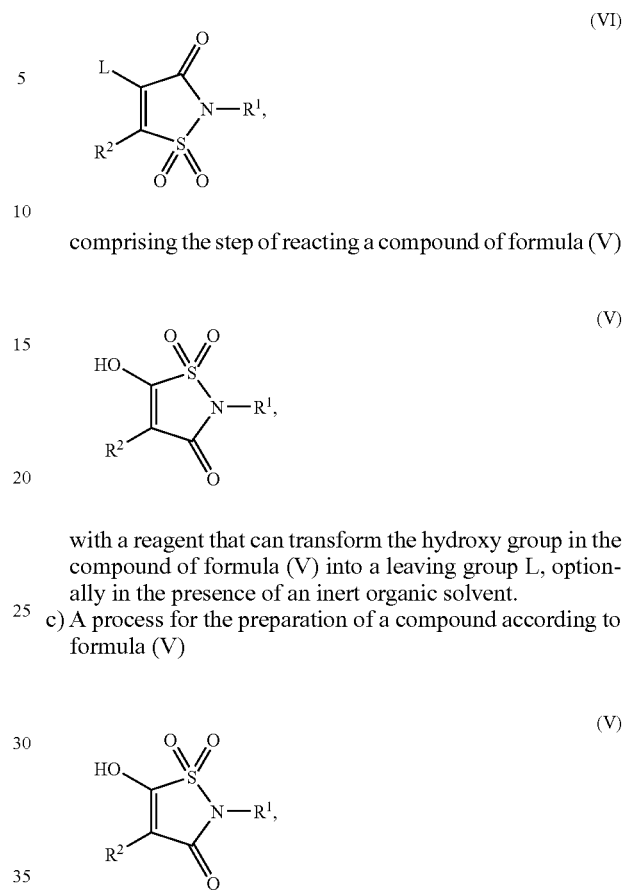

comprising the step of reacting a compound of formula (V)

with a reagent that can transform the hydroxy group in the compound of formula (V) into a leaving group L, optionally in the presence of an inert organic solvent.

c) A process for the preparation of a compound according to formula (V)

comprising the step of reacting a compound of formula (IV)

$R^2CH_2SO_2NHR^1$ (IV)

with diethyl oxalate, or a suitable equivalent thereof, in the presence of a base such as for instance potassium tert-butoxide, optionally in the presence of an inert organic solvent such as THF.

d) A process for the preparation of a compound according to formula (IV)

$R^2CH_2SO_2NHR^1$ (IV), comprising the step of reacting a compound of formula (II)

$R^2CH_2SO_2Cl$ (II)

with a compound of formula (III)

$R^1NH_2$ (III), optionally in the presence of a base and an inert organic solvent.

Scheme II

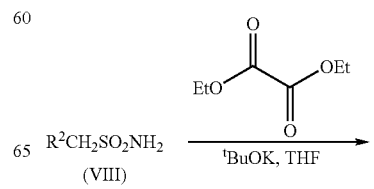

-continued

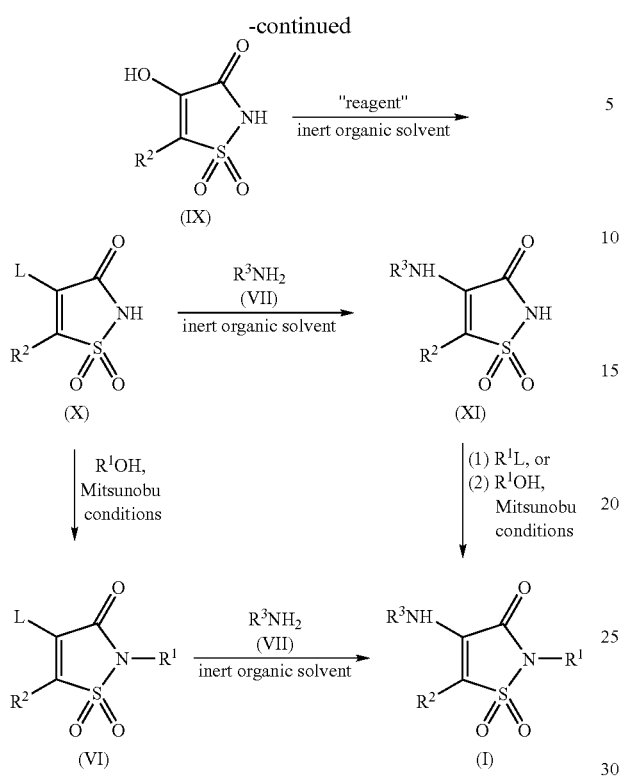

Scheme II describes a method of preparation of compounds according to formula (I), wherein $R^1$, $R^2$ and $R^3$ are as defined for any aspects or embodiments hereinbefore or hereinafter, and L is a leaving group such as for example Cl, Br, I, p-toluensulfonate, methanesulfonate or trifluoromethanesulfonate, comprising the following steps:

a) A process for the preparation of a compound according to formula (I) comprising the step of reacting
(i) a compound of formula (VI)

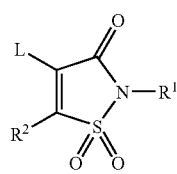
(VI)

with a compound of formula (VII)

$R^3NH_2$ (VII)

optionally in the presence of an inert organic solvent such as dimethylformamide; or
(ii) a compound of formula (XI)

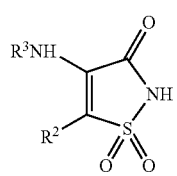
(XI)

either with $R^1OH$ using Mitsunobu conditions or with an alkylating agent such as $R^1L$.

b) A process for the preparation of a compound according to formula (VI)

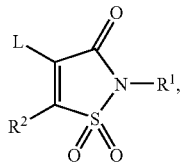
(VI)

comprising the step of reacting a compound of formula (X)

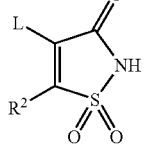
(X)

with $R^1OH$ using Mitsunobu conditions.

c) A process for the preparation of a compound according to formula (XI)

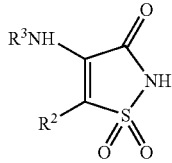
(XI)

comprising the step of reacting a compound of formula (X)

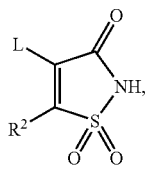
(X)

with a compound of formula (VII)

$R^3NH_2$ (VII), optionally in the presence of an inert organic solvent.

d) A process for the preparation of a compound according to formula (X)

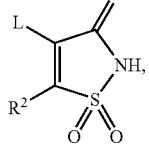
(X)

comprising the step of reacting a compound of formula (IX)

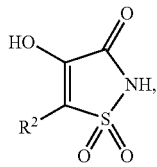
(IX)

with a reagent that transforms the hydroxy group in the compound of Formula (IX) into a leaving group L.

e) A process for the preparation of a compound of formula (IX)

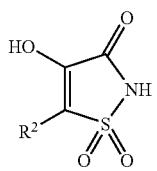
(IX)

comprising the step of reacting a compound of formula (VIII)

$R^2CH_2SO_2NH_2$ (VIII)

with diethyl oxalate, or a suitable equivalent thereof, in the presence of a base such as for instance potassium tert-butoxide, optionally in the presence of an inert organic solvent such as THF.

In Scheme III $R^2X$ is an aryl halide, wherein $R^2$ is defined as for any aspects, embodiments or claims hereinbefore or hereinafter. Furthermore, in Schemes III, IV and V $R^2(OR')_2$ is a reagent wherein $R^2$ is defined as for any aspects, embodiments or claims hereinbefore or hereinafter and R' is a hydrocarbon.

Scheme IV

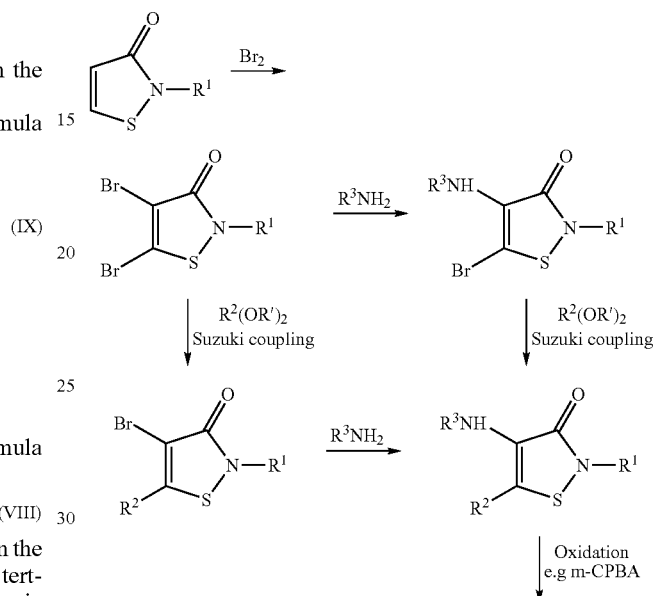

Scheme III

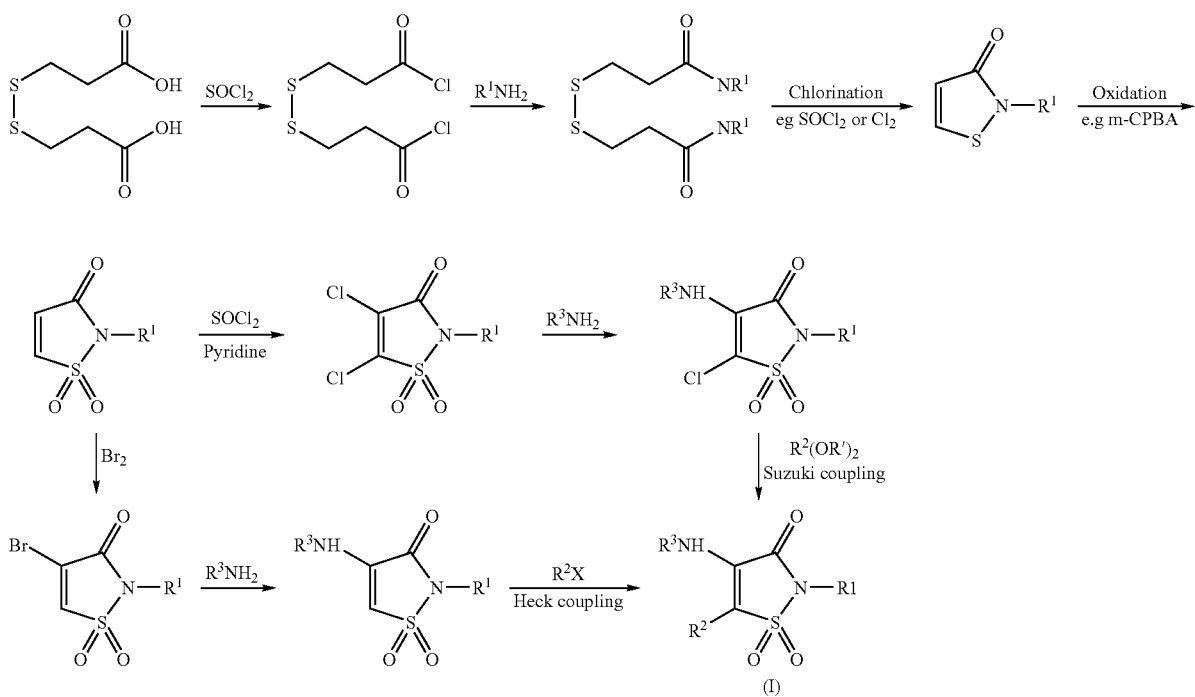

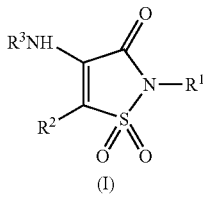

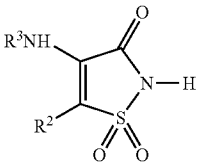

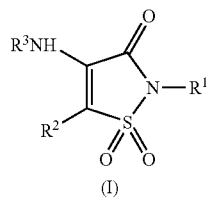

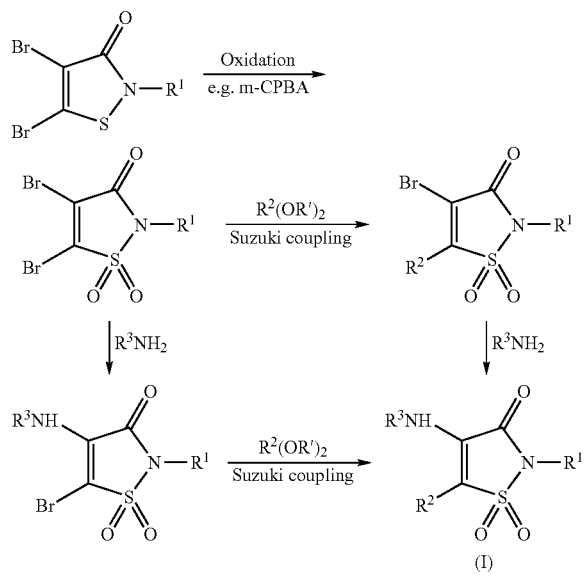

The expression "inert organic solvent" refers to a solvent which does not react with the starting materials, reagents, intermediates or products in a manner which adversely affects the yield of the desired product. Examples of such solvents are dimethylformamide, methylene chloride and acetonitrile.

The individual reactions steps in Schemes I-V may be performed while heating either using conventional means such as heating the reaction mixture on an oil bath, or heating the reaction mixture in a microwave oven.

Furthermore, it shall be understood that the $R^1$ group in a compound of formula (I) can be replaced by another $R^1$ group, e.g. cyclopentyl. For example, when $R^1$ is tert-butyl it can be removed by deprotection with trifluoroacetic acid, and the resulting compound can subsequently be reacted with an alkylating agent containing the new $R^1$ group. This is illustrated in Scheme VI, where PG denotes a protecting group.

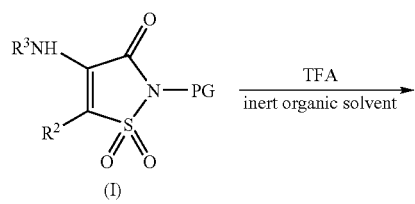

It shall be understood that in some of the reactions in this application it may be necessary to use protecting group for functionalities such as for example hydroxyl groups, amino groups, and carboxyl. groups Further representative protecting groups can be found in T. W. Green and P. G. M. Wuts, Protective Groups in Organic Synthesis, $3^{rd}$ Ed., Wiley and Sons, Inc., New York (1999), which is incorporated hereby by reference in its entirety.

It shall be understood that the diethyl oxalate used in the Schemes above can be exchanged for equivalent reagents such as e.g. methyl oxalyl chloride.

It shall be understood thst the potassium tert-butoxide used in the Schemes above can be exchanged for equivalent reagents such as e.g. lithium tert-butoxide.

Compounds of formula (II) and (IV) are commercially available or may be prepared as described in the experimental part in this patent application or by methods known by those skilled in the art.

Compounds of formula (VII) are commercially available or may be prepared as described in the experimental part in this patent application or by methods known by those skilled in the art.

Certain compounds of formula (V), (VI), (IX) or (X) are believed to be novel and are claimed herein as useful intermediates in the preparation of compounds of formula (I).). All intermediates are commercially available or may may be prepared as described in the experimental part in this patent application or by methods known by those skilled in the art. Furthermore, the intermediates may be prepared in an analogous way to the procedures described in the experimental part in this patent application.

It is to be understood that when $R^1$ or $R^3$ represent nitrogen oxides in compounds of formula I these are prepared from the corresponding amines and an oxidizing agent such as metachloroperbenzoic acid (MCPBA) optionally in the presence of an inert organic solvent such as dichloromethane.

Persons skilled in the art will appreciate that, in order to obtain compounds of the invention in an alternative and in some occasions, more convenient manner, the individual process steps mentioned hereinbefore may be performed in a different order, and/or the individual reactions may be performed at different stage in the overall route (i.e. chemical transformations may be performed upon different intermediates to those associated hereinbefore with a particular reaction).

Pharmaceutical Preparations

The compounds of the invention will normally be administered via the oral, parenteral, intravenous, intramuscular, subcutaneous or in other injectable ways, buccal, rectal, vaginal, transdermal and/or nasal route and/or via inhalation, in the form of pharmaceutical preparations comprising the active ingredient or a pharmaceutically acceptable salt or solvate thereof, or a solvate of such a salt, in a pharmaceutically acceptable dosage form. Depending upon the disorder and patient to be treated and the route of administration, the compositions may be administered at varying doses.

Suitable daily doses of the compounds of the invention in therapeutical treatment of humans are about 0.0001-100 mg/kg body weight, preferably 0.01-10 mg/kg body weight.

Oral formulations are preferred particularly tablets or capsules which may be formulated by methods known to those skilled in the art to provide doses of the active compound in the range of 0.007 mg to 700 mg for example 1 mg, 3 mg, 5 mg, 10 mg, 25 mg, 50 mg, 100 mg and 250 mg.

According to a further aspect of the invention there is thus provided a pharmaceutical formulation including any of the compounds of the invention, or pharmaceutically acceptable derivatives thereof, in admixture with pharmaceutically acceptable excipients, oils which may be glycerides, diluents and/or carriers.

Pharmacological Properties

The compounds of formula (I) are useful for normalization of cholesterol homeostasis, decreasing intestinal cholesterol absorption, improving reverse cholesterol transport, improving HDL functionality, increasing HDL-cholesterol levels, decreasing LDL-cholesterol levels, decreasing cholesterol content of apoB-containing lipoproteins, stimulating cholesterol efflux from vascular cells and/or decreasing the inflammatory response of vascular cells. As a consequence of these properties the compounds of formula (I) are expected to have anti-atherosclerotic effects.

The compounds of formula (I) are useful in the prevention or treatment of cardiovascular disease in a mammal, particularly a human. The compounds of formula (I) are useful in the prevention or treatment of atherosclerosis in a mammal, particularly a human. Cardiovascular disease includes but is not limited to conditions associated with atherosclerosis, arteriosclerosis, hypercholesterolemia, and other kinds of dyslipidemia that increase the risk for cardiovascular disease. In particular the compounds of formula (I) are useful in the treatment or prevention of cardiovascular disease, especially those involving atherosclerosis, hypercholesterolemia and dyslipidemia.

The compounds of formula (I) also serve to prevent lipid accumulation in, or remove lipids from, tissue deposits such as atherosclerotic plaques or xanthomas in a patient with atherosclerotic disease manifest by clinical signs such as angina, claudication, bruits, one that has suffered a mycardial infarction, stroke or transient ischemic attack, or one diagnosed by angiography, sonography or MRI.

The compounds of formula (I) also serve to prevent or reduce the risk of developing atherosclerosis, as well as for halting or slowing the progression of atherosclerotic disease once it has become clinically evident, comprising the administration of a prophylactically or therapeutically effective amount, as appropriate, of a compound of formula (I) to a mammal, including a human, who is at risk of developing atherosclerosis or who already has atherosclerotic disease.

Atherosclerosis encompasses vascular diseases and conditions that are recognized and understood by physicians practicing in the relevant fields of medicine. Atherosclerotic cardiovascular disease including restenosis following revascularization procedures, coronary heart disease (also known as coronary artery disease or ischemic heart disease), cerebrovascular disease including multi-infarct dementia, and peripheral vessel disease including erectile dysfunction are all clinical manifestations of atherosclerosis and are therefore encompassed by the terms "atherosclerosis" and "atherosclerotic disease".

The present compounds of formula (I) are also useful for the prophylaxis and/or treatment of clinical conditions associated with atherosclerosis such as inherited or induced hypercholesterolemia as well as inherited or induced reduced sensitivity to insulin (insulin resistance syndrome also known as metabolic syndrome) and associated metabolic disorders. These clinical conditions will include, but will not be limited to, general obesity, abdominal obesity, arterial hypertension, hyperinsulinaemia, type 2 diabetes, type 1 diabetes and other more rare forms of diabetes mellitus and the dyslipidaemia characteristically appearing with insulin resistance. This dyslipidaemia, also known as the atherogenic lipoprotein profile, is characterised by moderately elevated non-esterified fatty acids, elevated VLDL triglyceride rich particles, high ApoB levels, low HDL levels associated with low apoAI levels in the presence of small, dense, LDL particles, phenotype B.

The compounds of formula (I) are expected to be useful in treating patients with combined or mixed hyperlipidemias and dyslipidemias, especially low HDL levels with or without other manifestations of the metabolic syndrome.

The compounds of formula (I) are expected to be useful in treating patients with low HDL levels of other reasons than metabolic syndrome or type 2 diabetes.

Treatment with the compounds of formula (I) are expected to lower the cardiovascular morbidity and mortality associated with atherosclerosis due to their antidyslipidaemic as well as antiinflammatory properties. The cardiovascular disease conditions include macro-angiopathies of various internal organs causing myocardial infarction, congestive heart failure, cerebrovascular disease and peripheral arterial insufficiency. The insulin sensitizing effect of the compounds of formula (I) is also expected to prevent or delay the development of type 2 diabetes from the metabolic syndrome and diabetes of pregnancy. Therefore the development of long-term complications associated with chronic hyperglycaemia in diabetes mellitus such as the micro-angiopathies causing renal disease, retinal damage and peripheral vascular disease of the lower limbs are expected to be delayed.

The compounds of formula (I) may also be useful for the prevention or treatment of inflammation and neurodegenerative diseases or neurological disorders. Accordingly, this invention also provides a method for preventing or treating inflammation in the CNS, reducing amyloid pathology and a method for preventing or treating neurodegenerative diseases or disorders characterized by neuron degeneration, neuron injury or impaired plasticity or inflammation in the CNS. The neurodegenerative diseases or conditions characterized by neuron degeneration and inflammation will include but will not be limited to stroke, Alzheimer's disease, fronto-temporal dementias (taupathies), peripheral neuropathy, Parkinson's disease, dementia with Lewy bodies, Huntington's disease, amyotrophic lateral sclerosis and multiple sclerosis.

The compounds of formula (I) are useful in preventing or treating inflammatory conditions or diseases. These diseases or conditions will include but will not be limited to atherosclerotic diseases such as angina pectoris and myocardial infarction but also rheumatoid arthristis, juvenile rheumatoid arthritis, systemic lupus erythematosus, osteoarthritis, degenerative joint disease, one or more connective tissue diseases, ankylosing spondolytis, bursitis, Sjogren's syndrome, psoriasis, psoriatic arthritis, neuraligia, synovitis, glomerulonephritis, vasculitis or sarcoidosis as well as inflammatory bowel diseases such as Coeliac disease, proctitis, eosinopilic gastroenteritis, mastocytosis, Crohn's disease, ulcerative colitis, microscopic colitis, indeterminant colitis, irritable bowel disorder, irritable bowel syndrome and distal proctitis. Compounds of formula (I) may also be used in other inflammatory conditions of the lung including asthma, adult respiratory distress syndrome, chronic obstructive pulmonary disease and pneumonia bronchitis.

Furthermore the compounds of formula (I) may be useful in treatment of various conditions outside the cardiovascular system whether or not associated with insulin resistance, like polycystic ovarian syndrome, obesity and cancer.

The present invention provides a method of treating and/or preventing rheumatoid arthritis comprising the administration of an effective amount of a compound of formula (I) to a mammal (particularly a human) in need thereof.

The present invention provides a method of treating and/or preventing juvenile rheumatoid arthritis comprising the administration of an effective amount of a compound of formula (I) to a mammal (particularly a human) in need thereof.

The present invention provides a method of treating and/or preventing systemic lupus erythematosus comprising the administration of an effective amount of a compound of formula (I) to a mammal (particularly a human) in need thereof.

The present invention provides a method of treating and/or preventing osteoarthritis comprising the administration of an effective amount of a compound of formula (I) to a mammal (particularly a human) in need thereof.

The present invention provides a method of treating and/or preventing degenerative joint disease comprising the administration of an effective amount of a compound of formula (I) to a mammal (particularly a human) in need thereof.

The present invention provides a method of treating and/or preventing one or more connective tissue diseases comprising the administration of an effective amount of a compound of formula (I) to a mammal (particularly a human) in need thereof.

The present invention provides a method of treating and/or preventing ankylosing spondolytis comprising the administration of an effective amount of a compound of formula (I) to a mammal (particularly a human) in need thereof.

The present invention provides a method of treating and/or preventing bursitis comprising the administration of an effective amount of a compound of formula (I) to a mammal (particularly a human) in need thereof.

The present invention provides a method of treating and/or preventing Sjogren's syndrome comprising the administration of an effective amount of a compound of formula (I) to a mammal (particularly a human) in need thereof.

The present invention provides a method of treating and/or preventing psoriasis comprising the administration of an effective amount of a compound of formula (I) to a mammal (particularly a human) in need thereof.

The present invention provides a method of treating and/or preventing psoriatic arthritis comprising the administration of an effective amount of a compound of formula (I) to a mammal (particularly a human) in need thereof.

The present invention provides a method of treating and/or preventing neuraligia comprising the administration of an effective amount of a compound of formula (I) to a mammal (particularly a human) in need thereof.

The present invention provides a method of treating and/or preventing synovitis comprising the administration of an effective amount of a compound of formula (I) to a mammal (particularly a human) in need thereof.

The present invention provides a method of treating and/or preventing glomerulonephritis comprising the administration of an effective amount of a compound of formula (I) to a mammal (particularly a human) in need thereof.

The present invention provides a method of treating and/or preventing vasculitis or sarcoidosis comprising the administration of an effective amount of a compound of formula (I) to a mammal (particularly a human) in need thereof.

The present invention provides a method of treating and/or preventing inflammatory bowel disease comprising the administration of an effective amount of a compound of formula (I) to a mammal (particularly a human) in need thereof.

The present invention provides a method of treating and/or preventing Crohn's disease comprising the administration of an effective amount of a compound of formula (I) to a mammal (particularly a human) in need thereof.

The present invention provides a method of treating and/or preventing ulcerative colitis comprising the administration of an effective amount of a compound of formula (I) to a mammal (particularly a human) in need thereof.

The present invention provides a method of treating and/or preventing Coeliac disease comprising the administration of an effective amount of a compound of formula (I) to a mammal (particularly a human) in need thereof.

The present invention provides a method of treating and/or preventing proctitis comprising the administration of an effective amount of a compound of formula (I) to a mammal (particularly a human) in need thereof.

The present invention provides a method of treating and/or preventing eosinopilic gastro-enteritis comprising the administration of an effective amount of a compound of formula (I) to a mammal (particularly a human) in need thereof.

The present invention provides a method of treating and/or preventing mastocytosis comprising the administration of an effective amount of a compound of formula (I) to a mammal (particularly a human) in need thereof.

The present invention provides a method of treating and/or preventing microscopic colitis comprising the administration of an effective amount of a compound of formula (I) to a mammal (particularly a human) in need thereof.

The present invention provides a method of treating and/or preventing indeterminant colitis comprising the administration of an effective amount of a compound of formula (I) to a mammal (particularly a human) in need thereof.

The present invention provides a method of treating and/or preventing irritable bowel disorder comprising the administration of an effective amount of a compound of formula (I) to a mammal (particularly a human) in need thereof.

The present invention provides a method of treating and/or preventing irritable bowel syndrome comprising the administration of an effective amount of a compound of formula (I) to a mammal (particularly a human) in need thereof.

The present invention provides a method of treating and/or preventing the insulin resistance syndrome and/or metabolic disorders (as defined above) comprising the administration of a compound of formula (I) to a mammal (particularly a human) in need thereof.

The present invention provides a method of treating and/or preventing type 2 diabetes comprising the administration of an effective amount of a compound of formula (I) to a mammal (particularly a human) in need thereof.

The present invention provides a method of treating and/or preventing cardiovascular disease comprising the administration of an effective amount of a compound of formula (I) to a mammal (particularly a human) in need thereof.

The present invention provides a method of treating and/or preventing atherosclerosis comprising the administration of an effective amount of a compound of formula (I) to a mammal (particularly a human) in need thereof.

The present invention provides a method of treating and/or preventing hypercholesterolemia comprising the administration of an effective amount of a compound of formula (I) to a mammal (particularly a human) in need thereof.

The present invention provides a method of treating and/or preventing conditions associated with a need for improving reverse cholesterol transport comprising the administration of an effective amount of a compound of formula (I) to a mammal (particularly a human) in need thereof.

The present invention provides a method of treating and/or preventing conditions associated with a need for decreasing intestinal cholesterol absorption comprising the administration of an effective amount of a compound of formula (I) to a mammal (particularly a human) in need thereof.

The present invention provides a method of treating and/or preventing conditions associated with a need for increasing HDL-cholesterol levels comprising the administration of an effective amount of a compound of formula (I) to a mammal (particularly a human) in need thereof.

The present invention provides a method of treating and/or preventing conditions associated with a need for decreasing LDL-cholesterol levels comprising the administration of an effective amount of a compound of formula (I) to a mammal (particularly a human) in need thereof.

The present invention provides a method of treating and/or preventing inflammatory conditions comprising the administration of an effective amount of a compound of formula (I) to a mammal (particularly a human) in need thereof.

The present invention provides a method of treating and/or preventing Alzheimer's disease comprising the administration of an effective amount of a compound of formula (I) to a mammal (particularly a human) in need thereof.

The present invention provides a method of treating and/or preventing arteriosclerosis comprising the administration of an effective amount of a compound of formula (I) to a mammal (particularly a human) in need thereof.

The present invention provides a method of treating and/or preventing conditions associated with a need for improving HDL function comprising the administration of an effective amount of a compound of formula (I) to a mammal (particularly a human) in need thereof.

The present invention provides a method of treating and/or preventing hyperlipidemic conditions comprising the administration of an effective amount of a compound of formula (I) to a mammal (particularly a human) in need thereof.

The present invention provides a method of treating and/or preventing dyslipidemic conditions comprising the administration of an effective amount of a compound of formula (I) to a mammal (particularly a human) in need thereof.

The present invention provides a method of treating and/or preventing dyslipidemia comprising the administration of an effective amount of a compound of formula (I) to a mammal (particularly a human) in need thereof.

In a further aspect the present invention provides the use of a compound of formula (I) as a medicament.

In a further aspect the present invention provides the use of a compound of formula (I) in the manufacture of a medicament for the treatment and/or prohylaxis of rheumatoid arthritis.

In a further aspect the present invention provides the use of a compound of formula (I) in the manufacture of a medicament for the treatment and/or prohylaxis of juvenile rheumatoid arthritis.

In a further aspect the present invention provides the use of a compound of formula (I) in the manufacture of a medicament for the treatment and/or prohylaxis of systemic lupus erythematosus.

In a further aspect the present invention provides the use of a compound of formula (I) in the manufacture of a medicament for the treatment and/or prohylaxis of osteoarthritis.

In a further aspect the present invention provides the use of a compound of formula (I) in the manufacture of a medicament for the treatment and/or prohylaxis of degenerative joint disease.

In a further aspect the present invention provides the use of a compound of formula (I) in the manufacture of a medicament for the treatment and/or prohylaxis of one or more connective tissue diseases.

In a further aspect the present invention provides the use of a compound of formula (I) in the manufacture of a medicament for the treatment and/or prohylaxis of ankylosing spondolytis.

In a further aspect the present invention provides the use of a compound of formula (I) in the manufacture of a medicament for the treatment and/or prohylaxis of bursitis.

In a further aspect the present invention provides the use of a compound of formula (I) in the manufacture of a medicament for the treatment and/or prohylaxis of Sjogren's syndrome.

In a further aspect the present invention provides the use of a compound of formula (I) in the manufacture of a medicament for the treatment and/or prohylaxis of psoriasis.

In a further aspect the present invention provides the use of a compound of formula (I) in the manufacture of a medicament for the treatment and/or prohylaxis of psoriatic arthritis.

In a further aspect the present invention provides the use of a compound of formula (I) in the manufacture of a medicament for the treatment and/or prohylaxis of neuraligia.

In a further aspect the present invention provides the use of a compound of formula (I) in the manufacture of a medicament for the treatment and/or prohylaxis of synovitis.

In a further aspect the present invention provides the use of a compound of formula (I) in the manufacture of a medicament for the treatment and/or prohylaxis of glomerulonephritis.

In a further aspect the present invention provides the use of a compound of formula (I) in the manufacture of a medicament for the treatment and/or prohylaxis of vasculitis or sarcoidosis.

In a further aspect the present invention provides the use of a compound of formula (I) in the manufacture of a medicament for the treatment and/or prohylaxis of inflammatory bowel disease.

In a further aspect the present invention provides the use of a compound of formula (I) in the manufacture of a medicament for the treatment and/or prohylaxis of Crohn's disease.

In a further aspect the present invention provides the use of a compound of formula (I) in the manufacture of a medicament for the treatment and/or prohylaxis of ulcerative colitis.

In a further aspect the present invention provides the use of a compound of formula (I) in the manufacture of a medicament for the treatment and/or prohylaxis of Coeliac disease.

In a further aspect the present invention provides the use of a compound of formula (I) in the manufacture of a medicament for the treatment and/or prohylaxis of proctitis.

In a further aspect the present invention provides the use of a compound of formula (I) in the manufacture of a medicament for the treatment and/or prohylaxis of eosinopilic gastro-enteritis.

In a further aspect the present invention provides the use of a compound of formula (I) in the manufacture of a medicament for the treatment and/or prohylaxis of mastocytosis.

In a further aspect the present invention provides the use of a compound of formula (I) in the manufacture of a medicament for the treatment and/or prohylaxis of microscopic colitis.

In a further aspect the present invention provides the use of a compound of formula (I) in the manufacture of a medicament for the treatment and/or prohylaxis of indeterminant colitis.

In a further aspect the present invention provides the use of a compound of formula (I) in the manufacture of a medicament for the treatment and/or prohylaxis of irritable bowel disorder.

In a further aspect the present invention provides the use of a compound of formula (I) in the manufacture of a medicament for the treatment and/or prohylaxis of irritable bowel syndrome.

In a further aspect the present invention provides the use of a compound of formula (I) in the manufacture of a medicament for the treatment and/or prohylaxis of dyslipidemic conditions.

In a further aspect the present invention provides the use of a compound of formula (I) in the manufacture of a medicament for the treatment and/or prohylaxis of insulin resistance syndrome and/or metabolic disorders.

In a further aspect the present invention provides the use of a compound of formula (I) in the manufacture of a medicament for the treatment and/or prophylaxis of cardiovascular disease.

In a further aspect the present invention provides the use of a compound of formula (I) in the manufacture of a medicament for the treatment and/or prophylaxis of atherosclerosis.

In a further aspect the present invention provides the use of a compound of formula (I) in the manufacture of a medicament for the treatment and/or prophylaxis of hypercholesterolemia.

In a further aspect the present invention provides the use of a compound of formula (I) in the manufacture of a medicament for the treatment and/or prophylaxis of conditions associated with a need for improving reverse cholesterol transport.

In a further aspect the present invention provides the use of a compound of formula (I) in the manufacture of a medicament for the treatment and/or prophylaxis of conditions associated with a need for decreasing intestinal cholesterol absorption.

In a further aspect the present invention provides the use of a compound of formula (I) in the manufacture of a medicament for the treatment and/or prophylaxis of conditions associated with a need for increasing HDL-cholesterol levels.

In a further aspect the present invention provides the use of a compound of formula (I) in the manufacture of a medicament for the treatment and/or prophylaxis of conditions associated with a need for decreasing LDL-cholesterol levels.

In a further aspect the present invention provides the use of a compound of formula (I) in the manufacture of a medicament for the treatment and/or prophylaxis of inflammatory conditions.

In a further aspect the present invention provides the use of a compound of formula (I) in the manufacture of a medicament for the treatment and/or prophylaxis of Alzheimer's disease.

In a further aspect the present invention provides the use of a compound of formula (I) in the manufacture of a medicament for the treatment and/or prophylaxis of arteriosclerosis.

In a further aspect the present invention provides the use of a compound of formula (I) in the manufacture of a medicament for the treatment and/or prophylaxis of type 2 diabetes.

In a further aspect the present invention provides the use of a compound of formula (I) in the manufacture of a medicament for the treatment and/or prophylaxis of conditions associated with a need for improving HDL function.

In a further aspect the present invention provides the use of a compound of formula (I) in the manufacture of a medicament for the treatment and/or prophylaxis of hyperlipidemic conditions.

In a further aspect the present invention provides the use of a compound of formula (I) in the manufacture of a medicament for the treatment and/or prophylaxis of dyslipidemia.

Combination Therapy

The compounds of the invention may be combined with another therapeutic agent that is useful in the treatment of disorders associated with the development and progress of atherosclerosis such as hypertension, hyperlipidaemias, dyslipidaemias, diabetes, inflammation and obesity. The compounds of the invention may be combined with another therapeutic agent that decreases the ratio of LDL:HDL or apoB:apoA-1 or an agent that causes a decrease in circulating levels of LDL-cholesterol or apoB or triglycerides. In patients with diabetes mellitus the compounds of the invention may also be combined with therapeutic agents used to correct carbohydrate metabolism and treat complications related to microangiopathies.

In another aspect of the present invention, the compound of formula (I), or a pharmaceutically acceptable salt or solvate thereof, or a solvate of such a salt, may be administered in association with cholesterol biosynthesis inhibitors, or pharmaceutically acceptable salts, solvates, solvates of such salts or prodrugs thereof. Suitable cholesterol biosynthesis inhibitors include HMG CoA reductase inhibitors, squalene synthesis inhibitors and squalene epoxidase inhibitors. Suitable squalene synthesis inhibitor are squalestatin 1, TAK-475, compounds described in WO2005012284 and a suitable squalene epoxidase inhibitor is NB-598.

In this aspect of the invention, the compound of formula (I), or a pharmaceutically acceptable salt or solvate thereof, or a solvate of such a salt, may be administrated in association with an HMG CoA reductase inhibitor, or pharmaceutically acceptable salts, solvates, solvates of such salts or prodrugs thereof. Suitably the HMG CoA reductase inhibitor, or pharmaceutically acceptable salts, solvates, solvates of such salts or prodrugs thereof are statins well known in the art. Particular statins are selected from the group consisting of atorvastatin, fluvastatin, pitavastatin, lovastatin, mevastatin, nicostatin, nivastatin, pravastatin and simvastatin, or a pharmaceutically acceptable salt, especially sodium or calcium, solvate, solvate of such a salt or a prodrug thereof. A particular statin is atorvastatin, or a pharmaceutically acceptable salt, solvate, solvate of such a salt or a prodrug thereof. A more particular statin is atorvastatin calcium salt. A particularly preferred statin is, however, rosuvastatin, or a pharmaceutically acceptable salt, solvate, solvate of such a salt or a prodrug thereof. A preferable particular statin is rosuvastatin calcium salt.

In the present application, the term "cholesterol biosynthesis inhibitors" also includes chemical modifications of the HMG CoA reductase inhibitors, squalene synthesis inhibitors and squalene epoxidase inhibitors, such as esters, prodrugs and metabolites, whether active or inactive.

In another aspect of the present invention, the compound of formula (I), or a pharmaceutically acceptable salt or solvate thereof, or a solvate of such a salt, may be administered in association with an inhibitor of the ileal bile acid transport system (IBAT inhibitor), or pharmaceutically acceptable salts, solvates, solvates of such salts or prodrugs thereof. Suitable compounds possessing IBAT inhibitory activity have been described, see for instance the compounds described in WO 93/16055, WO 94/18183, WO 94/18184, WO 96/05188, WO 96/08484, WO 96/16051, WO 97/33882, WO 98/07449, WO 98/03818, WO 98/38182, WO 99/32478, WO 99/35135, WO 98/40375, WO 99/35153, WO 99/64409, WO 99/64410, WO 00/01687, WO 00/47568, WO 00/61568, WO 00/62810, WO 01/68906, DE 19825804, WO 00/38725, WO 00/38726, WO 00/38727, WO 00/38728, WO 00/38729, WO 01/68906, WO 01/66533, WO 02/32428, WO 02/50051, WO 03/040124, WO 03/040127, WO03/043992, WO03/061604, WO 04/020421, WO 04/076430, EP 864 582, EP 489 423, EP 549 967, EP 573 848, EP 624 593, EP 624 594, EP 624 595 and EP 624 596 and the contents of these patent applications are incorporated herein by reference.

Further suitable compounds possessing IBAT inhibitory activity have been described in WO 94/24087, WO 98/56757, WO 00/20392, WO 00/20393, WO 00/20410, WO 00/20437, WO 01/34570, WO 00/35889, WO 01/68637, WO 02/08211, WO 03/020710, WO 03/022825, WO 03/022830, WO 03/022286, WO 03/091232, WO 03/106482, JP 10072371, U.S. Pat. No. 5,070,103, EP 251 315, EP 417 725, EP 869 121, EP 1 070 703 and EP 597 107 and the contents of these patent applications are incorporated herein by reference.

Particular classes of IBAT inhibitors suitable for use in the present invention are benzothiazepines, and the compounds described in the claims, particularly claim 1, of WO 00/01687, WO 96/08484 and WO 97/33882 are incorporated herein by reference. Other suitable classes of IBAT inhibitors are the 1,2-benzothiazepines, 1,4-benzothiazepines and 1,5-benzothiazepines. A further suitable class of IBAT inhibitors is the 1,2,5-benzothiadiazepines.

One particular suitable compound possessing IBAT inhibitory activity is (3R,5R)-3-butyl-3-ethyl-1,1-dioxido-5-phenyl-2,3,4,5-tetrahydro-1,4-benzothiazepin-8-yl β-D-glucopyranosiduronic acid (EP 864 582). A further suitable compound possessing IBAT inhibitory activity is S-8921 (EP 597 107).

In another aspect of the present invention, the compound of formula (I), or a pharmaceutically acceptable salt or solvate thereof, or a solvate of such a salt, may be administered in association with a cholesterol absorption antagonist, or pharmaceutically acceptable salts, solvates, solvates of such salts or prodrugs thereof, for example AVE-5530 or for example azetidinones such as ezetrol (zetia, ezetimibe) and those described in U.S. Pat. No. 5,767,115 which are incorporated herein by reference. Suitable compounds possessing cholesterol absorption antagonist activity have been described, see for instance the compounds described in WO 02/50027, WO 02/66464, WO 04/005247, WO 04/000803, WO 04/000804, WO 04/000805, WO05021495, WO05021497 and WO05033100 which are incorporated herein by reference.

In another aspect of the present invention, the compound of formula (I), or a pharmaceutically acceptable salt or solvate thereof, or a solvate of such a salt, may be administered in association with a bile acid sequestrant or pharmaceutically acceptable salts, solvates, solvates of such salts or prodrugs thereof. Suitable bile acid sequestrants include HBS-107, cholestyramine (Questran®, LoCholest®), cholestemide (Cholebine®), colesevelam (Welcholo®), cholistipol (Colestid®) and cosevelam hydrochloride.

In another aspect of the present invention, the compound of formula (I), or a pharmaceutically acceptable salt or solvate thereof, or a solvate of such a salt, may be administered in association with other agents that increase reverse cholesterol transport by other means than increasing expression of ABC-transporters, eg. ApoA-1 mimetica. See for instance the compounds described in WO-2004094471 which are incorporated herein by reference. Suitable apoA-1 mimetica include D-F4, ETC 216, ETC 642, RTC 588, ETC 1001, Apo A1 Milano, D-4F and AVP-26452.

In another aspect of the invention, the compound of formula (I), or a pharmaceutically acceptable salt or solvate thereof, or a solvate of such a salt, may be administered in association with a peroxisome proliferator-activated receptor (PPAR) modulating agent. PPAR modulating agents include a PPAR alpha and/or gamma and/or delta agonist, or pharmaceutically acceptable salts, solvates, solvates of such salts or prodrugs thereof. Suitable PPAR alpha and/or gamma and/or delta agonists, pharmaceutically acceptable salts, solvates, solvates of such salts or prodrugs thereof are well known in the art. These include the compounds described in WO 01/12187, WO 01/12612, WO 99/62870, WO 99/62872, WO 99/62871, WO 98/57941, WO 01/40170, WO 04/000790, WO 04/000295, WO 04/000294, WO 03/051822, WO 03/051821, WO 02/096863, WO 04/056748, WO 03/051826, WO 02/085844, WO 01/40172, J Med Chem, 1996, 39, 665, Expert Opinion on Therapeutic Patents, 10 (5), 623-634 (in particular the compounds described in the patent applications listed on page 634) and J Med Chem, 2000, 43, 527 which are all incorporated herein by reference. Particularly a PPAR alpha and/or gamma and/or delta agonist refers to muraglitazar (BMS 298585), rivoglitazone (CS-011), netoglitazone (MCC-555), balaglitazone (DRF-2593, N,N-2344), clofibrate (Atromid-S®), fenofibrate, bezafibrate (Oralipin®), gemfibrozil (Lopid®), ciprofibrate (Ciprol®), pioglitazone (Actos®), rosiglitazone (Avandia®), AVE-0847, AVE-8134, CLX-0921, DRF-10945, DRF-4832, E-3030, K-111, KRP-101, LBM-642 (oxeglitazar), LY-518674, LY-674, naveglitazar (LY-818), LY-929, 641597, GW-590735, GW-677954, GW-501516, metaglidasan (MBX-102), MBX-2044, ONO-5129, PLX-204, R-483 (BM131258), R-119702, T-131 (AMG-131), TAK-559 or TAK-654. Particularly a PPAR alpha and/or gamma and/or delta agonist refers to tesaglitazar ((S)-2-ethoxy-3-[4-(2-{4-methanesulphonyl-oxyphenyl}ethoxy)phenyl]propanoic acid) and pharmaceutically acceptable salts thereof.

In yet another aspect of the invention, the compound of formula (I), or a pharmaceutically acceptable salt or solvate thereof, or a solvate of such a salt, may be administered in association with a pyruvate dehydrogenase kinase (PDK) inhibitor, or a pharmaceutically acceptable salt, solvate, solvate of such a salt or a prodrug thereof.

In another aspect of the invention, the compound of formula (I), or a pharmaceutically acceptable salt or solvate thereof, or a solvate of such a salt, may be administered in association with a cholesteryl ester transfer protein (CETP) inhibitor, or pharmaceutically acceptable salts, solvates, solvates of such salts or prodrugs thereof, for example JTT-705, torcetrapib (CP-529414) and those referenced and described in WO 00/38725 page 7 line 22-page 10, line 17 which are incorporated herein by reference.

In another aspect of the invention, the compound of formula (I), or a pharmaceutically acceptable salt or solvate thereof, or a solvate of such a salt, may be administered in association with a microsomal-triglyceride transfer protein (MTP) inhibitor, or pharmaceutically acceptable salts, solvates, solvates of such salts or prodrugs thereof, for example implipatide, CP-346086, JTT-130 and those described in WO 03/004020, WO 03/002533, WO 02/083658 and WO 00/242291, and the contents of these patent applications are incorporated herein by reference, or those described in Science, 282, 751-54, 1998 which are incorporated herein by reference.

In another aspect of the invention, the compound of formula (I), or a pharmaceutically acceptable salt or solvate thereof, or a solvate of such a salt, may be administered in association with an agonist to the receptor HM74A (nicotinic acid receptor). Examples of HM74A agonists are e g compounds described in WO2005011677, WO2004032928, WO2004033431 or a nicotinic acid derivative, or pharmaceutically acceptable salts, solvates, solvates of such salts or prodrugs thereof, including slow release and combination products, for example, nicotinic acid (niacin), acipimox, nicofuranose, NIASPAN® and niceritrol.

In another aspect of the invention, the compound of formula (I), or a pharmaceutically acceptable salt or solvate thereof, or a solvate of such a salt, may be administered in association with a acyl coenzymA: cholesterol O-acyltransferase (ACAT) inhibitor or ACAT2, or pharmaceutically acceptable salts, solvates, solvates of such salts or prodrugs thereof, for example CS-505, eflucimibe (F-12511), K-604 and SMP-797.

In yet another aspect of the invention, the compound of formula (I) or a pharmaceutically acceptable salt or solvate thereof, or a solvate of such a salt, may be administered in association with modulators of nuclear hormone receptors such as farnesoid X receptor (FXR), or pharmaceutically acceptable salt, solvate, solvate of such a salt or a prodrug thereof for example INT-747, or modulators of nuclear receptors such as retenoid X receptor (RXR), or a pharmaceutically acceptable salt, solvate, solvate of such a salt or a prodrug thereof.

In another aspect of the invention, the compound of formula (I), or a pharmaceutically acceptable salt or solvate thereof, or a solvate of such a salt, may be administered in association with a phytosterol compound, or pharmaceutically acceptable salts, solvates, solvates of such salts or prodrugs thereof, for example stanols and FM-VP4.

In another aspect of the invention, the compound of formula (I), or a pharmaceutically acceptable salt or solvate thereof, or a solvate of such a salt, may be administered in association with other therapies for the treatment of metabolic syndrome or type 2 diabetes and its associated complications, these include biguanide drugs, for example metformin, phenformin and buformin, insulin (synthetic insulin analogues, amylin) and oral antihyperglycemics (these are divided into prandial glucose regulators and alpha-glucosidase inhibitors). An example of an alpha-glucosidase inhibitor is acarbose or voglibose or miglitol. An example of a prandial glucose regulator is repaglinide or nateglinide.

In another aspect of the invention, the compound of formula (I), or a pharmaceutically acceptable salt or solvate thereof, or a solvate of such a salt, may be administered in association with a sulfonylurea for example: glimepiride, glibenclamide (glyburide), gliclazide, glipizide, gliquidone, chloropropamide, tolbutamide, acetohexamide, glycopyramide, carbutamide, glibonuride, glisoxepid, glybuthiazole, glibuzole, glyhexamide, glymidine, glypinamide, phenbutamide, tolcylamide and tolazamide. Preferably the sulfonylurea is glimepiride or glibenclamide (glyburide). More preferably the sulfonylurea is glimepiride. Therefore the present invention includes administration of a compound of the present invention in conjunction with one, two or more existing therapies described in this paragraph. The doses of the other existing therapies for the treatment of type 2 diabetes and its associated complications will be those known in the art and approved for use by regulatory bodies for example the FDA and may be found in the Orange Book published by the FDA. Alternatively smaller doses may be used as a result of the benefits derived from the combination.

In another aspect of the invention, the compound of formula (I), or a pharmaceutically acceptable salt or solvate thereof, or a solvate of such a salt, may be administered in association with an antihypertensive compound for example althiazide, benzthiazide, captopril, carvedilol, chlorothiazide sodium, clonidine hydrochloride, cyclothiazide, delapril hydrochloride, dilevalol hydrochloride, doxazosin mesylate, fosinopril sodium, guanfacine hydrochloride, methyldopa, metoprolol succinate, moexipril hydrochloride, monatepil maleate, pelanserin hydrochloride, phenoxybenzemine hydrochloride, prazosin hydrochloride, primidolol, quinapril hydrochloride, quinaprilat, ramipril, terazosin hydrochloride, candesartan, candesartan cilexetil, telmisartan, amlodipine besylate, amlodipine maleate and bevantolol hydrochloride, or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with an angiotensin converting enzyme (ACE) inhibitor. Particular ACE inhibitors or pharmaceutically acceptable salts, solvates, solvate of such salts or prodrugs thereof, including active metabolites, which can be used in combination with a compound of formula (I) include but are not limited to, the following compounds: alacepril, alatriopril, ancovenin, benazepril, benazepril hydrochloride, benazeprilat, benzoylcaptopril, captopril, captopril-cysteine, captopril-glutathione, ceranopril, cilazapril, cilazaprilat, delapril, delapril-diacid, enalapril, enalaprilat, enapril, epicaptopril, foroxymithine, fosfenopril, fosenopril, fosenopril sodium, fosinopril, fosinopril sodium, fosinoprilat, fosinoprilic acid, hemorphin-4, imidapril, indolapril, indolaprilat, lisinopril, lyciumin A, lyciumin B, moexipril, moexiprilat, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spiropril hydrochloride, temocapril, temocapril hydrochloride, teprotide, trandolapril, trandolaprilat, zofenopril and zofenoprilat. Preferred ACE inhibitors are ramipril, ramiprilat, lisinopril, enalapril and enalaprilat. More preferred ACE inhibitors are ramipril and ramiprilat.

In another aspect of the invention, the compound of formula (I), or a pharmaceutically acceptable salt or solvate thereof, or a solvate of such a salt, may be administered in association with an angiotensin II receptor antagonist. Preferred angiotensin II receptor antagonists, pharmaceutically acceptable salts, solvates, solvate of such salts or a prodrugs thereof for use in combination with a compound of formula (I) include, but are not limited to, compounds: candesartan, candesartan cilexetil, losartan, valsartan, irbesartan, telmisartan and eprosartan. Particularly preferred angiotensin II receptor antagonists or pharmaceutically acceptable derivatives thereof are candesartan and candesartan cilexetil, or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with an andrenergic blocker. Andrenergic blocker include an alpha andrenergic blocker, or a beta andrenergic blocker, or a mixed alpha/beta andrenergic blocker or pharmaceutically acceptable salts, solvates, solvates of such salts or prodrugs thereof.

Examples of andrenergic blockers are bretylium tosylate, dihydroergotamine so mesylate, phentolaiminne mesylate, solypertine tartrate, zolertine hydrochloride, carvedilol, labetalol hydrochloride, fenspiride hydrochloride, labetalol hydrochloride, proroxan, alfuzosin hydrochloride, acebutolol, acebutolol hydrochloride, alprenolol hydrochloride, atenolol, bunolol hydrochloride, carteolol hydrochloride, celiprolol hydrochloride, cetamolol hydrochloride, cicloprolol hydrochloride, dexpropranolol hydrochloride, diacetolol hydrochloride, dilevalol hydrochloride, esmolol hydrochloride, exaprolol hydrochloride, flestolol sulfate, labetalol hydrochloride, levobetaxolol hydrochloride, levobunolol hydrochloride, metalol hydrochloride, metoprolol, metoprolol tartrate, nadolol, pamatolol sulfate, penbutolol sulfate, practolol, propranolol hydrochloride, sotalol hydrochloride, timolol, timolol maleate, tiprenolol hydrochloride, tolamolol, bisoprolol, bisoprolol fumarate and nebivolol or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with an andrenergic stimulant for example combination product of chlorothiazide and methyldopa, the combination product of methyldopa hydrochlorothiazide and methyldopa, clonidine hydrochloride, clonidine, the combination product of chlorthalidone and clonidine hydrochloride and guanfacine hydrochloride, or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with calcium channel blocker for example clentiazem maleate, amlodipine besylate, isradipine, nimodipine, felodipine, nilvadipine, nifedipine, teludipine hydrochloride, diltiazem hydrochloride, belfosdil, verapamil hydrochloride or fostedil, or an AT-1 blocker, or a saluretic, or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with a diuretic for example the combination product of hydrochlorothiazide and spironolactone and the combination product of hydrochlorothiazide and triamterene, or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with a vasodilator for example coronary vasodilators (for example fostedil, azaclorzine hydrochloride, chromonar hydrochloride, clonitrate, diltiazem hydrochloride, dipyridamole, droprenilamine, erythrityl tetranitrate, isosorbide dinitrate, isosorbide mononitrate, lidoflazine, mioflazine hydrochloride, mixidine, molsidomine, nicorandil, nifedipine, nisoldipine, nitroglycerine, oxprenolol hydrochloride, pentrinitrol, perhexyline maleate, prenylamine, propatyl nitrate, terodiline hydrochloride, tolamolol and verapamil), or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with a anti-anginal agents for example amlodipine besylate, amlodipine maleate, betaxolol hydrochloride, bevantolol hydrochloride, butoprozine hydrochloride, carvedilol, cinepazet maleate, metoprolol succinate, molsidomine, monatepil maleate, primidolol, ranolazine hydrochloride, tosifen or verapamil hydrochloride or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with an anti-coagulants selected from argatroban, bivalirudin, dalteparin sodium, desirudin, dicumarol, Iyapolate sodium, nafamostat mesylate, phenprocoumon, tinzaparin sodium and warfarin sodium or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with an antithrombotic agents for example anagrelide hydrochloride, bivalirudin, cilostazol, dalteparin sodium, danaparoid sodium, dazoxiben hydrochloride, efegatran sulfate, enoxaparin sodium, fluretofen, ifetroban, ifetroban sodium, lamifiban, lotrafiban hydrochloride, napsagatran, orbofiban acetate, roxifiban acetate, sibrafiban, tinzaparin sodium, trifenagrel, abciximab and zolimomab aritox or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with other agents that act as or deliver a Factor IIa agonist for example 3DP-4815, AZD-0837, melagatran, ximelagatran, ART-123, lepirudin, AVE-5026, bivaluridin, dabigatran etexilate, E-4444, odiparcil, ardeparin sodium, pegmusirudin, LB-30870, dermatan sulfate, argatroban, MCC-977, desirudin, deligoparin sodium, PGX-100, idraparinux sodium, SR-123781, SSR-182289A, SCH-530348, TRIB50, TGN-167, TGN-255, and compounds described in WO94/29336, WO97/23499 and WO02/44145, which are incorporated hereby by reference.

In another aspect of the invention, the compound of formula (I), or a pharmaceutically acceptable salt or solvate thereof, or a solvate of such a salt, may be administered in association with a fibrinogen receptor antagonists for example roxifiban acetate, fradafiban, orbofiban, lotrafiban hydrochloride, tirofiban, xemilofiban, monoclonal antibody 7E3 and sibrafiban or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with a platelet inhibitors for example cilostezol, clopidogrel bisulfate, epoprostenol, epoprostenol sodium, ticlopidine hydrochloride, aspirin, ibuprofen, naproxen, sulindae, indomethacin, mefenamate, droxicam, diclofenac, sulfinpyrazone and piroxicam, dipyridamole or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with a platelet aggregation inhibitors for example acadesine, beraprost, beraprost sodium, ciprostene calcium, itezigrel, lifarizine, lotrafiban hydrochloride, orbofiban acetate, oxagrelate, fradafiban, orbofiban, tirofiban and xemilofiban or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with a hemorrheologic agents for example pentoxifylline or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with lipoprotein associated coagulation inhibitors; or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with a Factor VIIa inhibitor or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with a Factor Xa inhibitor or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with a low molecular weight heparin for example enoxaparin, nardroparin, dalteparin, certroparin, parnaparin, reviparin and tinzaparin or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with an anti-obesity compound, or pharmaceutically acceptable salts, solvates, solvates of such salts or prodrugs thereof, for example a pancreatic lipase inhibitor e.g. orlistat (EP 129,748), ATL-962, GT-389255 or an appetite (satiety) controlling substance for example sibutramine (Meridia®, Reductil®, GB 2,184,122 and U.S. Pat. No. 4,929,629), PYY 3-36 (amylin), APD-356, 1426, Axokine, T-71, a cannabinoid 1 (CB1) antagonist or inverse agonist, or pharmaceutically acceptable salts, solvates, solvates of such salts or prodrugs thereof, for example rimonabant (EP 656354), AVE-1625, CP945598, SR-147778, SLV-319, and as described in WO01/70700, or a Fatty Acid Synthesis (FAS) inhibitor, or pharmaceutically acceptable salts, solvates, solvates of such salts or prodrugs thereof or a melanin concentrating hormone (MCH) antagonist, or pharmaceutically acceptable salts, solvates, solvates of such salts or prodrugs thereof, for example 856464 and as described in WO 04/004726.

In another aspect of the invention, the compounds of formula (I), or a pharmaceutically acceptable salt or solvate thereof, or a solvate of such a salt, may be administrated in association with an anti-inflammatory agent such as glucocorticoids, non-steroidal anti-inflammatory agents (NSAID) or intestinal anti-inflammatory agents, or pharmaceutically acceptable salts, solvates, solvates of such salts or prodrugs thereof. Suitable glucocorticoids will include, but will not be limited to betametason, dexametason, methyl prednisolon, prednisolon, prednison, triamcinolon, hydrocortison, cortison and budesonid. Suitable non-steroidal anti-inflammatory agents will include, but will not be limited to indometacin, diclofenac, ibuprofen as well as acetylsalicylic acid. Suitable intestinal anti-inflammatory agents will include, but will not be limited to amino salicylates such as sulfasalazin, mesalazin, olsalazin and balsalazid.

In another aspect of the invention, the compounds of formula (I), or a pharmaceutically acceptable salt or solvate thereof, or a solvate of such a salt, may be administrated in association with a cholinesterase inhibitor or an N-methyl-D-aspartate (NMDA) receptor antagonist, or pharmaceutically acceptable salts, solvates, solvates of such salts or prodrugs thereof, such as donepezil, rivastigmin or galantamin or memantin.

Therefore in an additional feature of the invention, there is provided a method of treating and/or preventing metabolic disorders in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section or a pharmaceutically acceptable salt, solvate, solvate of such a salt or a prodrug thereof.

Therefore in an additional feature of the invention, there is provided a method for the treatment and/or prohylaxis of type 2 diabetes and its associated complications in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

Therefore in an additional feature of the invention, there is provided a method of treating and/or preventing hyperlipidemic conditions in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section or a pharmaceutically acceptable salt, solvate, solvate of such a salt or a prodrug thereof.

In an additional feature of the invention, there is provided a method for the treatment and/or prohylaxis of dyslipidemia in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prohylaxis of the insulin resistance syndrome in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prohylaxis of cardiovascular disease in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prohylaxis of atherosclerosis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prohylaxis of hypercholesterolemia in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing conditions associated with a need for improving reverse cholesterol transport in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing conditions associated with a need for decreasing intestinal cholesterol absorption in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing conditions associated with a need for increasing HDL-cholesterol levels in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing conditions associated with a need for decreasing LDL-cholesterol levels in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prohylaxis of inflammatory conditions in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prohylaxis of Alzheimer's disease in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prohylaxis of arteriosclerosis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing conditions associated with a need for improving HDL function in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing rheumatoid arthritis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing juvenile rheumatoid arthritis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing systemic lupus erythematosus in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing osteoarthritis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing degenerative joint disease in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing one or more connective tissue diseases in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing ankylosing spondolytis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing bursitis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing Sjogren's syndrome in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing psoriasis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing psoriatic arthritis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing neuraligia in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing synovitis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing glomerulonephritis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing vasculitis or sarcoidosis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing inflammatory bowel disease in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing Crohn's disease in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing ulcerative colitis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing Coeliac disease in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing proctitis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing eosinopilic gastroenteritis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing mastocytosis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing microscopic colitis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing indeterminant colitis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing irritable bowel disorder in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing irritable bowel syndrome in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing dyslipidemic conditions in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt or solvate thereof, or a solvate of such a salt, and one of the other compounds described in this combination section or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula (I), or a pharmaceutically acceptable salt or solvate thereof, or a solvate of such a salt, and one of the other compounds described in this combination section or a pharmaceutically acceptable salt, solvate, solvate of such a salt or a prodrug thereof.

According to a further aspect of the present invention there is provided a kit comprising:
a) a compound of formula (I), or a pharmaceutically acceptable salt or solvate thereof, or a solvate of such a salt, in a first unit dosage form;
b) one of the other compounds described in this combination section or a pharmaceutically acceptable salt, solvate, solvate of such a salt or a prodrug thereof; in a second unit dosage form; and
c) container means for containing said first and second dosage forms.

According to a further aspect of the present invention there is provided a kit comprising:
a) a compound of formula (I), or a pharmaceutically acceptable salt or solvate thereof, or a solvate of such a salt, together with a pharmaceutically acceptable diluent or carrier, in a first unit dosage form;
b) one of the other compounds described in this combination section or a pharmaceutically acceptable salt, solvate, solvate of such a salt or a prodrug thereof, in a second unit dosage form; and
c) container means for containing said first and second dosage forms.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of metabolic disorders and its associated complications in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of metabolic syndrome or type 2 diabetes and its associated complications in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of dyslipidemia in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of hyperlipidaemic conditions in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of cardiovascular disease in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of atherosclerosis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of hypercholesterolemia in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of a conditions associated with a need for improving reverse cholesterol transport in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of a conditions associated with a need for decreasing intestinal cholesterol absorption in a warm-blooded animal, such as man.

According to another feature of the invention there is provided the use of a compound of the formula (I), of such or a pharmaceutically acceptable salt or solvate thereof, or a solvate a salt, and one of the other compounds described in this combination section, or a pharmaceutically acceptable salt, solvate, solvate of such a salt or a prodrug thereof, in the manufacture of a medicament for use in the treatment and/or prophylaxis of a conditions associated with a need for increasing HDL-cholesterol levels in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of a conditions associated with a need for decreasing LDL-cholesterol levels in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of inflammatory conditions in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of Alzheimer's disease in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of arteriosclerosis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of a conditions associated with a need for improving HDL function in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of rheumatoid arthritis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of juvenile rheumatoid arthritis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of systemic lupus erythematosus in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of osteoarthritis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of degenerative joint disease in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of one or more connective tissue diseases in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of ankylosing spondolytis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of bursitis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of Sjogren's syndrome in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of psoriasis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of psoriatic arthritis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of neuraligia in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of synovitis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of glomerulonephritis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of vasculitis or sarcoidosis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of inflammatory bowel disease in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of Crohn's disease in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of ulcerative colitis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of Coeliac disease in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of proctitis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of eosinopilic gastro-enteritis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of mastocytosis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of microscopic colitis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of indeterminant colitis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of irritable bowel disorder in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of irritable bowel syndrome in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of insulin resistance syndrome in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of dyslipidemic conditions in a warm-blooded animal, such as man.

According to a further aspect of the present invention there is provided a combination treatment comprising the administration of an effective amount of a compound of the formula (I), or a pharmaceutically acceptable salt or solvate thereof, or a solvate of such a salt, optionally together with a pharmaceutically acceptable diluent or carrier, with the simultaneous, sequential or separate administration of an effective amount of one of the other compounds described in this combination section, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

Further Aspects of the Invention

Further aspect 1. A compound of general formula I

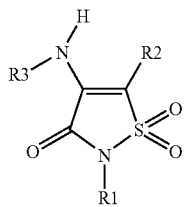

or a pharmaceutically acceptable salt or solvate thereof a solvate of such a salt wherein $R^1$ represents X which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^b$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$ or $NR^aC(O)NR^aR^a$;

cycloalkyl or heterocyclyl each optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$ or $NR^aC(O)NR^aR^a$;

phenyl or heteroaryl each optionally substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$ or $NR^aC(O)NR^aR^a$;

cycloalkylY or heterocyclylY wherein cycloalkyl or heterocyclyl each optionally is substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$ or $NR^aC(O)NR^aR^a$;

phenylY or heteroarylY wherein phenyl or heteroaryl each optionally is substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$ or $NR^aC(O)NR^aR^a$;

$R^2$ represents phenyl which is optionally substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, $C(O)NR^aR^a$, $NR^aC(O)_b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$;

$R^{13}$ represents aryl or $Het^1$ wherein aryl or $Het^1$ each optionally is substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, Q, Het$^2$, R, Het$^3$, QZ, Het$^2$Z, RZ, Het$^3$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$;

Het$^4$ or T wherein Het$^4$ or T each optionally is substituted on the aromatic ring by one or more of the following: halogen (Cl, F, I, Br), OH, CN, NO$_2$, NR$^a$R$^a$, OR$^b$, SR$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, Q, Het$^2$, R, Het$^3$, QZ, Het$^2$Z, RZ, Het$^3$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$, and wherein Het$^4$ or T each optionally is substituted on the non-aromatic ring by one or more of the following: F, OH, CN, NR$^a$R$^a$, OR$^b$, SR$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, thioxo, Q, Het$^2$, R, Het$^3$, QZ, Het$^2$Z, RZ, Het$^3$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$;

and in the above definitions

X represents a straight or branched, saturated or unsaturated alkyl group having 1 to 6 carbon atoms wherein said alkyl group may optionally be interrupted by O, S, S(O), SO$_2$, C(O), NR$^a$, OC(O), C(O)O, NR$^a$C(O), C(O)NR$^a$, SO$_2$NR$^a$ or NR$^a$SO$_2$;

Y binds to nitrogen in 2-position in the isothiazol-3(2H)-one 1,1-dioxide, and represents a straight or branched, saturated or unsaturated alkyl group having 1 to 3 carbon atoms wherein said alkyl group may optionally be interrupted or ended by O, S, S(O), SO$_2$, C(O), OC(O), C(O)O, NR$^c$C(O), C(O)NR$^c$, NR$^c$ and/or Y is optionally substituted by one or more of the following: OH, F, CN, NR$^a$R$^a$, C$_1$-C$_4$alkyl, OR$^b$, SR$^b$, S(O)R$^b$ or SO$_2$R$^b$;

Z binds to aryl, Het$^1$, Het$^4$ or T and one of the following: Q, Het$^2$, R or Het$^3$, and represents a straight or branched, saturated or unsaturated alkyl group having 1 to 6 carbon atoms wherein said alkyl group may optionally be interrupted or ended by O, S, S(O), SO$_2$, C(O), OC(O), C(O)O, NR$^a$C(O), C(O)NR$^a$, NR$^a$, SO$_2$NR$^a$, NR$^a$SO$_2$, optionally consists only of one of the following: O, S, S(O), SO$_2$, C(O), OC(O), C(O)O, NR$^a$C(O), C(O)NR$^a$, NR$^a$, SO$_2$NR$^a$, NR$^a$SO$_2$ and/or Z is optionally substituted by one or more of the following: OH, F, CN, NR$^c$R$^c$, C(O)R$^c$, OR$^b$, SR$^c$, S(O)R$^c$, SO$_2$R$^c$, phenyl, phenylC$_1$-C$_3$alkyl, or C$_1$-C$_4$alkyl which is optionally substituted by one or more of the following: F, OH, NR$^a$R$^a$, SR$^b$, S(O)R$^b$, SO$_2$R$^b$, OR$^b$;

Q represents a saturated or unsaturated non-aromatic monocyclic ring composed of 3, 4, 5, 6, 7, 8 carbon atoms, which is optionally substituted by one or more of the following: F, OH, CN, NR$^a$R$^a$, OR$^b$, SR$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$;

R represents a phenyl group which is optionally substituted by one or more of the following: halogen (Cl, F, I, Br), OH, CN, NO$_2$, NR$^a$R$^a$, OR$^b$, SR$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$;

aryl represents a phenyl group which binds to nitrogen in 4-position on the isothiazol-3(2H)-one 1,1-dioxide;

T binds to nitrogen in 4-position on the isothiazol-3(2H)-one 1,1-dioxide, and represents a bicyclic aromatic or partly aromatic carbocyclic ring composed of 4, 5, 6, 7, 8, 9 or 10 carbon atoms, and where it is the aromatic part of the bicyclic ring that binds to nitrogen in 4-position on the isothiazol-3(2H)-one 1,1-dioxide;

Het$^1$ binds to nitrogen in 4-position on the isothiazol-3(2H)-one 1,1-dioxide, and represents an aromatic 3-10 membered monocyclic ring in which one or more of the atoms in the ring is an element other than carbon, for example nitrogen, oxygen and sulfur;

Het$^2$ represents a saturated or unsaturated non-aromatic 3-10 membered monocyclic ring in which one or more of the atoms in the ring is an element other than carbon, for example nitrogen, oxygen or sulfur, and wherein the ring optionally is substituted by one or more of the following: F, OH, CN, NR$^a$R$^a$, OR$^b$, SR$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$;

Het$^3$ represents an aromatic 3-10 membered monocyclic ring in which one or more of the atoms in the ring is an element other than carbon, for example nitrogen, oxygen and sulfur, and which is substituted by one or more of the following: halogen (Cl, F, I, Br), OH, CN, NO$_2$, NR$^a$R$^a$, OR$^b$, SR$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$;

Het$^4$ binds to nitrogen in 4-position on the isothiazol-3(2H)-one 1,1-dioxide, and represents an aromatic or partly aromatic 6-10 membered bicyclic ring in which one or more of the atoms in the ring optionally is an element other than carbon, for example nitrogen, oxygen and sulfur, and where it is the aromatic part of the bicyclic ring that binds to nitrogen in 4-position on the isothiazol-3(2H)-one 1,1-dioxide;

$R^a$ independently represents H or a straight or branched, saturated or unsaturated $C_1$-$C_4$alkyl chain optionally substituted by one or more F;

$R^b$ independently represents a straight or branched, saturated or unsaturated $C_1$-$C_4$alkyl chain optionally substituted by one or more F;

$R^c$ independently represents H or a straight or branched, saturated or unsaturated $C_1$-$C_3$alkyl chain optionally substituted by one or more F.

Further aspect 2. A compound according to further aspect 1 or a pharmaceutically acceptable salt or solvate thereof, or a solvent of such a salt, wherein $R^1$ represents X which is optionally substituted by one or more of the following: F, OH, CN, $NR^aR^a$, $OR^b$, $SR^b$, $S(O)R^b$, $SO_2R^b$, $C(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$ or $C(O)R^b$;

cycloalkyl or heterocyclyl each optionally substituted by one or more of the following: F, OH, CN, $NR^aR^a$, $OR^b$, $SR^b$, $S(O)R^b$, $SO_2R^b$, $C(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$ or $C(O)R^b$;

phenyl or heteroaryl each optionally substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$ or $C(O)R^b$;

cycloalkylY or heterocyclylY wherein cycloalkyl or heterocyclyl each optionally is substituted by one or more of the following: F, OH, CN, $NR^aR^a$, $OR^b$, $SR^b$, $S(O)R^b$, $SO_2R^b$, $C(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$ or $C(O)R^b$;

phenylY or heteroarylY wherein phenyl or heteroaryl each optionally is substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$ or $C(O)R^b$;

$R^2$ represents phenyl which is optionally substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$ or $C(O)R^b$.

Further aspect 3. A compound according to further aspect 2 or a pharmaceutically acceptable salt or solvate thereof, or a solvent of such a salt, wherein $R^1$ represents X which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$ or $NR^aC(O)NR^aR^a$.

Further aspect 4. A compound according to further aspect 3 or a pharmaceutically acceptable salt or solvate thereof, or a solvent of such a salt, wherein $R^1$ represents X which is optionally substituted by one or more of the following: F, OH, CN, $NR^aR^a$, $OR^b$, $SR^b$, $S(O)R^b$, $SO_2R^b$, $C(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$ or $C(O)R^b$.

Further aspect 5. A compound according to further aspect 1 or a pharmaceutically acceptable salt or solvate thereof, or a solvent of such a salt, wherein $R^3$ represents aryl or $Het^1$ wherein aryl or $Het^1$ each is substituted by one of the following: Q, $Het^2$, R or $Het^3$ and wherein aryl or $Het^1$ each is optionally substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

Further aspect 6. A compound according to further aspect 1 or a pharmaceutically acceptable salt or solvate thereof, or a solvent of such a salt, wherein $R^3$ represents aryl or $Het^1$ wherein aryl or $Het^1$ each optionally is substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, QZ, $Het^2Z$, RZ, $Het^3Z$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

Further aspect 7. A compound according to further aspect 1 or a pharmaceutically acceptable salt or solvate thereof, or a solvent of such a salt, wherein $R^3$ represents $Het^4$ or T wherein $Het^4$ or T each optionally is substituted on the aromatic ring by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, Q, $Het^2$, R, $Het^3$, QZ, $Het^2Z$, RZ, $Het^3Z$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$, and wherein $Het^4$ or T each optionally is substituted on the non-aromatic ring by one or more of the following: F, OH, CN, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, thioxo, Q, $Het^2$, R, $Het^3$, QZ, Het²Z, RZ, Het³Z, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

Further aspect 8. A compound according to further aspect 2 or a pharmaceutically acceptable salt or solvate thereof, or a solvent of such a salt, wherein $R^3$ represents aryl or $Het^1$ wherein aryl or $Het^1$ each is substituted by one of the following: Q, $Het^2$, R or $Het^3$ and wherein aryl or $Het^1$ each is optionally substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^a$-$C(O)NR^aR^a$, $SO_2NHC(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

Further aspect 9. A compound according to further aspect 2 or a pharmaceutically acceptable salt or solvate thereof, or a solvent of such a salt, wherein $R^3$ represents aryl or $Het^1$ wherein aryl or $Het^1$ each optionally is substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, QZ, Het²Z, RZ, Het³Z, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

Further aspect 10. A compound according to further aspect 2 or a pharmaceutically acceptable salt or solvate thereof, or a solvent of such a salt, wherein $R^3$ represents $Het^4$ or T wherein $Het^4$ or T each optionally is substituted on the aromatic ring by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, Q, $Het^2$, R, $Het^3$, QZ, Het²Z, RZ, Het³Z, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$, and wherein $Het^4$ or T each optionally is substituted on the non-aromatic ring by one or more of the following: F, OH, CN, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, thioxo, Q, $Het^2$, R, $Het^3$, QZ, Het²Z, RZ, Het³Z, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

Further aspect 11. A compound according to further aspect 3 or a pharmaceutically acceptable salt or solvate thereof, or a solvent of such a salt, wherein $R^3$ represents aryl or $Het^1$ wherein aryl or $Het^1$ each is substituted by one of the following: Q, $Het^2$, R or $Het^3$ and wherein aryl or $Het^1$ each is optionally substituted by one or more of the following: halogen (Cl, F, I, Br), OH, CN, $NO_2$, $NR^aR^a$, $OR^b$, $SR^b$$S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^a$-$C(O)NR^aR^a$, $SO_2NHC(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

Further aspect 12. A compound according to further aspect 3 or a pharmaceutically acceptable salt or solvate thereof, or a solvent of such a salt, wherein $R^3$ represents aryl or $Het^1$ wherein aryl or $Het^1$ each optionally is substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, QZ, Het²Z, RZ, Het³Z, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

Further aspect 13. A compound according to further aspect 3 or a pharmaceutically acceptable salt or solvate thereof, or a solvent of such a salt, wherein $R^3$ represents $Het^4$ or T wherein $Het^4$ or T each optionally is substituted on the aromatic ring by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, Q, $Het^2$, R, $Het^3$, QZ, Het²Z, RZ, Het³Z, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$, and wherein $Het^4$ or T each optionally is substituted on the non-aromatic ring by one or more of the following: F, OH, CN, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, thioxo, Q, $Het^2$, R, $Het^3$, QZ, Het²Z, RZ, Het³Z, or $C_1$-$C_4$alkyl which is optionally substituted by one or more of the following: F, OH, CN, NR$^a$R$^a$, OR$^b$, SR$^b$S(O)R$^b$, SO$_2$R$^b$C(O)R$^b$, C(O)NR$^a$R$^a$, NR$^a$C(O)R$^b$, C(O)OR$^a$, OC(O)R$^b$, NR$^a$SO$_2$R$^b$SO$_2$NR$^a$R$^a$, NR$^a$C(O)OR$^b$, OC(O)NR$^a$R$^a$ or NR$^a$C(O)NR$^a$R$^a$.

Further aspect 14. A compound according to further aspect 4 or a pharmaceutically acceptable salt or solvate thereof, or a solvent of such a salt, wherein R$^3$ represents aryl or Het$^1$ wherein aryl or Het$^1$ each is substituted by one of the following: Q, Het$^2$, R or Het$^3$ and wherein aryl or Het$^1$ each is optionally substituted by one or more of the following: halogen (Cl, F, I, Br), OH, CN, NO$_2$, NR$^a$R$^a$, OR$^b$, SR$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

Further aspect 15. A compound according to further aspect 4 or a pharmaceutically acceptable salt or solvate thereof, or a solvent of such a salt, wherein R$^3$ represents aryl or Het$^1$ wherein aryl or Het$^1$ each optionally is substituted by one or more of the following: halogen (Cl, F, I, Br), OH, CN, NO$_2$, NR$^a$R$^a$, OR$^b$, SR$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, QZ, Het$^2$Z, RZ, Het$^3$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

Further aspect 16. A compound according to further aspect 4 or a pharmaceutically acceptable salt or solvate thereof, or a solvent of such a salt, wherein R$^3$ represents Het$^4$ or T wherein Het$^4$ or T each optionally is substituted on the aromatic ring by one or more of the following: halogen (Cl, F, I, Br), OH, CN, NO$_2$, NR$^a$R$^a$, OR$^b$, SR$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, Q, Het$^2$, R, Het$^3$, QZ, Het$^2$Z, RZ, Het$^3$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$, and wherein Het$^4$ or T each optionally is substituted on the non-aromatic ring by one or more of the following: F, OH, CN, NR$^a$R$^a$, OR$^b$, SR$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, thioxo, Q, Het$^2$, R, Het$^3$, QZ, Het$^2$Z, RZ, Het$^3$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

Further aspect 17. A compound according to further aspect 1 in which R$^1$ is selected from methyl, ethyl, isopropyl, n-butyl, tert-butyl, 2-methoxyethyl, 6-aminopyridin-3-ylmethyl, 6-difluoromethoxyphenyl or 6-difluoromethoxybenzyl;

R$^2$ is selected from phenyl, 3-chlorophenyl, 4-chlorophenyl or 4-trifluoromethylphenyl; and R$^3$ is selected from 4-methoxyphenyl, 4-hydroxyphenyl, 4-isopropoxyphenyl, 4-difluoromethoxyphenyl, 4-trifluoromethoxyphenyl, 4-fluorophenyl, 4-hydroxymethylphenyl, 1-benzyloxyphenyl, 4-cyclohexylphenyl, 4-morpholin-4-ylphenyl, 4-piperidin-1-ylphenyl, 4-pyrrolidin-1-ylphenyl, 4-azepan-1-ylphenyl, 4-benzylpiperazin-1-ylphenyl, 4-(tertbutoxycarbonylamino)phenyl, 4-(N-acetylsulfonamide)phenyl, 2-dimethylaminocarbonyl-1-benzofuran-5-yl, 2-acetyl-1-benzofuran-5-yl, 2-tertbutoxycarbonyl-1-benzofuran-5-yl, 2-carboxy-1-benzofuran-5-yl, 1-benzofuran-5-yl, 2-ethoxycarbonyl-3-methyl-1-benzothiophene-5-yl, 1H-indol-5-yl, 6-morpholin-4-ylpyridin-3-yl, 6-methoxypyridin-3-yl, 5-cyclohexyl-2-methoxyphenyl, 3-chloro-4-morpholin-4-ylphenyl, 2,5-diethoxy-4-morpholin-4-ylphenyl, 2-acetyl-1,2,3,4-tetrahydroisoquinolin-6-yl, 2-methylaminocarbonyl-3,4-dihydroisoquinoline-2(1H)-6-yl, 1,2,3,4-tetrahydroisoquinolin-6-yl, 2-tertbutoxycarbonyl-3,4-dihydroisoquinoline-2(1H)-6-yl, 5,6,7,8-tetrahydronaphtalen-1-yl, 2-thioxo-2,3-dihydro-1,3-benzothiazol-6-yl, 1H-isoindole-1,3(2H)-dione-5-yl, 1H-benzimidazol-2-yl, 1H-1,2,4-triazol-3-yl, 3-morpholin-4-yl-1H-1,2,4-triazol-5-yl or 5-methyl-1-phenyl-pyrazol-3-yl.

Further aspect 18. A compound selected from one or more of the following:

2-tert-butyl-4-[(4-morpholin-4-ylphenyl)amino]-5-phenyl-isothiazol-3(2H)-one 1,1-dioxide 2-tert-butyl-4-[(4-methoxyphenyl)amino]-5-phenylisothiazol-3(2H)-one 1,1-dioxide 2-tert-butyl-5-phenyl-4-[(4-piperidin-1-ylphenyl)amino] isothiazol-3(2H)-one 1,1-dioxide 2-tert-butyl-4-[(4-isopropoxyphenyl)amino]-5-phenyl-isothiazol-3(2H)-one 1,1-dioxide 2-tert-butyl-5-phenyl-4-[(4-pyrrolidin-1-ylphenyl)amino] isothiazol-3(2H)-one 1,1-dioxide tert-butyl {4-[(2-tert-butyl-1,1-dioxido-3-oxo-5-phenyl-2,3-dihydroisothiazol-4-yl)amino]phenyl}carbamate 4-[(4-isopropoxyphenyl)amino]-2-isopropyl-5-phenyl-isothiazol-3(2H)-one 1,1-dioxide 2-isopropyl-5-phenyl-4-[(4-piperidin-1-ylphenyl)amino] isothiazol-3(2H)-one 1,1-dioxide 4-[(4-azepan-1-ylphenyl)amino]-2-tert-butyl-5-phenyl-isothiazol-3(2H)-one 1,1-dioxide 2-isopropyl-4-[(4-morpholin-4-ylphenyl)amino]-5-phenyl-isothiazol-3(2H)-one 1,1-dioxide 2-butyl-4-[(4-methoxyphenyl)amino]-5-phenylisothiazol-3(2H)-one 1,1-dioxide 4-[(2-acetyl-1-benzofuran-5-yl)amino]-2-butyl-5-phenyl-isothiazol-3(2H)-one 1,1-dioxide 2-tert-butyl-4-[(6-morpholin-4-ylpyridin-3-yl)amino]-5-phenylisothiazol-3(2H)-one 1,1-dioxide 2-butyl-4-{[4-(difluoromethoxy)phenyl]amino}-5-phenyl-isothiazol-3(2H)-one 1,1-dioxide 2-butyl-4-[(4-morpholin-4-ylphenyl)amino]-5-phenyl-isothiazol-3(2H)-one 1,1-dioxide tert-butyl 6-[(2-butyl-1,1-dioxido-3-oxo-5-phenyl-2,3-dihydroisothiazol-4-yl)amino]-3,4-dihydroisoquinoline-2(1H)-carboxylate 2-butyl-4-[(3-chloro-4-morpholin-4-ylphenyl)amino]-5-phenylisothiazol-3(2H)-one 1,1-dioxide
2-butyl-5-(3-chlorophenyl)-4-[(4-morpholin-4-ylphenyl)amino]isothiazol-3(2H)-one 1,1-dioxide
2-ethyl-4-[(4-morpholin-4-ylphenyl)amino]-5-phenylisothiazol-3(2H)-one 1,1-dioxide
4-[(2-acetyl-1,2,3,4-tetrahydroisoquinolin-6-yl)amino]-2-butyl-5-phenylisothiazol-3(2H)-one 1,1-dioxide
2-tert-butyl-4-[(4-methoxyphenyl)(methyl)amino]-5-phenylisothiazol-3(2H)-one 1,1-dioxide
2-butyl-4-[(4-hydroxyphenyl)amino]-5-phenylisothiazol-3(2H)-one 1,1-dioxide
2-butyl-4-(1H-indol-5-ylamino)-5-phenylisothiazol-3(2H)-one 1,1-dioxide
5-[(2-butyl-1,1-dioxido-3-oxo-5-phenyl-2,3-dihydroisothiazol-4-yl)amino]-N,N-dimethyl-1-benzofuran-2-carboxamide
2-[4-(difluoromethoxy)benzyl]-4-[(4-morpholin-4-ylphenyl)amino]-5-phenylisothiazol-3(2H)-one 1,1-dioxide
2-butyl-5-(3-chlorophenyl)-4-{[4-(difluoromethoxy)phenyl]amino}isothiazol-3(2H)-one 1,1-dioxide
2-butyl-5-phenyl-4-{[4-(trifluoromethoxy)phenyl]amino}isothiazol-3(2H)-one 1,1-dioxide
2-butyl-4-{[4-(hydroxymethyl)phenyl]amino}-5-phenylisothiazol-3(2H)-one 1,1-dioxide
4-{[4-(benzyloxy)phenyl]amino}-2-butyl-5-phenylisothiazol-3(2H)-one 1,1-dioxide
4-{[4-(4-benzylpiperazin-1-yl)phenyl]amino}-2-butyl-5-phenylisothiazol-3(2H)-one 1,1-dioxide
2-[4-(difluoromethoxy)benzyl]-4-[(4-methoxyphenyl)amino]-5-phenylisothiazol-3(2H)-one 1,1-dioxide
4-(1-benzofuran-5-ylamino)-2-butyl-5-phenylisothiazol-3(2H)-one 1,1-dioxide
2-butyl-5-(4-chlorophenyl)-4-{[4-(difluoromethoxy)phenyl]amino}isothiazol-3(2H)-one 1,1-dioxide
2-butyl-5-phenyl-4-(1H-1,2,4-triazol-3-ylamino)isothiazol-3(2H)-one 1,1-dioxide
2-butyl-4-[(5-methyl-1-phenyl-1H-pyrazol-3-yl)amino]-5-phenylisothiazol-3(2H)-one 1,1-dioxide
2-butyl-4-[(6-methoxypyridin-3-yl)amino]-5-phenylisothiazol-3(2H)-one 1,1-dioxide
4-[(2-acetyl-1-benzofuran-5-yl)amino]-2-(2-methoxyethyl)-5-phenylisothiazol-3(2H)-one 1,1-dioxide
2-[4-(difluoromethoxy)benzyl]-4-{[4-(difluoromethoxy)phenyl]amino}-5-phenylisothiazol-3(2H)-one 1,1-dioxide
2-butyl-5-phenyl-4-[(2-thioxo-2,3-dihydro-1,3-benzothiazol-6-yl)amino]isothiazol-3(2H)-one 1,1-dioxide
2-methyl-4-[(4-morpholin-4-ylphenyl)amino]-5-phenylisothiazol-3(2H)-one 1,1-dioxide
4-[(4-methoxyphenyl)amino]-2-methyl-5-phenylisothiazol-3(2H)-one 1,1-dioxide
4-[(4-cyclohexylphenyl)amino]-2-(2-methoxyethyl)-5-phenylisothiazol-3(2H)-one 1,1-dioxide
4-[(2-acetyl-1-benzofuran-5-yl)amino]-2-methyl-5-phenylisothiazol-3(2H)-one 1,1-dioxide
2-(2-methoxyethyl)-5-phenyl-4-(5,6,7,8-tetrahydronaphthalen-1-ylamino)isothiazol-3(2H)-one 1,1-dioxide
4-(1H-indol-5-ylamino)-2-(2-methoxyethyl)-5-phenylisothiazol-3(2H)-one 1,1-dioxide
4-[(4-fluorophenyl)amino]-2-methyl-5-phenylisothiazol-3(2H)-one 1,1-dioxide
2-[(6-aminopyridin-3-yl)methyl]-4-[(4-morpholin-4-ylphenyl)amino]-5-phenylisothiazol-3(2H)-one 1,1-dioxide
N-({4-[(2-butyl-1,1-dioxido-3-oxo-5-phenyl-2,3-dihydroisothiazol-4-yl)amino]phenyl}sulfonyl)acetamide
ethyl 5-[(2-butyl-1,1-dioxido-3-oxo-5-phenyl-2,3-dihydroisothiazol-4-yl)amino]-3-methyl-1-benzothiophene-2-carboxylate
5-[(2-butyl-1,1-dioxido-3-oxo-5-phenyl-2,3-dihydroisothiazol-4-yl)amino]-1-benzofuran-2-carboxylic acid
tert-butyl 5-[(2-butyl-1,1-dioxido-3-oxo-5-phenyl-2,3-dihydroisothiazol-4-yl)amino]-1-benzofuran-2-carboxylate
4-[(2-acetyl-1-benzofuran-5-yl)amino]-2-ethyl-5-[4-(trifluoromethyl)phenyl]isothiazol-3(2H)-one 1,1-dioxide
2-(2-methoxyethyl)-4-[(3-morpholin-4-yl-1H-1,2,4-triazol-5-yl)amino]-5-phenylisothiazol-3(2H)-one 1,1-dioxide
ethyl 5-{[2-(2-methoxyethyl)-1,1-dioxido-3-oxo-5-phenyl-2,3-dihydroisothiazol-4-yl]amino}-3-methyl-1-benzothiophene-2-carboxylate
4-[(5-cyclohexyl-2-methoxyphenyl)amino]-2-(2-methoxyethyl)-5-phenylisothiazol-3(2H)-one 1,1-dioxide
4-[(4-hydroxyphenyl)amino]-2-(2-methoxyethyl)-5-phenylisothiazol-3(2H)-one 1,1-dioxide
4-(1H-benzimidazol-2-ylamino)-2-butyl-5-phenylisothiazol-3(2H)-one 1,1-dioxide
2-[(6-aminopyridin-3-yl)methyl]-4-{[4-(difluoromethoxy)phenyl]amino}-5-phenylisothiazol-3(2H)-one 1,1-dioxide
2-methyl-4-[(6-morpholin-4-ylpyridin-3-yl)amino]-5-phenylisothiazol-3(2H)-one 1,1-dioxide
2-butyl-5-phenyl-4-(1,2,3,4-tetrahydroisoquinolin-6-ylamino)isothiazol-3(2H)-one 1,1-dioxide
5-[(2-butyl-1,1-dioxido-3-oxo-5-phenyl-2,3-dihydroisothiazol-4-yl)amino]-1H-isoindole-1,3(2H)-dione
2-butyl-4-[(2,5-diethoxy-4-morpholin-4-ylphenyl)amino]-5-phenylisothiazol-3(2H)-one 1,1-dioxide
2-(2-methoxyethyl)-4-[(4-morpholin-4-ylphenyl)amino]-5-phenylisothiazol-3(2H)-one 1,1-dioxide
4-{[4-(difluoromethoxy)phenyl]amino}-2-(2-methoxyethyl)-5-phenylisothiazol-3(2H)-one 1,1-dioxide
2-ethyl-4-[(4-morpholin-4-ylphenyl)amino]-5-[4-(trifluoromethyl)phenyl]isothiazol-3(2H)-one 1,1-dioxide
6-[(2-butyl-1,1-dioxido-3-oxo-5-phenyl-2,3-dihydroisothiazol-4-yl)amino]-N-methyl-3,4-dihydroisoquinoline-2(1H)-carboxamide
4-{[4-(difluoromethoxy)phenyl]amino}-2-methyl-5-phenylisothiazol-3(2H)-one 1,1-dioxide tert-butyl 6-[(2-butyl-1,1-dioxido-3-oxo-5-phenyl-2,3-dihydroisothiazol-4-yl)amino]-1-benzofuran-2-carboxylate, or a pharmaceutically acceptable salt or solvate thereof, or a solvate of such a salt.

Further aspect 19. A process for the preparation of a compound according to any one of further aspects 1-18, wherein $R^1$, $R^2$ or $R^3$ are as defined in claim 1, comprising the step of reacting
a compound of formula VI,

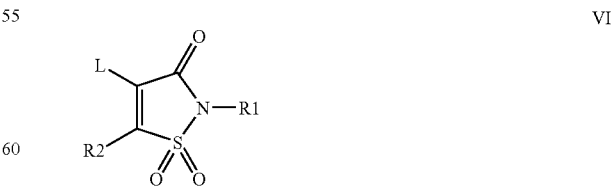

wherein $R^1$ and $R^2$ are as defined in claim 1 and L is a leaving group such as Cl, Br, I, methanesulfonate or trifluoromethanesulfonate, with a compound of formula VII, $R^3NH_2$           VII wherein R³ is as defined in claim 1, optionally in the presence of an inert organic solvent such as dimethylformamide.

Further aspect 20. A pharmaceutical formulation comprising a compound according to any one of further aspects 1-18 in admixture with pharmaceutically acceptable adjuvants, diluents and/or carriers.

Further aspect 21. A compound according to any one of further aspects 1-18 for use in therapy.

Further aspect 22. The use of a compound according to any of further aspects 1-18 for the manufacture of a medicament for the modulation of the nuclear hormone receptors LXR α and/or β.

Further aspect 23. The use of a compound according to any one of further aspects 1-18 in the manufacture of a medicament for the treatment and/or prophylaxis of cardiovascular disease.

Further aspect 24. The use of a compound according to any one of further aspects 1-18 in the manufacture of a medicament for the treatment and/or prophylaxis of atherosclerosis.

Further aspect 25. The use of a compound according to any one of further aspects 1-18 in the manufacture of a medicament for the treatment and/or prophylaxis of hypercholesterolemia.

Further aspect 26. The use of a compound according to any one of further aspects 1-18 in the manufacture of a medicament for the treatment and/or prophylaxis of conditions associated with a need for improving reverse cholesterol transport.

Further aspect 27. The use of a compound according to any one of further aspects 1-18 in the manufacture of a medicament for the treatment and/or prophylaxis of conditions associated with a need for decreasing intestinal cholesterol absorption.

Further aspect 28. The use of a compound according to any one of further aspects 1-18 in the manufacture of a medicament for the treatment and/or prophylaxis of conditions associated with a need for increasing HDL-cholesterol levels.

Further aspect 29. The use of a compound according to any one of further aspects 1-18 in the manufacture of a medicament for the treatment and/or prophylaxis of conditions associated with a need for decreasing LDL-cholesterol levels.

Further aspect 30. The use of a compound according to any one of further aspects 1-18 in the manufacture of a medicament for the treatment and/or prophylaxis of inflammatory conditions.

Further aspect 31. The use of a compound according to any one of further aspects 1-18 in the manufacture of a medicament for the treatment and/or prophylaxis of Alzheimer's disease.

Further aspect 32. The use of a compound according to any one of further aspects 1-18 in the manufacture of a medicament for the treatment and/or prophylaxis of arteriosclerosis.

Further aspect 33. The use of a compound according to any one of further aspects 1-18 in the manufacture of a medicament for the treatment and/or prophylaxis of type 2 diabetes.

Further aspect 34. The use of a compound according to any one of further aspects 1-18 in the manufacture of a medicament the treatment and/or prophylaxis of conditions associated with a need for improving HDL function.

Further aspect 35. The use of a compound according to any one of further aspects 1-18 in the manufacture of a medicament for the treatment and/or prophylaxis of lipid disorders (dyslipidemia) whether or not associated with insulin resistance.

Further aspect 36. A method of treating and/or preventing lipid disorders (dyslipidemia) whether or not associated with insulin resistance comprising the administration of a compound according to any one of further aspects 1-18 to a mammal in need thereof.

Further aspect 37. A method for treatment and/or prophylaxis of cardiovascular disease comprising administering to a mammal, including man, in need of such a treatment an effective amount of a compound as defined in any of further aspects 1-18.

Further aspect 38. A method of treating and/or preventing atherosclerosis comprising the administration of an effective amount of a compound of formula I according to any one of further aspects 1-18 to a mammal in need thereof.

Further aspect 39. A method for treatment and/or prophylaxis of hypercholesterolemia comprising administering to a mammal, including man, in need of such a treatment an effective amount of a compound as defined in any of further aspects 1-18.

Further aspect 40. A method for treatment and/or prophylaxis of conditions associated with a need for improving reverse cholesterol transport comprising administering to a mammal, including man, in need of such a treatment an effective amount of a compound as defined in any of further aspects 1-18.

Further aspect 41. A method for treatment and/or prophylaxis of conditions associated with a need for decreasing intestinal cholesterol absorption comprising administering to a mammal, including man, in need of such a treatment an effective amount of a compound as defined in any of further aspects 1-18.

Further aspect 42. A method for treatment and/or prophylaxis of conditions associated with a need for increasing HDL-cholesterol levels comprising administering to a mammal, including man, in need of such a treatment an effective amount of a compound as defined in any of further aspects 1-18.

Further aspect 43. A method for treatment and/or prophylaxis of conditions associated with a need for decreasing LDL-cholesterol levels comprising administering to a mammal, including man, in need of such a treatment an effective amount of a compound as defined in any of further aspects 1-18.

Further aspect 44. A method for treatment and/or prophylaxis of inflammatory conditions comprising administering to a mammal, including man, in need of such a treatment an effective amount of a compound as defined in any of further aspects 1-18.

Further aspect 45. A method for treatment and/or prophylaxis of Alzheimer's disease comprising administering to a mammal, including man, in need of such a treatment an effective amount of a compound as defined in any of further aspects 1-18.

Further aspect 46. A method for treatment and/or prophylaxis of arteriosclerosis comprising administering to a mammal, including man, in need of such a treatment an effective amount of a compound as defined in any of further aspects 1-18.

Further aspect 47. A method for treatment and/or prophylaxis of type 2 diabetes comprising administering to a mammal, including man, in need of such a treatment an effective amount of a compound as defined in any of further aspects 1-18.

Further aspect 48. A method for treatment and/or prophylaxis of conditions associated with a need for improving HDL function comprising administering to a mammal, including man, in need of such a treatment an effective amount of a compound as defined in any of further aspects 1-18.

For the further aspects 1-48 above the definitions mentioned hereinbefore or the following definitions shall apply:

The term "X" denotes a straight or branched, saturated or unsaturated alkyl group having 1 to 6 carbon atoms wherein said alkyl group may optionally be interrupted by O, S, S(O), $SO_2$, C(O), $NR^a$, OC(O), C(O)O, $NR^aC(O)$, $C(O)NR^a$, $SO_2NR^a$ or $NR^aSO_2$.

The term "Y" denotes a straight or branched, saturated or unsaturated alkyl group having 1 to 3 carbon atoms wherein said alkyl group binds to nitrogen in 2-position in the isothiazol-3(2H)-one 1,1-dioxide, and may optionally be interrupted or ended by O, S, S(O), $SO_2$, C(O), OC(O), C(O)O, $NR^cC(O)$, $C(O)NR^c$, $NR^c$ and/or Y is optionally substituted by one or more of the following: OH, F, CN, $NR^aR^a$, $C_1$-$C_4$alkyl, $OR^b$, $SR^b$, $S(O)R^b$ or $SO_2R^b$. In the definition of "Y" the term "ended by O, S, S(O), $SO_2$, C(O), OC(O), C(O)O, $NR^cC(O)$, $C(O)NR^c$, $NR^c$, $NR^c$" means that the alkyl group has as the last position O, S, S(O), $SO_2$, C(O), OC(O), C(O)O, $NR^cC(O)$, $C(O)NR^c$ or $NR^c$ before it binds further to phenyl, heteroaryl, cycloalkyl or heterocyclyl.

The term "Z" denotes a straight or branched, saturated or unsaturated alkyl group having 1 to 6 carbon atoms wherein said alkyl group binds to aryl, $Het^1$, $Het^4$ or T and one of the following: Q, $Het^2$, R or $Het^3$, and may optionally be interrupted or ended by O, S, S(O), $SO_2$, C(O), OC(O), C(O)O, $NR^aC(O)$, $C(O)NR^a$, $NR^a$, $SO_2NR^a$, $NR^aSO_2$, optionally consists only of one of the following: O, S, S(O), $SO_2$, C(O), OC(O), C(O)O, $NR^aC(O)$, $C(O)NR^a$, $NR^a$, $SO_2NR^a$, $NR^aSO_2$ and/or Z is optionally substituted by one or more of the following: OH, F, CN, $NR^cR^c$, $C(O)R^c$, $OR^b$, $SR^c$, S(O)$R^c$, $SO_2R^c$, phenyl, phenyl$C_1$-$C_3$alkyl, or $C_1$-$C_4$alkyl which is optionally substituted by one or more of the following: F, OH, $NR^aR^a$, $SR^b$, $S(O)R^b$, $SO_2R^b$, $OR^b$. In the definition of "Z" the term "ended by O, S, S(O), $SO_2$, C(O), OC(O), C(O)O, $NR^aC(O)$, $C(O)NR^a$, $NR^a$, $SO_2NR^a$, $NR^aSO_2$" means that the alkyl group has as the last position O, S, S(O), $SO_2$, C(O), OC(O), C(O)O, $NR^aC(O)$, $C(O)NR^a$, $NR^a$, $SO_2NR^a$ or $NR^aSO_2$ before it binds further to aryl, $Het^1$, $Het^4$, T, Q, $Het^2$, R or $Het^3$.

The term "Q" denotes a saturated or unsaturated non-aromatic monocyclic ring composed of 3, 4, 5, 6, 7, 8 carbon atoms, which is optionally substituted by one or more of the following: F, OH, CN, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, C(O)$OR^a$, OC(O)$R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$. Examples of such Q include but are not limited to but is not limited to cyclopropyl, cyclobutyl, cyclopentyl, cyclohexyl, cycloheptyl, cyclooctanyl, cyclobutenyl, cyclopentenyl, cyclohexenyl, cycloheptenyl, cyclooctenyl, cyclopentadienyl, cyclohexadienyl and cyclooctadienyl.

The term "R" denotes a phenyl group which is optionally substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$ (O)$R^bC(O)NR^aR^a$, $NR^aC(O)R^b$, C(O)$OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

The term "T" denotes a bicyclic aromatic or partly aromatic carbocyclic ring composed of 4, 5, 6, 7, 8, 9 or 10 carbon atoms. T binds to nitrogen in 4-position on the isothiazol-3(2H)-one 1,1-dioxide through the aromatic part of the bicyclic ring.

The term "$C_1$alkyl" denotes an alkyl group having 1 carbon atom. An example of said alkyl includes, but is not limited to, methyl.

The term "$C_1$-$C_3$alkyl" denotes a straight or branched, saturated or unsaturated alkyl group having 1 to 3 carbon atoms.

The term "$C_1$-$C_4$alkyl" denotes a straight or branched, saturated or unsaturated alkyl group having 1 to 4 carbon atoms.

The term "cycloalkyl" denotes a saturated or unsaturated non-aromatic monocyclic ring composed of 3, 4, 5, 6, 7, 8 carbon atoms, and includes but is not limited to cyclopropyl, cyclobutyl, cyclopentyl, cyclohexyl, cycloheptyl, cyclooctanyl, cyclobutenyl, cyclopentenyl, cyclohexenyl, cycloheptenyl, cyclooctenyl, cyclopentadienyl, cyclohexadienyl and cyclooctadienyl.

The term "heterocyclyl" denotes a saturated or unsaturated non-aromatic 3-8 membered monocyclic ring in which one or more of the atoms in the ring is an element other than carbon, for example nitrogen, oxygen or sulfur. The term "sulfur" shall be understood to include sulphoxide (S(O)) and sulphone ($SO_2$). The term "nitrogen" shall be understood to include nitrogen oxide (NO).

The term "heteroaryl" denotes an aromatic 3-8 membered monocyclic ring in which one or more of the atoms in the ring is an element other than carbon, for example nitrogen, oxygen and sulfur. The term "sulfur" shall be understood to include sulphoxide (S(O)) and sulphone ($SO_2$). The term "nitrogen" shall be understood to include nitrogen oxide (NO).

The term "aryl" denotes a phenyl group which binds to nitrogen in 4-position on the isothiazol-3(2H)-one 1,1-dioxide.

The term "$Het^1$" denotes an aromatic 3-10 membered monocyclic ring in which one or more of the atoms in the ring is an element other than carbon, for example nitrogen, oxygen and sulfur. The term "sulfur" shall be understood to include sulphoxide (S(O)) and sulphone ($SO_2$). The term "nitrogen" shall be understood to include nitrogen oxide (NO). $Het^1$ binds to nitrogen in 4-position on the isothiazol-3(2H)-one 1,1-dioxide.

The term "$Het^2$" denotes a saturated or unsaturated non-aromatic 3-10 membered monocyclic ring in which one or more of the atoms in the ring is an element other than carbon, for example nitrogen, oxygen or sulfur, and wherein the ring optionally is substituted by one or more of the following: F, OH, CN, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$. The term "sulfur" shall be understood to include sulphoxide (S(O)) and sulphone ($SO_2$). The term "nitrogen" shall be understood to include nitrogen oxide (NO).

The term "$Het^3$" denotes an aromatic 3-10 membered monocyclic ring in which one or more of the atoms in the ring is an element other than carbon, for example nitrogen, oxygen and sulfur, and which is substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, phenyl$C_1$alkyl, $C(O)NR^aR^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$N$^a$R$^a$, NR$^a$C(O)OR$^b$, OC(O)NR$^a$R$^a$ or NR$^a$C(O)NR$^a$R$^a$. The term "sulfur" shall be understood to include sulphoxide (S(O)) and sulphone (SO$_2$). The term "nitrogen" shall be understood to include nitrogen oxide (NO).

The term "Het$^4$" denotes an aromatic or partly aromatic 6-10 membered bicyclic ring in which one or more of the atoms in the ring optionally is an element other than carbon, for example nitrogen, oxygen and sulfur. Het$^4$ binds to nitrogen in 4-position on the isothiazol-3(2H)-one 1,1-dioxide through the aromatic part of the bicyclic ring. The term "sulfur" shall be understood to include sulphoxide (S(O)) and sulphone (SO$_2$). The term "nitrogen" shall be understood to include nitrogen oxide (NO).

R$^a$ independently represents H or a straight or branched, saturated or unsaturated C$_1$-C$_4$alkyl chain optionally substituted by one or more F.

R$^b$ independently represents a straight or branched, saturated or unsaturated C$_1$-C$_4$alkyl chain optionally substituted by one or more F.

R$^c$ independently represents H or a straight or branched, saturated or unsaturated C$_1$-C$_3$alkyl chain optionally substituted by one or more F.

The invention is illustrated, but not limited, by the following Examples.

The naming of the compounds in this patent application was made either using a program from ACD Labs (version 6.0/Name, 6.0 Name Batch or labs 8.0/Name) or using the function Autonom 2000 Name in the program Isis Draw.

EXAMPLES

| Abbreviations | |
|---|---|
| AcOH | acetic acid |
| DCM | dichloromethane |
| DMF | N,N'-dimethylformamide |
| DMSO | dimethylsulfoxide |
| EDC | 1-ethyl-3-(3-dimethylaminopropyl)carbodiimide hydrochloride |
| EtOAc | ethyl acetate |
| EtOH | ethanol |
| HOBt | 1H-1,2,3-benzotriazole-1-ol |
| HPFC | high performance flash chromatography |
| HPLC | high performance liquid chromatography |
| LC-MS | liquid chromatography mass spectroscopy |
| MeCN | acetonitrile |
| MeOH | methanol |
| NMR | nuclear magnetic resonance |
| TEA | triethylamine |
| TFA | trifluoroacetic acid |
| THF | tetrahydrofuran |
| UV | ultra violet |
| rt | room temperature |
| h | hour(s) |
| mins | minutes |
| b | broad |
| bs | broad singlet |
| d | doublet |
| dd | double doublet |
| m | multiplet |
| s | singlet |
| t | triplet |

General Experimental Procedures

Phase Separator from IST was used. Flash column chromatography employed normal phase silica gel 60 (0.040-0.063 mm, Merck) or IST Isolute®SPE columns normal phase silica gel or Biotage Horizon HPFC System or a Horizon TM flash system using silica FLASH+HPFC Cartridges. HPLC purifications were performed on either a Gilson preparative HPLC system with a UV triggered fraction collector, equipped with an ACE C8 5 μm 250 mm×20 mm column, or a Kromasil C18 column, or on a Waters preparative HPLC system equipped with a Kromasil C8 10 μm 250 mm×21.2 mm column, or on a Waters preparative HPLC system equipped with an ACE C8 5 μm 250 mm×50 mm column or an ACE C8 5 μm 250 mm×20 mm column, or on a Waters FractionLynx HPLC system with a mass triggered fraction collector, equipped with a ACE C8 5 μm 100 mm×21.2 mm column; using MeCN/NH$_4$OAc buffer system with a gradient from 100% mobilphase A (5% MeCN+95% 0.1 M NH$_4$OAc) to 100% mobilphase B (100% MeCN) unless otherwise stated. $^1$H NMR and $^{13}$C NMR measurements were performed on a BRUKER ACP 300 or on a Varian Unity Plus 400, 500 or 600 spectrometer, operating at $^1$H frequencies of 300, 400, 500, 600 MHz, respectively, and $^{13}$C frequencies of 75, 100, 125 and 150 MHz, respectively. Chemical shifts are given in δ values (ppm) with the solvents used as internal standard, unless otherwise stated. Microwave heating was performed using single node heating in a Smith Creator or Emrys Optimizer from Personal Chemistry, Uppsala, Sweden. Mass spectral data were obtained using a Micromass LCT or Waters Q-T of micro system and, where appropriate, either positive ion data or negative ion data were collected.

Pyridine N-oxides are prepared by oxidizing the corresponding pyridine compounds with an oxidizing agent such as metachloroperbenzoic acid (MCPBA) in an inert organic solvent such as DCM at rt for 2-24 h.

Synthesis

Starting Material and Intermediates

N-(tert-Butyl)-1-phenylmethanesulfonamide

The title compound can be prepared as described in the reference below: Org. Biomol. Chem., 2003, 19, 3390-3395

2-tert-Butyl-4-hydroxy-5-phenylisothiazol-3(2H)-one 1,1-dioxide

Potassium tert-butoxide (0.845 g, 10.56 mmol) was added to a solution of N-(tert-butyl)-1-phenylmethanesulfonamide (1.2 g, 5.28 mmol) and diethyl oxalate (0.85 mL, 6.33 mmol) in THF (8 mL) and the mixture was heated at 150° C. for 15 mins in a microwave reactor. The reaction mixture was acidified with 1M HCl, the THF was evaporated and the residue was extracted with DCM. The mixture was evaporated, the residue was triturated in petroleum ether and the solvent was decanted to give the title compound (7 g, 63%) as a solid; $^1$H NMR (500 MHz, CDCl$_3$): δ 7.44-7.32 (m, 5H), 3.90 (br s, 1H), 1.36 (s, 9H); Mass Spectrum: M−H$^+$280

2-tert-Butyl-4-chloro-5-phenylisothiazol-3(2H)-one 1,1-dioxide

Oxalyl chloride (3.39 g, 2.71 mmol) was added dropwise to a solution of 2-tert-butyl-4-hydroxy-5-phenylisothiazol-3 (2H)-one 1,1-dioxide (5 g, 17.77 mol) and DMF (15 mL) in DCM (220 mL) at 0° C. The reaction mixture was then heated at 50° C. for 4 h, concentrated and the residue was diluted with EtOAc and washed with water, then brine and evaporated. The residue was purified by silica gel column chromatography, using a 98:2 mixture of petroleum ether and EtOAc as eluant. The product containing fractions were evaporated, the residue was triturated in petroleum ether and the solvent was decanted to give the title compound (3.9 g, 74%) as a solid; $^1$H NMR (500 MHz, CDCl$_3$): δ 7.97-7.92 (m, 2H), 7.61-7.51 (m, 3H), 1.75 (s, 9H); $^{13}$C NMR (125 MHz, CDCl$_3$): δ 156.5, 142.8, 132.3, 129.3, 128.8, 123.4, 63.0, 27.7.

N-Ethyl-1-phenylmethanesulfonamide

The title compound can be prepared as described in the reference below: Orazi, Orfeo O.; Corral, Renee A.; Bravo, Rodolfo; J. Heterocycl. Chem.; 23; 1986; 1701-1708.

2-Ethyl-4-hydroxy-5-phenylisothiazol-3(2H)-one 1,1-dioxide

N-Ethyl-1-phenylmethanesulfonamide (20 g) was divided into batches of 0.5 g each and taken in an 8 mL vial. To each vial was added potassium tert-butoxide (0.426 g, 3.8 mmol), ethyl oxalate (0.408 mL, 3.01 mmol) and dry THF (4 mL). Each vial was heated in a microwave reactor at 145° C. under pressure for 20 mins. Reaction mixture from all the vials were combined and treated with 1.5 N HCl (75 mL) and extracted with EtOAc. The organic layer was washed with water (3×25 mL) and brine, dried over Na$_2$SO$_4$ and evaporated. A small amount of the DCM was added to the solid residue and stirred well. Filtration gave nearly pure title compound (21 g, 82.6%) as off-white solid; $^1$H NMR (300 MHz, CDCl$_3$) δ 1.47 (t, 3H, J=7.2 Hz), 3.8 (q, 2H, J=7.2 Hz), 7.3-7.5 (m, 3), 7.9-8.0 (m, 2H).

4-Chloro-2-ethyl-5-phenylisothiazol-3(2H)-one 1,1-dioxide

2-Ethyl-4-hydroxy-5-phenylisothiazol-3(2H)-one 1,1-dioxide (5 g, 19.76 mmol) was dissolved in dry DCM (250 mL) and cooled to 0° C. under N$_2$. Dry DMF (15 mL) was added, followed by oxalyl chloride (3 mL, 34.4 mmol). The ice-bath was removed and the mixture was refluxed at 50° C. under N$_2$ for 4 h. The reaction mixture was evaporated and the residue was diluted with EtOAc and washed with water (3×25 mL) and brine, dried over Na$_2$SO$_4$ and evaporated. Another (16 g, 63.24 mmol) of 2-ethyl-4-hydroxy-5-phenylisothiazol-3 (2H)-one 1,1-dioxide was dissolved in dry DCM (500 mL) and cooled to 0° C. under N$_2$. Dry DMF (20 mL) was added followed by oxalyl chloride (9 mL, 103.2 mmol). The ice-bath was removed and the mixture was refluxed at 50° C. under N$_2$ for 4 h. The reaction mixture was evaporated and the residue was diluted with EtOAc and washed with water (3×50 mL) and brine, dried over Na$_2$SO$_4$ and evaporated where by red solid was obtained. The crude material from both batches were combined and purified by column chromatography on silica gel using 2.5-3% EtOAc in petroleum ether as eluant, and recrystallised from MeOH to give the title compound (15.7 g, 70%) as a white solid; $^1$H NMR (400 MHz, CD$_3$OD) δ 1.42 (t, 3H, J=7.3 Hz), 3.84 (q, 2H, J=7.3 Hz), 7.6-7.7 (m, 3H), 7.9-8.0 (m, 2H); Mass Spectrum: M+H$^+$ 272.

N-Butyl-1-phenylmethanesulfonamide

The title compound can be prepared as described in the reference below: Heterocycles, 1993, 36(4), 733-742

2-Butyl-4-hydroxy-5-phenylisothiazol-3(2H)-one 1,1-dioxide

N-Butyl-1-phenylmethanesulfonamide (2.0 g, 8.80 mmol) was dissolved in dry DMF (13 mL) under an atmosphere of nitrogen. Diethyl oxalate (1.44 g, 9.83 mmol) was added and the reaction mixture was cooled to 0° C. using an ice-bath. Potassium tert-butoxide (1.25 g, 11.14 mmol) was added in one portion and the reaction mixture was stirred for 5 mins at 0° C., followed by 19 h at rt. The mixture was cooled in an ice-bath and HCl (2M) was carefully added to give a pH~1 of the mixture. Most of the solvents were evaporated and the residue was partitioned between HCl (2M) and EtOAc. The combined organic layers were washed with water several times, dried over MgSO$_4$ and evaporated to dryness. The residue was purified using preparative HPLC (ACE C8, 0.1M NH$_4$OAc/MeCN, gradient) to give the title compound (0.96 g, 39%); $^1$H NMR (400 MHz, DMSO-d$_6$): δ 7.88-7.83 (m, 2H), 7.22-7.29 (m, 3H), 7.14 (bs, 1H), 6.98-7.15 (m, 2H), 3.48 (t, 2H), 1.59-1.67 (m, 2H), 1.27-1.37 (m, 2H), 0.88 (t, 3H); $^{13}$C NMR (100 MHz, DMSO-d$_6$): δ 163.1, 158.4, 132.3, 128.7, 124.2, 123.2, 37.8, 30.9, 20.2, 14.1; Mass Spectrum: M−H$^+$ 280.

2-Butyl-4-chloro-5-phenylisothiazol-3(2H)-one 1,1-dioxide

2-Butyl-4-hydroxy-5-phenylisothiazol-3(2H)-one 1,1-dioxide (444 mg, 1.58 mmol) was dissolved in dry DCM (15 mL) at rt and under an atmosphere of nitrogen. Oxalyl chloride (0.15 mL, 1.73 mmol) was added dropwise and the reaction mixture was refluxed for 1.5 h. DMF (0.08 mL) was added followed by oxalyl chloride (0.15 mL, 1.73 mmol) in 2 portions and the reaction mixture was refluxed for another 6 h. The solvents were evaporated and the residue was partitioned between water and DCM. The combined organic layers were washed with water and the two phases were separated using a phase separator. Evaporation of the organic phase gave the title compound (440 mg, 88%) as a brown oil with approximately 95% purity according to $^1$H-NMR and was used without further purification; $^1$H-NMR (400 MHz, CDCl$_3$): δ 7.96-8.00 (m, 2H), 7.53-7.62 (m, 3H), 3.74-3.80 (t, 2H), 1.78-1.87 (m, 2H), 1.39-1-50 (m, 2H), 0.98 (t, 3H); $^{13}$C-NMR (100 MHz, CDCl$_3$): δ 156.3, 137.1, 132.7, 129.6, 129.2, 127.6, 123.7, 40.9, 30.1, 20.1, 13.7.

N-Butyl-1-(3-chlorophenyl)methanesulfonamide

A solution of (3-chlorophenyl)methanesulfonyl chloride (3.00 g, 13.33 mmol) in dry THF (50 mL) was added dropwise to a solution of butylamine (2.63 mL, 26.65 mmol) in dry THF (50 mL) at 0° C. and under an atmosphere of nitrogen. After the addition was completed the ice-bath was removed and the mixture was stirred at rt for 1.5 h. It was evaporated and the residue was partitioned between DCM and HCl (1M). The combined organic layers were washed with water, dried with MgSO$_4$ and evaporated to dryness to give the title compound (2.89 g, 83%) as a white powder; $^1$H NMR (500 MHz, CDCl$_3$): δ 7.29-7.42 (m, 4H), 4.22 (s, 2H), 4.16 (bs, 1H), 2.99-3.05 (m, 2H), 1.46-1.53 (m, 2H), 1.29-1.38 (m, 2H), 0.92 (t, 3H); $^{13}$C NMR (125 MHz, CDCl$_3$): δ 132.2, 129.0, 128.3, 127.7, 126.6, 126.4, 55.9, 41.2, 30.0, 17.3, 11.21; Mass Spectrum: M−H$^+$ 260.

2-Butyl-5-(3-chlorophenyl)-4-hydroxyisothiazol-3(2H)-one 1,1-dioxide

Diethyl oxalate (0.37 mL, 2.75 mmol) was added to a solution of N-butyl-1-(3-chlorophenyl)methanesulfonamide (600 mg, 2.29 mmol) in dry THF (4 mL) at rt under an atmosphere of nitrogen. The mixture was cooled in an ice-bath and potassium tert-butoxide (386 mg, 3.44 mmol) was added. The mixture was stirred at 0° C. for 1 h and then at rt for 1 h.

Finally, the mixture was heated in a microwave reactor at 150° C. for 10 mins followed by additional 5 mins at 150° C. The reaction mixture was cooled in an ice-bath and HCl (2 mL, 2M) was added. It was evaporated and the residue was extracted three times with DCM. The combined organic layers were dried with $MgSO_4$ and evaporated to give a slightly beige crude solid product. The crude product was dried in vacuum for 2 days to give the title compound (0.697 g, 96%) as a beige solid with about 90% purity according to $^1$H-NMR. The product was used without further purification; $^1$H NMR (500 MHz, $CDCl_3$): δ 7.93 (bs, 1H), 7.77-7.82 (m, 1H), 7.39-7.47 (m, 2H), 3.78 (t, 2H), 1.81-1.89 (m, 2H), 1.42-1-53 (m, 2H), 1.00 (t, 3H); $^{13}$C NMR (100 MHz, $CDCl_3$): δ 158.5, 142.9, 135.3, 130.4, 130.2, 127.6, 126.0, 125.6, 118.0, 40.3, 30.2, 19.9, 13.4; Mass Spectrum: M–H$^+$ 315.

2-Butyl-4-chloro-5-(3-chlorophenyl)isothiazol-3(2H)-one 1,1-dioxide

Dry DMF (0.17 mL, 2.21 mmol) was added to a solution of 2-butyl-5-(3-chlorophenyl)-4-hydroxyisothiazol-3(2H)-one 1,1-dioxide (697 mg, 2.21 mmol) in dry DCM (15 mL) at rt and under an atmosphere of nitrogen. Oxalyl chloride (0.37 mL, 4.41 mmol) was added dropwise and the mixture was heated to reflux for 2.5 h. The reaction mixture was evaporated to dryness. The residue was dissolved in EtOAc and it was washed with several portions of water, dried with $MgSO_4$, and evaporated to give the title compound (685 mg, 84%) as a brown oil which was used without further purification; $^1$H NMR (500 MHz, $CDCl_3$): δ 7.96 (t, 1H), 7.84-7.88 (m, 1H), 7.57-7.61 (m, 1H), 7.50-7.55 (t, 1H), 3.79 (t, 2H), 1.80-1.87 (m, 2H), 1.39-1.51 (m, 2H), 1.00 (t, 3H); $^{13}$C NMR (125 MHz, $CDCl_3$): δ 161.5, 155.9, 142.4, 135.8, 132.8, 131.0, 129.0, 127.3, 125.1, 41.0, 30.4, 20.1, 13.7.

N-Ethyl-1-[4-(trifluoromethyl)phenyl]methanesulfonamide

[[4-(Trifluoromethyl)phenyl]methyl]sulfonyl chloride (0.60 g, 2.32 mmol) was added dropwise to a saturated solution of ethylamine in THF (10 mL). The mixture was stirred at room temperature for 1 h. It was evaporated and the residue was dissolved in DCM and the resulting mixture was washed with 5% HCl, dried and evaporated to give the title compound (0.49 g, 79%) as a solid; $^1$H NMR (500 MHz, $CDCl_3$): δ 7.68 (d, 2H), 7.55 (d, 2H), 4.32 (s, 2H), 4.01 (bs, 1H), 3.08-3.14 (m, 2H), 1.19 (t, 3H); Mass Spectrum: M–H$^+$ 265.

2-Ethyl-4-hydroxy-5-[4-(trifluoromethyl)phenyl]isothiazol-3(2H)-one 1,1-dioxide Potassium tert-butoxide (0.309 g, 1.83 mmol) was added to a solution of N-ethyl-1-[4-(trifluoromethyl)phenyl]methanesulfonamide (0.49 g, 1.83 mmol) and diethyl oxalate (0.322 g, 2.20 mmol) in THF (4 mL) at 0° C. The mixture was heated in a microwave reactor at 150° C. for 10 mins. HCl (1M, 2 mL) was added dropwise to the mixture at 0° C. It was evaporated and the residue was extracted with DCM. The organic layer was dried and evaporated to give the title compound (0.480 g, 81%) as a solid; $^1$H NMR (500 MHz, $CDCl_3$): δ 8.05 (d, 2H), 7.77 (d, 2H), 3.87 (q, 2H), 1.49 (t, 3H); Mass Spectrum: M–H$^+$ 320.

4-Chloro-2-ethyl-5-[4-(trifluoromethyl)phenyl]isothiazol-3(2H)-one 1,1-dioxide Oxalyl chloride (0.379 g, 2.99 mmol) was added dropwise to a solution of 2-ethyl-4-hydroxy-5-[4-(trifluoromethyl)phenyl]isothiazol-3(2H)-one 1,1-dioxide (0.480 g, 1.49 mmol) and DMF (0.109 g, 1.49 mmol) in DCM (12 mL). The mixture was refluxed for 1 h. It was evaporated and water was added. The resulting mixture was extracted with EtOAc, and the combined organic layers were washed with brine and evaporated to give the title compound (0.306 g, 71%) as a solid; $^1$H NMR (500 MHz, DMSO-$d_6$): δ 8.07-8.11 (m, 4H), 3.81 (q, 2H), 1.33 (t, 3H).

N-Butyl-1-(4-chlorophenyl)methanesulfonamide n-Butylamine (3.25 g, 44.43 mmol) was dissolved in THF (25 mL) and it was then cooled in an ice-bath. ((4-Chlorophenyl)methyl)sulfonyl chloride (5.0 g, 22.21 mmol) in THF (25 mL) was dropped in. The cooling-bath was removed after the addition. The mixture was stirred for 2 h and then evaporated to dryness. DCM (50 mL) was added to the residue. It was washed with HCl (5%, 10 mL), water (30 mL×3) and brine (20 mL), dried ($MgSO_4$) and evaporated to give the title compound (5.43 g, 93%) as a solid; $^1$H NMR (400 MHz, $CDCl_3$): δ 7.36 (d, 2H), 7.32 (d, 2H), 4.19 (s, 2H), 4.11 (bt, 1H), 2.99 (dd, 2H), 1.50-1.43 (m, 2H), 1.36-1.26 (m, 2H), 0.90 (t, 3H); Mass Spectrum: M–H$^+$ 260.

2-Butyl-5-(4-chlorophenyl)-4-hydroxyisothiazol-3(2H)-one 1,1-dioxide

The reaction was done in two vials. In each vial: N-butyl-1-(4-chlorophenyl)methanesulfonamide (0.5 g, 1.91 mmol) was dissolved in THF (3 mL). Ethyl oxalate (0.335 g, 2.29 mmol) was added. The mixture was cooled in an ice-bath. Potassium tert-butoxide (0.28 g, 2.48 mmol)) was added under nitrogen atmosphere. The mixture was heated in a microwave reactor at 150° C. for 10 mins. It was then cooled in an ice-bath. HCl (10%, ca.1 mL) was added, pH~1. The mixtures of the two vials were combined and evaporated to remove THF. It was then extracted with DCM (20 mL). The extract was dried ($MgSO_4$) and evaporated. Column chromatography (ISOLUTE SI, 20 g/70 mL) of the residue, eluting with heptane, then EtOAc:heptane (20:80), gave fraction A (0.9 g, containing ca. 60% of the title compound) and fraction B (0.035 g, the title compound). $^1$H NMR (400 MHz, THF-$d_8$): δ 7.92 (d, 2H), 7.50 (d, 2H), 3.68 (t, 2H), 1.82-1.76 (m, 2H), 1.49-1.39 (m, 2H), 0.97 (t, 3H). $^{13}$C NMR (100 MHz, THF-$d_8$): 159.2, 146.7, 135.4, 129.8, 129.4, 125.6, 117.7, 39.8, 31.2, 20.6, 13.7. Mass Spectrum: M–H$^+$ 314.

2-Butyl-4-chloro-5-(4-chlorophenyl)isothiazol-3(2H)-one 1,1-dioxide

2-Butyl-5-(4-chlorophenyl)-4-hydroxyisothiazol-3(2H)-one 1,1-dioxide (0.9 g, ca. 60%, 1.71 mmol) was dissolved in DCM (50 mL). DMF (0.13 mL) was added. Under nitrogen atmosphere, oxalyl chloride (0.434 g, 3.42 mmol) was dropped in. The mixture was then heated to reflux for 2 h and then evaporated to dry. Water (30 mL) was added into the residue. It was then extracted with DCM (20 mL×3). The extracts were combined and washed with water (50 mL×3) and brine (20 mL), dried (MgSO$_4$) and evaporated. The residue was then purified by column chromatography (ISOLUTE SI, 20 g/70 mL), eluting with DCM:heptane (25:75), to give the title compound (0.496 g, 87%); $^1$H NMR (400 MHz, CDCl$_3$): δ 7.93 (d, 2H), 7.54 (d, 2H), 3.76 (t; 2H), 1.85-1.77 (m, 2H), 1.48-1.39 (m, 2H), 0.98 (t, 3H); $^{13}$C NMR (100 MHz, CDCl$_3$): δ 155.8, 142.4, 139.0, 130.2, 129.9, 127.7, 121.8, 40.8, 30.2, 19.9, 13.4.

N-(2-Methoxyethyl)-1-phenylmethanesulfonamide

Phenylmethanesulfonyl chloride (3.0 g, 15.7 mmol) was dissolved in dry THF (15 mL) and it was added dropwise to a solution of 2-methoxyethylamine (2.36 g, 31.5 mmol) in dry THF (50 mL) at 0° C. After addition the ice-bath was removed and the reaction was stirred at rt for 2.5 h. The solvent was removed in vacuo and the residue was dissolved in DCM. The mixture was washed with one portion of 5% aqueous HCl, several portions of water, dried through a phase separator and evaporated to give the title compound (3.58 g, 94%); $^1$H NMR (400 MHz, CDCl$_3$): δ 7.43-7.35 (m, 5H), 4.52 (br s, 1H), 4.26 (s, 2H), 3.40 (t, 2H), 3.32 (s, 3H), 3.14-3.09 (m, 2H); Mass Spectrum: M−H$^+$ 228.

4-Hydroxy-2-(2-methoxyethyl)-5-phenylisothiazol-3 (2H)-one 1,1-dioxide

A solution of N-(2-methoxyethyl)-1-phenylmethanesulfonamide (3.5 g, 14.5 mmol) and diethyl oxalate (2.33 g, 16.0 mmol) in dry DMF was cooled in an ice-bath. Potassium tert-butoxide (2.17 g, 18.4 mmol) was added and after 5 min the ice-bath was removed and the reaction was stirred at rt for 22 h. HCl (2M, 45 mL) was added to the mixture and the acidic solution was extracted 3 times with DCM. The combined organic layer was washed 4 times with water, dried through a phase separator and evaporated. The residue was purified by preparative HPLC [0.1M N OAc/MeCN, gradient A:B (9:1 to 1:9)] to give the title compound (0.250 g, 6%) as a solid; $^1$H NMR (500 MHz, CD$_3$OD): δ 7.90-7.94 (m, 2H), 7.28-7.33 (m, 2H), 7.10-7.15 (m, 1H), 3.79 (t, 2H), 3.68 (t, 2H), 3.34 (s, 3H); Mass Spectrum: M−H$^+$ 282.

4-Chloro-2-(2-methoxyethyl)-5-phenylisothiazol-3 (2H)-one 1,1-dioxide

Oxalyl chloride (0.185 g, 1.46 mmol) was added dropwise to a solution of 4-hydroxy-2-(2-methoxyethyl)-5-phenyl-isothiazol-3(2H)-one 1,1-dioxide (0.250 g, 0.88 mmol) in DCM (15 mL). The mixture was refluxed for 2 days and then evaporated. The residue was dissolved in water and extracted 3 times with DCM. The combined organic layer was washed 2 times with water, dried through a phase separator and evaporated to give the title compound (0.245 g, 92%) as a solid; $^1$H NMR (500 MHz, CD$_3$OD): δ 7.94-7.97 (m, 2H), 7.58-7.67 (m, 3H), 3.94 (t, 2H), 3.70 (t, 2H), 3.38 (s, 3H).

N-[4-(Difluoromethoxy)benzyl]-1-phenylmethanesulfonamide 4-(Difluoromethoxy)benzyl amine (1.73 g, 9.97 mmol) was dissolved in THF (10 mL). It was cooled in an ice-bath. Under nitrogen atmosphere, triethylamine (1.46 mL, 10.46 mmol) was added and then benzylsulfonyl chloride (1.9 g, 9.97 mmol) in THF (10 mL) was dropped in. The cooling bath was removed after the addition. The mixture was stirred for 3 h and then evaporated to dryness. DCM (50 mL) was added to the residue. It was then washed with 1% HCl (15 mL), water (50 mL×3) and brine, dried (MgSO$_4$) and evaporated to give the title compound (3.01 g. 92%) as a solid; $^1$H NMR (400 MHz, CDCl$_3$): δ 7.32-7.40 (m, 5H), 7.26 (d, 2H), 7.09 (d, 2H), 6.49 (t, 1H), 4.36 (bt, 1H), 4.24 (s, 2H), 4.10 (d, 2H); Mass Spectrum: M−H$^+$ 326.

2-[4-(Difluoromethoxy)benzyl]-4-hydroxy-5-phenyl-isothiazol-3(2H)-one 1,1-dioxide N-[4-(Difluoromethoxy)benzyl]-1-phenylmethane-sulfonamide (0.6 g, 1.83 mmol) and ethyl oxalate (0.32 g, 2.20 mmol) were mixed in THF (4 mL, dry). Under an atmosphere of nitrogen, potassium tert-butoxide (0.27 g, 2.38 mmol) was added and the reaction mixture was heated in a microwave reactor at 150° C. for 10 mins and then at 150° C. for 5 mins. The mixture was then cooled in an ice-bath and HCl (10%, 1 mL) was added, pH~1. The mixture was evaporated to remove THF and the residue was extracted with DCM (20 mL). The extract was dried (MgSO$_4$) and evaporated to give the crude product (0.634 g). It was used in the next step without further purification.

4-Chloro-2-[4-(difluoromethoxy)benzyl]-5-phenyl-isothiazol-3(2H)-one 1,1-dioxide 2-[4-(Difluoromethoxy)benzyl]-4-hydroxy-5-phenyl-isothiazol-3(2H)-one 1,1-dioxide (0.98 g, ca.60% purity, 1.80 mmol)) was dissolved in DCM (40 mL) and DMF (0.14 mL) was added. Under an atmosphere of nitrogen, oxalyl chloride (0.46 g 3.61 mmol) was dropped in. The mixture was then heated to reflux for 5 h and then evaporated to dryness. Water (20 mL) was added and the reaction mixture was extracted with DCM (20 mL×3). The extracts were combined and washed with water (50 mL×3) and brine (20 mL), dried (MgSO$_4$) and evaporated. The residue was purified by column chromatography (ISOLUTE SI, 20 g/70 mL), eluting with DCM:heptane (30:70), to give the title compound (0.442 g, 62%) as a semi-solid; $^1$H NMR (400 MHz, CDCl$_3$): δ 7.97 (d, 2H), 7.48-7.58 (m, 5H), 7.11 (d, 2H), 6.51 (t, 1H), 4.86 (s, 2H); $^{13}$C NMR (100 MHz, CDCl$_3$): δ 155.8, 151.2, 143.5, 132.5, 130.8, 130.5, 129.4, 128.8, 127.2, 123.2, 119.5, 115.7 (t), 43.1.

N-Isopropyl-1-phenylmethanesulfonamide

The title compound can be prepared as described in the reference below: Orazi, Orfeo O.; Corral, Renee A.; Bravo, Rodolfo; J. Heterocycl. Chem.; 23; 1986; 1701-1708.

4-Chloro-2-isopropyl-5-phenylisothiazol-3(2H)-one 1,1-dioxide

Step A. Methyl[(benzylsulfonyl)(isopropyl)amino](oxo)acetate

A mixture of N-isopropyl-1-phenylmethanesulfonamide (1.0 g, 4.7 mmol) and methyl oxalyl chloride (2.0 mL, 21.6 mmol) was heated at 120° C. for 1 h. Evaporation gave methyl [(benzylsulfonyl)(isopropyl)amino](oxo)acetate which was used directly in the next step without any purification.

Step B. 4-Hydroxy-2-isopropyl-5-phenylisothiazol-3(2H)-one 1,1-dioxide

Potassium tert-butoxide (1.5 g, 13.4 mmol) was added to a solution of crude methyl[(benzylsulfonyl)(isopropyl)amino] (oxo)acetate (2.0 g, 21.6 mmol) in DMF (15 mL).

After 17 h the mixture was evaporated and the residue was purified by silica gel column chromatography using a 4:1 mixture of EtOAc and MeOH as eluant, to give the title compound (0.5 g, 40%) as a solid.

Step C 4-Chloro-2-isopropyl-5-phenylisothiazol-3(2H)-one 1,1-dioxide

DMF (25 mL) and oxalyl chloride (0.2 mL, 2.29 mmol) were added separately to a solution of 4-hydroxy-2-isopropyl-5-phenylisothiazol-3(2H)-one 1,1-dioxide (0.5 g, 1.87 mmol) in DCM (25 mL) at 0° C. The reaction mixture was then heated at 50° C. for 4 h, water was added and the resulting mixture was extracted with EtOAc. The combined organic layers were washed with water, then brine and evaporated. The residue was purified by silica gel column chromatography using a 4:1 mixture of hexane and EtOAc as eluant to give the title compound (0.25 g, 46%) as a solid; $^1$H NMR (200 MHz, CDCl$_3$): δ 8.10-7.94 (m, 2H), 7.61-7.50 (m, 3H), 4.50 (sep, 1H), 1.61 (s, 3H), 1.65 (s, 6H).

4-Hydroxy-5-phenylisothiazol-3(2H)-one 1,1-dioxide

The title compound can be prepared as described in the reference below: J. Org. Chem., 1984, 49(12), 2212-2217.

4-Chloro-5-phenylisothiazol-3(2H)-one 1,1-dioxide

Dry DMF (1.2 ml) was added dropwise to a mixture of oxalyl chloride (4.96 g, 39.1 mmol) and 4-hydroxy-5-phenylisothiazol-3(2H)-one 1,1-dioxide (2.2 g, 9.77 mmol) in DCM. The resulting solution was heated under reflux until it turned orange. The mixture was then cooled to room temperature and filtered affording the title compound (1.18 g, 50%) as white solid. $^1$H NMR (400 MHz, d$_6$-DMSO): δ 7.41-7.54 (m, 3H), 7.77-7.80 (m, 2H), 12.70 (br.s, 1H); $^{13}$C-NMR (100 MHz, d$_6$-DMSO): δ 126.1, 127.1, 128.3, 129.9, 130.6, 144.9, 162.2.

4-Chloro-2-methyl-5-phenylisothiazol-3(2H)-one 1,1-dioxide

A solution of 4-chloro-5-phenylisothiazol-3(2H)-one 1,1-dioxide (2.0 g, 8.21 mmol) and MeI (3.5 g, 24.6 mmol) in DMF (30 ml) was cooled with an ice bath, and anhydrous potassium carbonate (1.13 g, 8.21 mmol) was added. The mixture was then allowed to warm to rt and stirred for 21 h. Water (60 ml) was added and the white precipitate formed, was filtered off and washed with water. Toluene was added to the precipitate and the mixture was evaporated and the residue was dried for three days under vacuum to give the title compound (2.2 g, 102%) containing traces of water and toluene. $^1$H NMR (400 MHz, CDCl$_3$): δ 3.23 (s, 3H), 7.52-7.56 (m, 3H), 7.86-7.88 (m, 2H); $^{13}$C-NMR (100 MHz, CD$_3$CN): δ 24.5, 123.8, 1291, 129.5, 130.7, 133.0, 143.1, 157.6.

tert-Butyl (5-{[4-[(4-morpholin-4-ylphenyl)amino]-1,1-dioxido-3-oxo-5-phenylisothiazol-2(3H)-yl]methyl}pyridin-2-yl)carbamate (4-piperazin-1-ylphenyl)amine (0.42 g, 2.3 mmol) was added to an ice cold solution of 4-chloro-5-phenylisothiazol-3(2H)-one 1,1-dioxide (0.57 g, 2.3 mmol) in DMF (4 ml) and the mixture was stirred for 1 h. tert-Butyl[5-(bromomethyl)pyridin-2-yl]carbamate (0.67 g, 2.3 mmol) and anhydrous potassium carbonate (0.32 g, 2.3 mmol) were added. The reaction mixture was stirred over night, concentrated and the residue was dissolved in DCM. The mixture was washed with water and concentrated and the residue was purified using preparative HPLC to give the title compound (0.22 g, 16%). $^1$H NMR (400 MHz, d$_6$-DMSO): δ 1.42 (s, 9H), 3.10-3.11 (m, 4H), 3.57-3.66 (m, 1H), 3.71-3.74 (m, 4H), 3.78-3.84 (m, 1H), 5.70 (s, 1H), 6.95-6.98 (m, 1H), 7.20-7.25 (m, 1H), 7.38-7.42 (m, 5H), 7.48-7.51 (m, 1H), 7.70-7.73 (m, 2H), 7.78 (s, 1H), 9.51 (s, 1H).

tert-Butyl (5-{[4-{[4-(difluoromethoxy)phenyl]amino}-1,1-dioxido-3-oxo-5-phenylisothiazol-2(3H)-yl]methyl}pyridin-2-yl)carbamate

[4-[Difluoromethoxy)phenyl]amine (0.27 g, 1.7 mmol) was added to an ice cold solution of 4-chloro-5-phenylisothiazol-3(2H)-one 1,1-dioxide (0.41 g, 1.7 mmol) in DMF (4 ml) and the mixture was stirred for 1 h. tert-Butyl[5-(bromomethyl)pyridin-2-yl]carbamate (0.48 g, 1.7 mmol) and anhydrous potassium carbonate (0.23 g, 1.7 mmol) were added. The reaction mixture was stirred over night, concentrated and the residue was dissolved in DCM. The mixture was washed with water and concentrated and the residue was purified using preparative HPLC to give the title compound (0.12 g, 13%). $^1$H NMR (400 MHz, d$_6$-DMSO): δ 1.41 (s, 9H), 3.77 (dd, 2H), 7.22-7.24 (m, 3H), 7.27 (t, 1H), 7.39-7.45 (m, 5H), 7.48 (d, 1H), 7.78 (d, 1H), 7.86 (dd, 2H), 9.57 (s, 1H), 11.18 (s, 1H); Mass Spectrum: M+H$^+$ 573.

4-{[4-(Benzyloxy)phenyl]amino}-2-tert-1-butyl-5-phenylisothiazol-3(2H)-one 1,1-dioxide 2-tert-Butyl-4-chloro-5-phenylisothiazol-3(2H)-one 1,1-dioxide (0.3 g, 1 mmol), 4-benzyloxyaniline hydrochloride (0.307 g, 1.3 mmol) and TEA (0.304 g, 3 mmol) was dissolved in dry DMSO (10 ml). The reaction was heated at 110° C. for 25 min in a microwave reactor. The reaction mixture was diluted with water (200 ml) and extracted with EtOAc (200 ml), the organic phase was dried (MgSO$_4$), filtered and evaporated. The residue was purified by silica gel column chromatography using a 65:35 mixture of heptane:EtOAc as eluant to give the title compound (0.345 g, 75%). $^1$H NMR (500 MHz, CDCl$_3$): δ 7.41-7.30 (m, 5H), 7.20-7.14 (m, 1H), 7.13-7.05 (m, 5H), 6.65-6.55 (m, 4H), 4.93 (s, 2H), 1.78 (s, 9H); $^{13}$C NMR (125 MHz, CDCl$_3$): δ 160.2, 156.3, 136.9, 131.2, 129.6, 129.0, 128.8, 128.2, 128.1, 127.5, 125.1, 123.9

1-(5-Amino-1-benzofuran-2-yl)ethanone

Iron powder (0.680 g, 12.19 mmol) was added in portions to a solution of 1-(5-nitro-1-benzofuran-2-yl)ethanone (0.500 g, 2.44 mmol) and NH$_4$Cl (0.652 g, 12.19 mmol) in EtOH (15 mL) and water (4 mL) and the mixture was refluxed for 1 h. The mixture was filtered through Celite and washed out with DCM. The solvents were evaporated and the residue was dissolved in DCM. The organic layer was washed with water, dried through a phase separator and evaporated. The product was purified by silica gel column chromatography using a EtOAc/hexane/MeOH (49:49:2) as eluant, to give the title compound (0.232 g, 54%) as a yellow solid; $^1$H NMR (500 MHz, CD$_3$OD): δ 7.50 (ds, 1H), 7.33 (d, 1H), 6.95-7.00 (m, 2H), 2.54 (s, 3H); Mass Spectrum: M+H$^+$ 176.

tert-Butyl 5-amino-1-benzofuran-2-carboxylate

The title compound can be prepared as described in J. Med. Chem. 2000 43(14) 2675-84.

tert-Butyl [5-(bromomethyl)pyridin-2-yl]carbamate

The title compound was prepared as described in the reference below: WO0066557, Linschoten, M. et al, AstraZeneca A B, Nov. 9, 2000.

Example 1

2-tert-Butyl-4-[(4-morpholin-4-yl-phenyl)amino]-5-phenylisothiazol-3(2H)-one 1,1-dioxide A solution of 2-tert-butyl-4-chloro-5-phenylisothiazol-3(2H)-one 1,1-dioxide (0.400 g, 1.33 mmol) and 4-morpholinoaniline (0.476 g, 2.67 mmol) in DMF (4 mL) was heated at 140° C. for 15 mins in a microwave reactor. EtOAc was then added, and the resulting mixture was washed with brine and evaporated. The residue was purified by silica gel column chromatography using a 1:1 mixture of petroleum ether and EtOAc as eluant, to give the title compound (0.328 g, 56%) as a solid; $^1$H NMR (500 MHz, CDCl$_3$): δ 7.23-7.18 (m, 1H), 7.15-7.09 (m, 4H), 6.62 (d, 2H), 6.52 (d, 2H), 3.83 (t, 4H), 3.00 (t, 4H), 1.79 (s, 9H); Mass Spectrum: M−H$^+$ 440.

Example 2

2-tert-Butyl-5-pheny 4-[(4-piperidin-1-ylphenyl)amino]isothiazol-3(2H)-one 1,1-dioxide A solution of 2-tert-butyl-4-chloro-5-phenylisothiazol-3(2H)-one 1,1-dioxide (0.150 g, 0.50 mmol) and 4-piperidinoaniline (0.176 g, 1.00 mmol) in DMF (2 mL) was heated at 120° C. for 15 mins in a microwave reactor. EtOAc was then added and the resulting mixture was washed with brine and evaporated. The residue was purified by silica gel column chromatography using a 9:1 mixture of petroleum ether and EtOAc as eluant, to give the title compound (0.110 g, 50%) as a solid; $^1$H NMR (500 MHz, CDCl$_3$): δ 7.22-7.18 (m, 1H), 7.16-7.05 (m, 5H), 6.58 (d, 2H), 6.54 (d, 2H), 3.02 (t, 4H), 1.80 (s, 9H), 1.70-1.62 (m, 4H), 1.58-1.54 (m, 2H); $^{13}$C NMR (125 MHz, CDCl$_3$): δ 160.3, 149.9, 131.3, 129.6, 128.8, 128.1, 127.8, 125.3, 123.5, 116.3, 109.4, 61.9, 51.1, 27.9, 25.7, 24.4; Mass Spectrum: M+H$^+$ 440.

Example 3

2-tert-Butyl-4-[(4-isopropoxyphenyl)amino]-5-phenylisothiazol-3(2H)-one 1,1-dioxide A solution of 2-tert-butyl-4-chloro-5-phenylisothiazol-3(2H)-one 1,1-dioxide (0.150 g, 0.50 mmol) and 4-isopropoxyaniline (0.151 g, 1.00 mmol) in MeCN (2 mL) was heated at 120° C. for 35 mins in a microwave reactor. The mixture was evaporated and the residue was purified by silica gel column chromatography using a 5:1 mixture of petroleum ether and EtOAc as eluant, to give the title compound (0.100 g, 48%) as a solid; $^1$H NMR (500 MHz, CDCl$_3$): δ 7.20-7.14 (m, 1H), 7.12-7.08 (m, 4H), 7.04 (s, 1H), 6.62 (d, 1H), 6.48 (d, 2H), 4.34 (sep, 1H), 1.77 (s, 9H), 1.22 (d, 6H); $^{13}$C NMR (125 MHz, CDCl$_3$): δ 160.1, 155.5, 131.4, 129.7, 129.3, 128.9, 128.1, 125.2, 124.1, 116.1, 109.9, 70.5, 61.9, 27.9, 22.0; Mass Spectrum: M−H$^+$ 414.

Example 4

2-tert-Butyl-4-[(6-morpholin-4-ylpyridin-3-yl)amino]-5-phenylisothiazol-3(2H)-one 1,1-dioxide A solution of 2-tert-butyl-4-chloro-5-phenylisothiazol-3(2H)-one 1,1-dioxide (0.150 g, 0.50 mmol), 6-morpholin-4-ylpyridin-3-amine (0.108 g, 0.60 mmol) and TEA (0.06 mL, 0.60 mmol) in MeCN (2 mL) was heated at 140° C. for 1 h in a microwave reactor. The mixture was evaporated and the residue was purified by silica gel column chromatography using a 3:1 mixture of EtOAc and petroleum ether as eluant, to give the title compound (0.038 g, 17%) as a solid; $^1$H NMR (500 MHz, CDCl$_3$): δ 7.81 (d, 1H), 7.24-7.1.5 (m, 1H), 7.14-7.10 (m, 4H), 6.94 (s, 1H), 6.72 (dd, 1H), 6.12 (d, 1H), 3.75 (t, 4H), 3.33 (t, 4H), 1.77 (s, 9H); $^{13}$C NMR (125 MHz, CDCl$_3$): δ 159.9, 157.5, 142.9, 131.6, 131.9, 130.0, 129.1, 128.3, 124.7, 124.2, 110.2, 105.9, 66.7, 62.1, 46.1, 27.9; Mass Spectrum: M+H$^+$ 443.

Example 5

2-Ethyl-4-[(4-morpholin-4-ylphenyl)amino]-5-phenylisothiazol-3(2H)-one 1,1-dioxide A solution of 4-chloro-2-ethyl-5-phenylisothiazol-3(2H)-one 1,1-dioxide (0.217 g, 0.80 mmol) and 4-morpholinoaniline (0.285 g, 1.60 mmol) in DMF (2.0 mL) was heated at 110° C. for 15 mins in a microwave reactor. The mixture was purified by preparative HPLC (C8 50×250, 0.1M NH$_4$OAc/MeCN, gradient) which gave impure product. Repurification was done by preparative HPLC (C8 50×250, 0.1M NMR OAc/MeCN, 50% MeCN isocratic) to give the title compound (0.096 g, 29%) as a solid; $^1$H NMR (500 MHz, CDCl$_3$): δ 7.22-7.16 (m 1H), 7.12-7.09 (m, 4H), 6.62-6.57 (m 2H), 6.52-6.48 (m, 2H), 3.84 (q, 2H), 3.81-3.78 (m, 4H), 2.99-2.95 (m, 4H), 1.47 (t 3H); $^{13}$C NMR (500 MHz, CDCl$_3$): δ 159.4, 149.2, 131.5, 129.5, 128.9, 128.4, 128.1, 125.1, 123.6, 115.6, 109.8, 66.9, 49.7, 35.6, 14.0; Mass Spectrum: M−H$^+$ 414.

Example 6

4-[(2-Acetyl-1-benzofuran-5-yl)amino]-2-butyl-5-phenylisothiazol-3(2H)-one 1,1-dioxide A mixture of 2-butyl-4-chloro-5-phenylisothiazol-3(2H)-one 1,1-dioxide (300 mg, 0.90 nmol) and 1-(5-amino-1-benzofuran-2-yl)ethanone (387 mg, 2.21 mmol) in dry MeCN (4.5 mL) was heated in a microwave reactor at 130° C. for 1 h, then at 130° C. for 1 h, then at 140° C. for 1 h and finally at 140° C. for 1.5 h. The mixture was purified using preparative HPLC (Kromasil-column C8, 0.1M NH$_4$OAc/MeCN, gradient) to give the title compound (116 mg, 28%); $^1$H NMR (400 MHz, CD$_3$CN): δ 7.86 (bs, 1H), 7.34-7.32 (m, 1H), 7.26-7.22 (m, 1H), 7.03-7.15 (m, 7H), 3.76 (t, 2H), 1.78-1.87 (m, 2H) 1.43-1.54 (m, 2H), 1.05 (t, 3H); Mass Spectrum: M−H$^+$ 437

Example 7

2-Butyl-4-[(hydroxyphenyl)amino]-5-phenylisothiazol-3(2H)-one 1,1-dioxide

A mixture of 2-butyl-4-chloro-5-phenylisothiazol-3(2H)-one 1,1-dioxide (0.110 g, 0.33 mmol), 4-hydroxyaniline hydrochloride (0.144 g, 0.99 mmol) and TEA (0.14 ml, 0.991 mmol) in DMF (0.5 ml) was heated at 140° C. for 25 mins in a microwave reactor. The mixture was purified by preparative HPLC (column Ace C8, 0.1M NH₄OAc/MeCN, gradient) to give the title compound (0.074 g, 57%); ¹H NMR 400 MHz (CDCl₃) 7.26-7.20 (m, 2H), 7.18-7.14 (m, 3H), 7.08 (s, 1H), 6.62 (d, 2H), 6.48 (d, 2H), 3.78 (t, 2H), 1.91-1.84 (m, 2H), 1.53-1.45 (m, 2H), 1.02 (t, 3H); Mass Spectrum: M+H 373.

Example 8

2-Butyl-5-phenyl-4-(1H-1,2,4-triazol-3-ylamino) isothiazol-3(2H)-one 1,1-dioxide A solution of 2-butyl-4-chloro-5-phenylisothiazol-3(2H)-one 1,1-dioxide (0.110 g, 0.33 mmol) and 3-amino-1,2,4-triazole (0.083 g, 0.991 mmol) in DMF (0.5 mL) was heated at 140° C. for 25 mins in a microwave reactor. The residue was purified by preparative HPLC (Column Ace C8 (5u), 0.1M NH₄OAc/MeCN, gradient) to give the title compound (0.0036 g, 2.2%); ¹H-NMR (500 MHz, CD₃CN): δ 7.78 (s, 1H), 7.20-7.40 (m, 5H), 3.74 (t, 2H), 1.84-1.76 (m, 2H), 1.51-1.42 (m, 2H), 0.99 (t, 3H); Mass Spectrum: M+H 348.

Example 9

2-Butyl-4-{[4-(difluoromethoxy)phenyl]amino}-5-phenylisothiazol-3(2H)-one 1,1-dioxide 2-Butyl-4-chloro-5-phenylisothiazol-3(2H)-one 1,1-dioxide (0.63 g, 2.1 mmol) and 4-(difluoromethoxy)-aniline (0.67 g, 4.2 mmol) were mixed in MeCN (4 mL, dry). The mixture was put in the microwave reactor at 160° C. for 1 h, then additional 1 h and then 1 h more. It was evaporated to dryness. The residue was purified by column chromatography (ISOLUTE SI, 50 g/150 mL), eluting with DCM/heptane (50:50, then 75:25), to give the title compound (0.688 g, 78%) as a yellow solid; ¹H-NMR (400 MHz; CDCl₃): δ 0.99 (t, 3H), 1.42-1.52 (m, 2H), 1.82-1.90 (m, 2H), 3.77 (t, 2H), 6.34 (t, 1H), 6.67 (d, 2H), 6.76 (d, 2H), 7.11-7.17 (m, 4H), 7.22-7.26 (m, 1H); Mass Spectrum: M–H⁺ 421.

Example 10

2-Butyl-5-(3-chlorophenyl)-4-[(4-morpholin-4-ylphenyl)amino]isothiazol-3(2H)-one 1,1-dioxide 4-Morpholin-4-ylaniline (53 mg, 0.30 mmol) was added to a solution of 2-butyl-4-chloro-5-(3-chlorophenyl)isothiazol-3(2H)-one 1,1-dioxide (50 mg, 0.15 mmol) in dry DMF (1.0 mL) at rt and under an atmosphere of nitrogen. The reaction mixture was heated in a microwave reactor at 140° C. for 25 mins, whereafter the solvents were removed. Another portion of 4-morpholin-4-ylaniline (160 mg, 0.90 mmol) was added to a solution of 2-butyl-4-chloro-5-(3-chlorophenyl)isothiazol-3(2H)-one 1,1-dioxide (150 mg, 0.45 mmol) in dry DMF (2.0 mL) at rt and under an atmosphere of nitrogen. The reaction mixture was heated in a microwave reactor at 140° C. for 25 mins, whereafter the solvents were removed. The obtained two mixtures were combined and purified using preparative HPLC (column ACE C8, 0.1M NH₄OAc/MeCN, gradient) followed by column chromatography (Horizons Biotage, Heptane:EtOAc, 3:1, isocratic run) to give the title compound (132 mg, 62%) as a yellow solid; ¹H NMR (500 MHz, CDCl₃): δ 7.22 (bs, 1H), 7.13-7.19 (m, 2H), 7.06-7.11 (m, 1H), 6.93-6.96 (m, 1H), 6.65-6.69 (m, 2H), 6.55-6.60 (m, 2H), 3.82-3.86 (m, 4H), 3.75-3.80 (t, 2H), 3.04-3.08 (m, 4H), 1.83-1.91 (m, 2H), 1.44-1.52 (m, 2H), 1.01 (t, 3H); ¹³C NMR (125 MHz, CDCl₃): δ 159.3, 149.8, 134.2, 132.6, 130.3, 129.3, 129.0, 127.9, 127.3, 126.8, 124.3, 115.6, 107.8, 66.9, 49.6, 40.5, 30.4, 20.3, 13.8; Mass Spectrum: M–H 474.

Example 11

4-[(2-Acetyl-1-benzofuran-5-yl)amino]-2-ethyl-5-[4-(trifluoromethyl)phenyl]isothiazol-3(2H)-one 1,1-dioxide A solution of 4-chloro-2-ethyl-5-[4-(trifluoromethyl)phenyl]isothiazol-3(2H)-one 1,1-dioxide (0.160 g, 0.471 mmol), 1-(5-amino-1-benzofuran-2-yl)ethanone (0.165 g, 0.942 mmol) and TEA (0.048 g, 0.471 mmol) in DMF (1 mL) was heated at 140° C. for 25 mins in a microwave reactor.

EtOAc was then added to the reaction mixture, and the resulting mixture was washed with brine and dried and evaporated. The residue was purified by preparative HPLC (Kromasil C8, 0.1M NH₄OAc/MeCN, gradient) to give the title compound (0.078 g, 34%) as a solid; ¹H NMR (500 MHz, CDCl₃): δ 7.40 (bs, 1H), 7.30 (d, 2H), 7.29 (d, 1H), 7.23 (d, 2H), 7.15 (s, 1H), 6.98 (dd, 1H), 6.93 (d, 1H), 3.91 (q, 2H), 2.58 (s, 3H), 1.52 (t, 3H); ¹³C NMR (125 MHz, CDCl₃): δ 13.97, 26.62, 35.97, 109.13, 112.04, 112.88, 117.50, 123.66, 124.74 (t, J=272.2 Hz), 125.02, 127.21, 128.89, 129.86, 131.15 (q, J=32.8 Hz), 132.04, 132.76, 153.25, 154.22, 158.65, 188.49; Mass Spectrum: M–H⁺ 478.

Example 12

2-Butyl-5-(4-chlorophenyl)-4-{[4-(difluoromethoxy)phenyl]amino}isothiazol-3(2H)-one 1,1-dioxide 2-Butyl-4-chloro-5-(4-chlorophenyl)isothiazol-3(2H)-one 1,1-dioxide (0.20 g, 0.60 mmol) and 4-(difluoromethoxy)-aniline (0.190 g, 1.20 mmol) were mixed in MeCN (2.5 mL). The mixture was heated in a microwave reactor at 130° C. for 15 mins, then additional 60 mins and then at 140° C. for 15 mins, then additional 30 mins. The mixture was evaporated and the residue was purified by column chromatography (ISOLUTE SI 20 g/70 mL), eluting with heptane, then DCM:heptane (25:75, then 50:50), to give the title compound (0.122 g, 45%); ¹H NMR (400 MHz, CDCl₃): δ 7.28 (s, 1H), 7.12 (d, 2H), 7.04 (d, 2H), 6.81 (d, 2H), 6.70 (d, 2H), 6.37 (t, 1H), 3.76 (t, 2H), 1.87-1.80 (m, 2H), 1.50-1.40 (m, 2H), 0.97 (t, 3H); ¹³C NMR (100 MHz, CDCl₃): δ 158.9, 148.0, 135.6, 133.1, 131.3, 130.3, 128.4, 123.7, 123.1, 120.1, 115.5 (t), 110.1, 40.3, 30.1, 20.0, 13.4; Mass Spectrum: M–H⁺ 455.

Example 13

4-[(2-Acetyl-1-benzofuran-5-yl)amino]-2-(2-methoxyethyl)-5-phenylisothiazol-3(2H)-one 1,1-dioxide A solution of 4-chloro-2-(2-methoxyethyl)-5-phenylisothiazol-3(2H)-one 1,1-dioxide (0.245 g, 0.81 mmol) and 1-(5-amino-1-benzofuran-2-yl)ethanone (0.285 g, 1.63 mmol) in DMF (4 mL) was heated at 130° C. for 4 h in a microwave reactor. The product was purified by preparative HPLC [0.1M NH₄OAc/MeCN, gradient A:B (8:2 to 3:7)]. The product fractions were evaporated and the residue was extracted with DCM. The organic layer was washed with saturated NaHCO₃, dried through a phase separator and evaporated to give the title compound (0.123 g, 34%) as a solid; ¹H NMR (500 MHz, CD₃CN): δ 7.32 (ds, 1H), 7.24 (d, 1H), 7.02-7.16 (m, 7H), 3.93 (t, 2H), 3.73 (t, 2H), 3.38 (s, 3H), 2.49 (s, 3H); Mass Spectrum: M+H⁺ 441.

Example 14

2-[4-(Difluoromethoxy)benzyl]-4-{[4-(difluoromethoxy)phenyl]amino}-5-phenylisothiazol-3(2H)-one 1,1-dioxide 4-Chloro-2-[4-(difluoromethoxy)benzyl]-5-phenylisothiazol-3(2H)-one 1,1-dioxide (80 mg, 0.2 mmol) and 4-(difluoromethoxy)-aniline (64 mg, 0.4 mmol) were mixed in MeCN (2 mL).

The mixture was heated in a microwave rector at 130° C. for 15 mins, then an additional 15 mins and then at 140° C. for 15 mins. It was then evaporated to dry. Column chromatography (ISOLUTE SI 10 g/70 mL) of the residue, eluting with EtOAc:heptane (10:90, then 20:80), gave a product mixture. It was further purified by re-chromatography (ISOLUTE SI, 5 g/25 mL), eluting with EtOAc:heptane (10:90, then 20:80), to give the title compound (6 mg, 6%); $^1$H NMR (400 MHz, CDCl$_3$): δ 7.55 (d, 2H), 7.26-7.22 (m, 1H), 7.17-7.10 (m, 6H), 6.75 (d, 2H), 6.67 (d, 2H), 6.51 (t, 1H), 6.33 (t, 1H), 4.87 (s, 2H); $^{13}$C NMR (100 MHz, CDCl$_3$): δ 159.0, 151.2, 147.9, 133.1, 131.3, 130.8, 130.6, 129.5, 129.3, 128.2, 124.4, 123.5, 120.0, 119.7, 115.8 (t), 115.5 (t), 111.6, 42.9; Mass Spectrum: M–H$^+$ 521.

Example 15

2-tert-Butyl-4-[(4-methoxyphenyl)amino]-5-phenylisothiazol-3(2H)-one 1,1-dioxide A mixture of 2-tert-butyl-4-chloro-5-phenylisothiazol-3(2H)-one 1,1-dioxide (0.300 g, 1.001 mmol), (4-methoxyphenyl)amine (0.136 g, 1.101 mmol) and TEA (0.140 ml, 1.001 mmol) in MeCN (3 ml) was heated in a microwave reactor at 120° C. for 20 mins, 130° C. for 30 mins, 140° C. for 30 mins and then using an oil bath at 120° C. for 24 h. The mixture was evaporated and the residue was purified by silica gel column chromatography using a 17% EtOAc in petroleum ether 40-60° C. as eluent, to give the title compound (0.152 g, 39%). $^1$H NMR (500 MHz, CDCl$_3$): δ 7.24-7.14 (m, 1H), 7.12-7.08 (m, 1H), 7.07 (bs, 1H), 6.62 (d, 2H), 6.50 (d, 2H), 3.67 (s, 3H), 1.77 (s, 9H); $^{13}$C NMR (125 MHz CDCl$_3$): δ 160.2, 157.2, 131.2, 129.6, 129.4, 128.9, 128.1, 125.1, 123.9, 113.8, 109.9, 61.9, 55.7, 27.9; Mass Spectrum: M+H$^+$ 387.

Example 16

2-tert-Butyl-5-phenyl-4-[(4-pyrrolidin-1-ylphenyl)amino]isothiazol-3(2H)-one 1,1-dioxide A mixture of 2-tert-butyl-4-chloro-5-phenylisothiazol-3(2H)-one 1,1-dioxide (0.150 g, 0.500 mmol), (4-pyrrolidin-1-ylphenyl)amine (0.081 g, 0.500 mmol) and TEA (0.070 ml, 0.500 mmol) in MeCN (2 ml) and DMF (1 ml) was heated in a microwave reactor at 120° C. for 45 mins. TEA (0.070 ml, 0.500 mmol) was added and the mixture was heated at 120° C. for 15 mins. The precipitate from the reaction mixture was isolated by filtration and washed with MeCN. The crude product was dissolved in MeOH and purified by silica gel column chromatography using 15-100% EtOAc in petroleum ether 40-60° C. as eluent, to give the title compound (0.146 g, 69%). $^1$H NMR (500 MHz, CDCl$_3$): δ 7.22-7.02 (m, 5H), 6.55 (d, 2H), 6.14 (d, 2H), 3.15-3.10 (m, 4H), 1.99-1.92 (m, 4H), 1.77 (s, 9H); 13C NMR (125 MHz CDCl$_3$): δ 160.8, 149.9, 131.6, 129.7, 128.5, 127.9, 125.5, 124.7, 123.9, 111.2, 108.8, 61.8, 47.9, 27.9, 25.6; Mass Spectrum: M+H$^+$ 426.

Example 17 tert-Butyl {4-[(2-tert-butyl-1,1-dioxido-3-oxo-5-phenyl-2,3-dihydroisothiazol-4-yl)amino]phenyl}carbamate A mixture of 2-tert-butyl-4-chloro-5-phenylisothiazol-3(2H)-one 1,1-dioxide (0.200 g, 0.667 mmol) and tert-butyl (4-aminophenyl)carbamate (0.278 g, 1.344 mmol) in DMF (2 ml) was heated in a microwave reactor at 120° C. for 30 mins. EtOAc was added, and the mixture was washed with brine and evaporated. The residue was triturated in MeOH, the solvent was decanted and the residue was purified by silica gel column chromatography using 15-65% EtOAc in petroleum ether 40-60° C. as eluent, to give the title compound (0.147 g, 47%) as a solid. $^1$H NMR (500 MHz, d$_6$-DMSO): δ 9.18 (s, 1H), 9.16 (s, 1H), 7.22 (dt, 1H), 7.18 (dt, 2H), 7.08-7.00 (m, 4H), 6.64 (d, 2H), 1.65 (s, 9H), 1.44 (s, 9H); $^{13}$C NMR (d$_6$-DMSO): δ 160.3, 153.0, 136.8, 132.3, 131.9, 129.6, 129.3, 128.6, 125.9, 123.2, 117.9, 109.2, 79.8, 61.4, 28.8, 27.9; Mass Spectrum: M–H$^+$ 470.

Example 18

4-[(4-Isopropoxyphenyl)amino]-2-isopropyl-5-phenylisothiazol-3(2H)-one 1,1-dioxide 4-Chloro-2-isopropyl-5-phenylisothiazol-3(2H)-one 1,1-dioxide (0.2 g, 0.7 mmol), 4-isopropoxyaniline (0.106 g, 0.7 mmol) and TEA (0.071 g, 0.7 mmol) was dissolved in dry MeCN (3 ml). The reaction mixture was heated at 160° C. for 30 min in a microwave reactor. The solvent was evaporated and the residue was purified by silica gel column chromatography using a 70:30 mixture of heptane:EtOAc as eluant to give the title compound (0.166 g, 59%). $^1$H NMR (500 MHz, CDCl$_3$): δ 7.21-7.15 (m, 1H), 7.13-7.09 (m, 4H), 7.06 (brs, 1H), 6.65-6.59 (m, 2H), 6.53-6.48 (m, 2H), 4.48 (hep, 1H), 4.35 (hep, 1H), 1.63 (d, 6H), 1.23 (d, 6H); $^{13}$C NMR (125 MHz, CDCl$_3$): δ 159.0, 155.5, 131.6, 129.5, 128.9, 128.1, 125.0, 124.1, 124.0, 116.0, 109.7, 70.4, 47.8, 21.9, 20.4.

Example 19

2-Isopropyl-5-phenyl-4-[(4-piperidin-1-ylphenyl)amino]isothiazol-3(2H)-one 1,1-dioxide A mixture of 4-chloro-2-isopropyl-5-phenylisothiazol-3(2H)-one 1,1-dioxide (0.150 g, 0.525 mmol), (4-piperidin-1-ylphenyl)amine (0.093 g, 0.525 mmol) and TEA (0.053 g, 0.525 mmol) in MeCN (2 ml) was heated in a microwave at 160° C. for 30 mins. The reaction mixture was evaporated and the residue was purified by silica gel column chromatography using 30% EtOAc in hexane as eluent, to give the title compound (0.169 g, 76%). $^1$H NMR (500 MHz CDCl$_3$): δ 7.24-7.16 (m, 1H), 7.16-7.08 (m, 5H), 6.58 (d, 2H), 6.54 (d, 2H), 4.56-4.44 (m, 1H), 3.03 (t, 4H), 1.70-1.61 (m, 10H), 1.61-52 (m, 3H); $^{13}$C NMR (125 MHz CDCl$_3$): δ 159.2, 150.1, 131.1, 129.6, 128.8, 128.1, 127.6, 125.3, 123.6, 116.3, 109.3, 51.1, 47.9, 25.7, 24.4, 20.5; Mass Spectrum: M+H 426.

Example 20

4-[(4-Azepan-1-ylphenyl)amino]-2-tert-butyl-5-phenylisothiazol-3(2H)-one 1,1-dioxide A mixture of 2-tert-butyl-4-chloro-5-phenylisothiazol-3(2H)-one 1,1-dioxide (0.150 g, 0.500 mmol), (4-azepan-1- ylphenyl)amine (0.095 g, 0.500 mmol) and TEA (0.070 ml, 0.500 mmol) in MeCN (2 ml) was heated in a microwave reactor at 120° C. for 65 mins. TEA (0.070 ml, 0.500 mol) was added and the reaction mixture was heated in a microwave reactor at 120° C. for 15 mins. The reaction mixture was filtered and the residue was purified by silica gel column chromatography using 15-20% EtOAc in petroleum ether 40-60° C. as eluent, to give the title compound (0.121 g, 53%). $^1$H NMR (500 MHz CDCl$_3$): δ 7.16-7.04 (m, 5H), 7.00 (s, 1H), 6.53 (d, 2H), 6.23 (d, 2H), 3.33 (t, 4H), 1.77 (s, 9H), 1.73-1.61 (m, 4H), 1.50-1.45 (m, 4H); $^{13}$C NMR (125 MHz CDCl$_3$): δ 160.4, 146.6, 131.8, 129.8, 128.5, 127.9, 125.4, 124.5, 124.3, 110.7, 108.3, 61.8, 49.7, 27.3, 26.9; Mass Spectrum: M+H$^+$ 454.

Example 21

2-Isopropyl-4-[(4-morpholin-4-ylphenyl)amino]-5-phenylisothiazol-3(2H)-one 1,1-dioxide A mixture of 4-chloro-2-isopropyl-5-phenylisothiazol-3 (2H)-one 1,1-dioxide (0.150 g, 0.525 mmol), (4-morpholin-4-ylphenyl)amine (0.094 g, 0.525 mmol) and TEA (0.070 ml, 0.525 mmol) in MeCN (2 ml) was heated in a microwave reactor at 150° C. for 15 mins and 160° C. for 30 mins. The reaction mixture was evaporated and the residue was purified by silica gel column chromatography using 35% EtOAc in hexane as eluent, to give the title compound (0.157 g, 70%). $^1$H NMR (500 MHz CDCl$_3$): δ 7.24-7.18 (m, 1H), 7.15-7.10 (m, 5H), 6.64 (d, 2H), 6.59 (bs, 2H), 4.54-4.45 (m 1H), 3.85 (bs, 4H), 3.03 (bs, 4H), 1.65 (d, 6H); $^{13}$C NMR (125 MHz CDCl$_3$): δ 159.1, 131.3, 129.5, 128.9, 128.2, 125.2, 123.6, 15.9, 66.8, 50.0, 47.9, 20.5; Mass spectrum: M+H$^+$ 428.

Example 22

2-Butyl-4-[(4-methoxyphenyl)amino]-5-phenylisothiazol-3(2H)-one 1,1-dioxide

2-Butyl-4-chloro-5-phenylisothiazol-3(2H)-one 1,1-dioxide (50 mg, 0.17 mmol) was dissolved in MeCN (1.0 mL, dry) and 4-methoxyophenylamine (41 mg, 0.33 mmol) was added. The reaction mixture was heated in a microwave reactor at 150° C. for 5 mins. The reaction mixture was diluted with MeCN and water (1:1, 2.5 mL) and purified by preparative HPLC using MeCN/O. 1M NH$_4$OAC as eluant and then by column chromatography using Heptane EtOAc (4:1) as eluant to give the title compound (8 mg, 10%). $^1$H NMR (400 MHz, CDCl$_3$): δ 7.25-7.15 (m, 1H), 7.14-7.05 (m, 5H), 6.7-6.6 (d, 2H), 6.55-6.45 (d, 2H), 3.75 (t, 2H), 3.65 (s, 3H), 1.95-1.8 (m, 2H), 1.55-1.4 (m, 2H), 1.0 (t, 3H); $^{13}$C NMR (100 MHz, CDCl$_3$) δ 159.6, 134.2, 129.6, 129.1, 128.2, 124.0, 113.8, 110.0, 55.7, 40.4, 30.5, 20.3, 13.7; Mass Spectrum M–H$^+$: 386.

Example 23

2-Butyl-4-[(4-morpholin-4-ylphenyl)amino]-5-phenylisothiazol-3(2H)-one 1,1-dioxide 2-Butyl-4-chloro-5-phenylisothiazol-3(2H)-one 1,1-dioxide (0.04 g, 0.13 mmol) and 4-morpholinoaniline (0.05 g, 0.27 mmol) in MeCN (1.5 ml) was heated in a microwave reactor at 140° C. for 5 mins, then at 140° C. for 15 mins, then at 140° C. for 15 mins and finally at 140° C. for 20 mins. The mixture was purified by preparative HPLC (Kromasil-column C8, 0.1M NH$_4$OAc/MeCN, gradient) to give the title compound (29 mg, 50%); $^1$H NMR (400 MHz, CD$_3$CN): δ 7.66 (bs, 1H), 7.21-7.27 (m, 1H), 7.07-7.17 (m, 4H), 6.67-6.72 (m, 2H), 6.51-6.56 (m, 2H), 3.70-3.76 (m, 6H), 2.92-2.97 (m, 4H), 1.76-1.85 (m, 2H), 1.41-1.52 (m, 2H), 1.00 (t, 3H); Mass Spectrum: M–H$^+$ 440.

Example 24 tert-Butyl 6-[(2-butyl-1,1-dioxido-3-oxo-5-phenyl-2,3-dihydroisothiazol-4-yl)amino]-3,4-dihydroisoquinoline-2(1H)-carboxylate A mixture of 2-butyl-4-chloro-5-phenylisothiazol-3(2H)-one 1,1-dioxide (1.000 g, 3.336 mmol), tert-butyl 6-amino-3,4-dihydroisoquinoline-2(1H)-carboxylate (0.828 g, 3.336 mmol) and TEA (0.460 ml, 3.33 gmmol) in dry MeCN (5 ml) was heated in a microwave reactor at 120° C. for 35 mins, 140° C. for 20 mins and 160° C. for 45 mins.

The reaction mixture was evaporated and the residue was purified by silica gel column chromatography (Horizons Biotage) using 10-25% EtOAc in petroleum ether 40-60° C. as eluent, to give the title compound (0.760 g, 45%). $^1$H NMR (500 MHz CDCl$_3$); δ 7.26-7.22 (m, 1H), 7.22-7.14 (m, 4H), 6.83 (d, 1H), 6.65 (dd, 1H), 6.30 (d, 1H), 4.42 (s, 2H), 3.79 (t, 2H), 3.45 (t, 2H), 3.45 (t, 2H), 1.92-1.84 (m, 2H), 1.56-1.44 (m, 11H), 1.01 (t, 3H); $^{13}$C NMR (125 MHz CDCl$_3$): δ 159.5, 155.0, 134.1, 130.9, 129.6, 129.4, 128.3, 126.6, 125.4, 122.6, 120.0, 111.1, 80.1, 40.5, 30.5, 28.9, 20.3, 13.8; Mass Spectrum: M+H$^+$ 512.

Example 25

2-Butyl-4-[(3-chloro-4-morpholin-4-ylphenyl)amino]-5-phenylisothiazol-3(2H)-one 1,1-dioxide A solution of 2-butyl-4-chloro-5-phenylisothiazol-3(2H)-one 1,1-dioxide (0.025 g, 0.083 mmol) and 3-chloro-4-morpholinoaniline (0.039 g, 0.183 mmol) in MeCN (1 ml) was heated in a microwave reactor at 130° C. for 90 mins. The product was purified by preparative HPLC (Kromasil C8, 0.1M NH$_4$OAc/MeCN, gradient). The combined product fractions were evaporated and freeze-dried to give the title compound (0.004 mg, 9%). $^1$H NMR (400 MHz, CD$_3$CN): δ 7.74 (bs, 1H), 7.29-7.24 (m, 1H), 7.20-7.15 (m, 2H), 7.12-7.08 (m, 2H), 6.80-6.75 (m, 3H), 3.76-3.71 (m, 6H), 2.85-2.81 (m, 4H), 1.85-1.76 (m, 2H), 1.52-1.42 (m, 2H), 1.00 (t, 3H); Mass Spectrum: M+H$^+$ 476.

Example 26

4-[(2-Acetyl-1,2,3,4-tetrahydroisoquinolin-6-yl)amino]-2-butyl-5-phenylisothiazol-3(2H)-one 1,1-dioxide Acetyl chloride (0.020 ml, 0.243 mmol) was added to a solution of 2-butyl-5-phenyl-4-(1,2,3,4-tetrahydroisoquinolin-6-ylamino)isothiazol-3(2H)-one 1,1-dioxide (example 60) (0.100 g, 0.243 mmol) and TEA (0.040 mmol, 0.267 mmol) in dry THF (2 ml) and the reaction mixture was stirred at rt for 40 mins. EtOAc was added and the mixture was washed with brine and evaporated. The residue was purified by silica gel column chromatography using a 1:5 mixture of EtOAc/petroleum ether 40-60° C. mixture as eluent, to give the title compound (0.071 g, 64%). $^1$H NMR (500 MHz CDCl$_3$); δ 7.30-7.22 (m, 2H), 7.22-7.14 (m, 4H), 6.88, 6.68 (dd, 1H), 6.68 (td, 1H), 6.36, 6.31 (d, 1H), 4.58, 4.47 (s, 2H), 3.79 (t, 2H), 3.63, 3.48 (t, 2H), 2.43, 2.39 (t, 2H), 2.16, 2.15 (s, 3H), 1.94-1.84 (m, 2H), 1.56-1.44 (m, 2H), 1.01 (t, 3H); $^{13}$C NMR (125 MHz CDCl$_3$): δ 169.8, 159.6, 135.8, 134.4, 131.0, 130.8, 129.6, 129.4, 128.3, 127.0, 126.2, 126.0, 122.6, 122.2, 120.4, 120.0, 111.4, 111.2, 47.8, 43.9, 40.5, 39.4, 30.5, 29.3, 26.8, 22.0, 21.8, 20.3, 13.8; Mass Spectrum M+H$^+$ 454.

Example 27

There is no Example 27.

Example 28

2-Butyl-4-(1H-indol-5-ylamino)-5-phenylisothiazol-3(2H)-one 1,1-dioxide

2-Butyl-4-chloro-5-phenylisothiazol-3(2H)-one 1,1-dioxide (110 mg, 0.330 mmol) was dissolved in dry DMF (0.5 mL) under nitrogen atmosphere. 1H-Indol-5-amine (131 mg, 0.991 mmol) was added and the reaction mixture was heated in a microwave reactor at 140° C. for 25 mins. The crude product was purified by preparative HPLC affording the title compound (126 mg, 96.5%). $^1$H NMR (500 MHz, CD$_3$CN): δ 1.01 (t, 3H), 1.44-1.53 (m, 2H), 1.78-1.86 (m, 2H), 3.75 (t, 2H), 6.20-6.22 (m, 1H), 6.68-6.71 (m, 1H), 6.99-7.18 (m, 8H), 7.76 (bs, 1H), 9.18 (bs, 1H).

Example 29

5-[(2-Butyl-1,1-dioxido-3-oxo-5-phenyl-2,3-dihydroisothiazol-4-yl)amino]-N,N-dimethyl-1-benzofuran-2-carboxamide A mixture of 5-[(2-Butyl-1,1-dioxido-3-oxo-5-phenyl-2,3-dihydroisothiazol-4-yl)amino]-1-benzofuran-2-carboxylic acid (example 51) (0.100 g, 0.227 mmol), dimethylamine in THF (2M, 0.321 ml), EDC (0.132 g, 0.681 mmol), HOBt (0.065 g, 0.249 mmol) and TEA (0.090 ml, 0.681 mmol) in DMF (2 ml) was heated at 70° C. for 18 h. EtOAc was added and the mixture was washed with brine, evaporated and the residue was purified by flash chromatography (Horizons Biotage) using 50-65% EtOAc in hexane as eluent to give the title compound (0.054 g, 51%); $^1$H NMR (500 MHz CDCl$_3$); δ 7.18 (dd, 1H), 7.14-7.10 (m, 3H), 7.08-7.02 (m, 2H), 6.99 (s, 1H), 6.91 (d, 1H), 6.84 (dd, 1H), 3.81 (t, 2H), 3.30 (bs, 3H), 3.14 (bs, 3H), 1.94-1.86 (m, 2H), 1.56-1.46 (m, 2H), 1.02 (t, 3H); $^{13}$C NMR (125 MHz CDCl$_3$): δ 161.0, 159.5, 152.1, 151.0, 132.1, 131.4, 129.5, 129.5, 128.3, 127.1, 124.9, 121.6, 115.9, 111.9, 111.4, 111.2, 40.5, 30.5, 20.3, 13.8.; Mass Spectrum M+H$^+$ 468.

Example 30

2-[4-(Difluoromethoxy)benzyl]-4-[(4-morpholin-4-ylphenyl)amino]-5-phenylisothiazol-3(2H)-one 1,1-dioxide 4-Chloro-2-[4-(difluoromethoxy)benzyl]-5-phenylisothiazol-3(2H)-one 1,1-dioxide (40 mg, 0.1 mmol) and 4-morpholinoaniline (36 mg 0.2 mmol) were mixed in MeCN (1 ml). The reaction mixture was heated in a microwave reactor at 150° C. for 15 mins and then evaporated to dryness. The residue was purified by column chromatography (ISOLUTE SI, 5 g/25 ml), eluting with DCM, then MeOH/DCM (1:99) and a product mixture was obtained. It was further purified by re-chromatography (ISOLUTE SI, 5 g/25 ml), eluting with EtOAc/heptane (10:90, then 25:75), to give the title compound (14 mg, 26%) as a yellow solid. $^1$H NMR (400 MHz, CDCl$_3$): δ 2.96-2.99 (m, 4H), 3.78-3.81 (m, 4H), 4.86 (s, 2H), 6.47-6.51 (m, 2H), 6.50 (t, J=74 Hz, 1H), 6.57-6.60 (m, 2H), 7.09-7.13 (m, 7H), 7.17-7.22 (m, 1H), 7.52-7.57 (m, 2H); $^{13}$C NMR (100 MHz, CDCl$_3$): δ 42.8, 49.4, 66.6, 109.7, 115.3, 115.8 (t, J=259 Hz), 119.6, 123.5, 124.7, 127.9, 128.9, 129.3, 130.6, 131.2, 131.5, 149.1, 151.2, 159.3; Mass Spectrum: M−H$^+$ 540.

Example 31

2-Butyl-5-(3-chlorophenyl)-4-{[4-(difluoromethoxy)phenyl]amino}isothiazol-3(2H)-one 1,1-dioxide 2-Butyl-4-chloro-5-(3-chlorophenyl)isothiazol-3(2H)-one 1,1-dioxide (0.250 g, 0.75 mmol) and 4-(difluoromethoxy)aniline (0.238 g, 1.50 mmol) were mixed in MeCN (2 mL) and heated in a microwave reactor at 160° C. for 60 mins. The reaction mixture was evaporated and the residue was purified on a Horizon TM flash system using Heptane and EetOAc as eluant giving the title compound (0.25 g, 72.9%). $^1$H-NMR (500 MHz, CDCl$_3$): δ 7.25-7.1 (m, 4H), 7.0 (s, 1H), 6.9-6.7 (dd, 4H), 6.4 (t, 1H, J=Hz), 3.8 (t, 2H), 1.95-1.8 (m, 2H), 1.55-1.45 (m, 2H), 1.05 (t, 3H); $^{13}$C-NMR (125 MHz, CDCl$_3$): δ179.6, 159.0, 134.4, 133.3, 132.0, 129.9, 129.6, 129.6, 127.3, 124.3, 120.4, 115.9, 40.6, 30.4, 23.6, 20.3, 13.7; Mass Spectrum: M−H$^+$ 456.

Example 32

2-Butyl-5-phenyl-4-{[4-(trifluoromethoxy)phenyl]amino}isothiazol-3(2H)-one 1,1-dioxide 2-Butyl-4-chloro-5-phenylisothiazol-3(2H)-one 1,1-dioxide (110 mg, 0.330 mmol) was dissolved in dry DMF (0.5 mL) under nitrogen atmosphere. [4-(Trifluoromethoxy)phenyl]amine (175 mg, 0.991 mmol) was added and the reaction mixture was heated in a microwave reactor for 25 mins at 140° C. The crude product was purified by preparative HPLC affording the title compound (84 mg, 56.6%). $^1$H NMR (500 MHz, CD$_3$CN): δ 1.00 (t, 3H), 1.43-1.52 (m, 2H), 1.78-1.85 (m, 2H), 3.75 (t, 2H), 6.85-6.93 (m, 4H), 7.11-7.20 (m, 4H), 7.24-7.29 (m, 1H), 7.82 (bs, 1H).

Example 33

2-Butyl-4-{[4-(hydroxymethyl)phenyl]amino}-5-phenylisothiazol-3(2H)-one 1,1-dioxide 2-Butyl-4-chloro-5-phenylisothiazol-3(2H)-one 1,1-dioxide (110 mg, 0.331 mmol) was dissolved in dry DMF (0.5 mL) under nitrogen atmosphere. (4-Aminophenyl)methanol (122 mg, 0.991 mmol) was added and the reaction mixture was heated in a microwave reactor for 25 mins at 140° C. The crude product was purified by preparative HPLC affording the title compound (6 mg, 4.7%). $^1$H NMR (500 MHz, CD$_3$CN): δ 1.00 (t, 3H), 1.43-1.52 (m, 2H), 1.78-1.85 (m, 2H), 3.03 (t, 1H), 3.75 (t, 2H), 4.40 (d, 2H), 6.77 (d, 2H), 6.97 (d, 2H), 7.13-7.19 (m, 4H), 7.24-7.28 (m, 1H), 7.76 (bs, 1H).

Example 34

4-{[4-(Benzyloxy)phenyl]amino}-2-butyl-5-phenylisothiazol-3(2H)-one 1,1-dioxide

A mixture of 2-butyl-4-chloro-5-phenylisothiazol-3(2H)-one 1,1-dioxide (0.600 g, 2.001 mmol), [4-(benzyloxy)phenyl]amine (1.415 g, 6.004 mmol) and TEA (0.840 ml, 6.004 mmol) in DMF (5 ml) was heated in a microwave reactor at 140° C. for 25 mins. EtOAc was added to the mixture, and it was washed with brine, evaporated and the residue was purified by flash chromatography using a 5:1 EtOAc/petroleum ether 40-60° C. mixture as eluent to give the title compound (0.721 g, 78%). $^1$H NMR (500 MHz CDCl$_3$); δ 7.42-7.33 (m, 4H), 7.22-7.17 (m, 1H), 7.15-7.09 (m, 5H), 6.65 (d, 2H), 6.61 (d, 2H), 4.96 (s, 2H), 3.79 (t, 2H), 1.92-1.84 (m, 2H), 1.54-1.44 (m, 2H), 1.01 (t, 3H); Mass Spectrum M+H$^+$ 463.

Example 35

4-{[4-(4-Benzylpiperazin-1-yl)phenyl]amino}-2-butyl-5-phenylisothiazol-3(2H)-one 1,1-dioxide A mixture of 2-butyl-4-chloro-5-phenylisothiazol-3(2H)-one 1,1-dioxide (0.400 g, 1.334 mmol), [4-(4-benzylpiperazin-1-yl)phenyl]amine (0.357 g, 1.334 mmol) and TEA (0.190 ml, 1.334 mmol) in MeCN (5 ml) was heated in a microwave reactor at 120° C. for 35 mins, 160° C. for 20 mins and 180° C. for 20 mins. The reaction mixture was evaporated and the residue was purified by flash chromatography (Horizons Biotage) using 35-65% EtOAc in petroleum ether 40-60° C. as eluent to give the title compound (0.721 g, 78%). $^1$H NMR (500 MHz CDCl$_3$); δ 7.40-7.32 (m, 3H), 7.30-7.24 (m, 2H), 7.22-7.18 (m, 1H), 7.16-7.08 (m, 4H), 6.60 (d, 2H), 6.52 (d, 2H), 3.78 (t, 2H), 3.57 (d, 2H), 3.05 (t, 4H), 2.57 (t, 4H), 1.92-1.84 (m, 2), 1.54-1.46 (m, 2H), 1.01 (t, 3H); $^{13}$C NMR (125 MHz CDCl$_3$).: 159.7, 149.4, 138.1, 131.5, 129.5, 129.4, 128.9, 128.5, 128.1, 127.9, 127.4, 125.1, 123.6, 118.8, 109.4, 63.3, 53.1, 49.5, 40.4, 30.5, 20.3, 13.8; Mass Spectrum: M+H$^+$ 531.

Example 36

2-[4-(Difluoromethoxy)benzyl]-4-[(4-methoxyphenyl)amino]-5-phenylisothiazol-3(2H)-one 1,1-dioxide The title compound was prepared from 4-chloro-2-[4-(difluoromethoxy)benzyl]-5-phenylisothiazol-3(2H)-one 1,1-dioxide and 4-methoxyaniline in a similar manner as described for e.g. Examples 14 and 30. H NMR (400 MHz, CDCl$_3$): δ 3.67 (s, 3H), 4.86 (s, 2H), 6.48-6.52 (m, 2H), 6.50 (t, J=74 Hz, 1H), 6.60-6.64 (m, 2H), 7.09-7.14 (m, 7H), 7.52-7.56 (m, 2H); $^{13}$C NMR (100 MHz, CDCl$_3$): δ 42.8, 55.5, 109.9, 113.6, 115.8 (t, J=259 Hz), 119.6, 123.8, 124.6, 128.0, 128.7, 129.0, 129.3, 130.6, 131.3, 131.4, 151.2, 157.3, 159.3; Mass Spectrum: M–H$^+$ 485.

Example 37

4-(1-Benzofuran-5-ylamino)-2-butyl-5-phenylisothiazol-3(2H)-one 1,1-dioxide

A solution of 2-butyl-4-chloro-5-phenylisothiazol-3(2H)-one 1,1-dioxide (0.047 g, 0.141 mmol) and 1-benzofuran-5-amine (0.046 g, 0.345 mmol) in MeCN (1.5 ml) was heated in a microwave reactor at 130° C. for 60 mins and at 140° C. for 45 mins. The reaction mixture was evaporated and the residue was purified by column chromatography using EtOAc:heptane (1:3) as eluant. Crystallisation from hexane and EtOH gave the title compound (0.015 g, 27%). $^1$H NMR (400 MHz, CD$_3$CN): 7.80 (bs, 1H), 7.65 (d, 1H), 7.17-7.09 (m, 4H), 7.07-7.02 (m, 3H), 6.85 (dd, 1H), 6.60-6.58 (m, 1H), 3.76 (t, 2H), 1.87-1.78 (m, 2H), 1.54-1.43 (m, 2H), 1.01 (t, 3H); Mass Spectrum: M+H$^+$ 397.

Example 38

2-Butyl-4-[(5-methyl-1-phenyl-1H-pyrazol-3-yl)amino]-5-phenylisothiazol-3(2H)-one 1,1-dioxide 2-Butyl-4-chloro-5-phenylisothiazol-3(2H)-one 1,1-dioxide (110 mg, 0.330 mmol) was dissolved in dry DMF (0.5 mL) under nitrogen atmosphere. 5-Methyl-1-phenyl-1H-pyrazol-3-amine (172 mg, 0.991 mmol) was added and the reaction mixture was heated in a microwave reactor for 25 mins at 140° C. The crude product was purified by preparative HPLC affording the title compound (89 mg, 58.6%). $^1$H NMR (500 MHz, CD$_3$CN): δ 0.99 (t, 3H), 1.42-1.51 (m, 2H), 1.76-1.84 (m, 2H), 2.14 (s, 3H), 3.73 (t, 2H), 5.87 (s, 1H), 6.87-6.90 (m, 2H), 7.27-7.38 (m, 8H), 7.74 (bs, 1H).

Example 39

2-Butyl-4-[(6-methoxypyridin-3-yl)amino]-5-phenylisothiazol-3(2H)-one 1,1-dioxide 2-Butyl-4-chloro-5-phenylisothiazol-3(2H)-one 1,1-dioxide (58 mg, 0.20 mmol) and 6-methoxypyridin-3-amine (49 mg, 0.40 mmol) was dissolved in MeCN (11.0 mL) and the reaction mixture was heated in a microwave reactor at 150° C. for 5 mins. The reaction mixture was diluted with MeCN and water and purified by preparative HPLC using MeCN/0.1M NH$_4$OAc as eluant giving the title compound (3.4 mg, 4.3%). $^1$H NMR (500 MHz, CDCl$_3$): δ 7.75 (d, 1H), 7.25-7.1 (m, 4H), 7.0 (bs, 1H), 6.85 (dd, 1H), 6.3 (d, 1H), 3.78 (t, 2H), 1.9-1.8 (m, 2H), 1.5-1.4 (m, 2H), 1.0 (t, 3H); Mass Spectrum: M–H$^+$ 386.

Example 40

2-Butyl-5-phenyl-4-[(2-thioxo-2,3-dihydro-1,3-benzothiazol-6-yl)amino]isothiazol-3(2H)-one 1,1-dioxide 2-Butyl-4-chloro-5-phenylisothiazol-3(2H)-one 1,1-dioxide (110 mg, 0.330 mmol) was dissolved in dry DMF (0.5 mL) under nitrogen atmosphere. 6-Amino-1,3-benzothiazole-2-thiol (181 mg, 0.991 mmol) was added and the reaction mixture was heated in a microwave reactor for 25 mins at 140° C. The crude product was purified by preparative HPLC affording the title compound (7 mg, 4.5%). $^1$H NMR (500 MHz, CD$_3$CN): δ 1.00 (t, 3H), 1.43-1.52 (m, 2H), 1.78-1.85 (m, 2H), 3.75 (t, 2H), 6.86-7.00 (m, 3H), 7.11-7.28 (m, 5H), 7.84 (bs, 1H).

Example 41

2-Methyl-4-[(4-morpholin-4-ylphenyl)amino]-5-phenylisothiazol-3(2H)-one 1,1-dioxide 4-Chloro-2-methyl-5-phenylisothiazol-3(2H)-one 1,1-dioxide (70 mg, 0.27 mmol) and 4-morpholinoaniline (97 mg, 0.54 mmol) in MeCN (2 ml) was heated in a microwave reactor at 140° C. for 15 mins, then at 140° C. for 15 mins. The mixture was purified by preparative HPLC (Kromasil-column C8, 0.1M NH$_4$OAc/MeCN, gradient) to give the title compound (46 mg, 42%); $^1$H NMR (400 MHz, CDCl$_3$): δ

7.10-7.23 (m, 6H), 6.58-6.63 (m, 2H), 6.49-6.55 (m, 2H), 3.77-3.83 (m, 4H), 3.27 (s, 3H), 2.96-3.01 (m, 4H); Mass Spectrum: M+H$^+$ 400.

Example 42

4-[(4-Methoxyphenyl)amino]-2-methyl-5-phenyl-isothiazol-3(2H)-one 1,1-dioxide

The title compound was prepared from 4-chloro-2-methyl-5-phenylisothiazol-3(2H)-one 1,1-dioxide and 4-methoxyaniline in a similar manner as described for e.g. Examples 9 and 13. $^1$H NMR (400 MHz, CD$_3$CN): δ 7.67 (bs, 1H), 7.27-7.22 (m, 1H), 7.18-7.10 (m, 4H), 6.78-6.73 (m, 2H), 6.57-6.52 (m, 2H), 3.65 (s, 3H), 3.20 (s, 3H); Mass Spectrum: M+H$^+$ 345.

Example 43

4-[(4-Cyclohexylphenyl)amino]-2-(2-methoxyethyl)-5-phenylisothiazol-3(2H)-one 1,1-dioxide The title compound was prepared from 4-chloro-2-(2-methoxyethyl)-5-phenylisothiazol-3(2H)-one 1,1-dioxide and 4-cyclohexylaniline in a similar manner as described for e.g. Examples 9 and 13. $^1$H NMR (400 MHz, CD$_3$CN): δ 1.19-1.44 (m, 5H), 1.64-1.84 (m, 5H), 2.31-2.40 (m, 1H), 3.38 (s, 3H), 3.72 (t, 2H), 3.90 (t, 2H), 6.67-6.72 (m, 2H), 6.80-6.85 (m, 2H), 7.05-7.14 (m, 4H), 7.19-7.24 (m, 1H), 7.75 (bs, 1H); Mass Spectrum: M+H$^+$ 441.

Example 44

4-[(2-Acetyl-1-benzofuran-5-yl)amino]-2-methyl-5-phenylisothiazol-3(2H)-one 1,1-dioxide The title compound was prepared from 4-chloro-2-methyl-5-phenylisothiazol-3(2H)-one 1,1-dioxide and 1-(5-amino-1-benzofuran-2-yl)ethanone in a similar manner as described for e.g. Examples 9 and 13. $^1$H NMR (400 MHz, CD$_3$CN): δ 7.89 (bs, 1H), 7.38-7.37 (m, 1H), 7.25 (d, 1H), 7.16-7.10 (m, 4H), 7.09-7.03 (m, 3H), 3.22 (s, 3H), 2.50 (s, 3H); Mass Spectrum: M+H$^+$ 397.

Example 45

2-(2-Methoxyethyl)-5-phenyl-4-(5,6,7,8-tetrahydronaphthalen-1-ylamino)isothiazol-3(2H)-one 1,1-dioxide The title compound was prepared from 4-chloro-2-(2-methoxyethyl)-5-phenylisothiazol-3(2H)-one 1,1-dioxide and 5,6,7,8-tetrahydronaphthalen-1-amine in a similar manner as described for e.g. Examples 9 and 13. $^1$H NMR (400 MHz, CD$_3$CN): δ 7.37 (bs, 1H), 7.20-7.15 (m, 1H), 7.11-7.01 (m, 4H), 6.75 (d, 1H), 6.70 (t, 1H), 6.63-6.60 (m, 1H), 3.90 (t, 2H), 3.72 (t, 2H), 3.38 (s, 3H), 2.60-2.54 (m, 4H), 1.76-1.69 (m, 2H), 1.66-1.59 (m, 2H); Mass Spectrum: M+H$^+$ 413.

Example 46

4-(1H-Indol-5-ylamino)-2-(2-methoxyethyl)-5-phenylisothiazol-3(2H)-one 1,1-dioxide The title compound was prepared from 4-chloro-2-(2-methoxyethyl)-5-phenylisothiazol-3(2H)-one 1,1-dioxide and 1H-indol-5-amine in a similar manner as described for e.g. Examples 9 and 13. $^1$H NMR (400 MHz, CD$_3$CN): δ 7.78 (bs, 1H), 7.18 (t, 1H), 7.14-7.10 (m, 2H), 7.09-7.05 (m, 2H), 7.03-6.98 (m, 3H), 6.69 (dd, 1H), 6.23-6.20 (m, 1H), 3.92 (t, 2H), 3.74 (t, 2H), 3.39 (s, 3H); Mass Spectrum: M+H$^+$ 398.

Example 47

4-[(4-Fluorophenyl)amino]-2-methyl-5-phenyl-isothiazol-3(2H)-one 1,1-dioxide

The title compound was prepared from 4-chloro-2-methyl-5-phenylisothiazol-3(2H)-one 1,1-dioxide and 4-fluoroaniline in a similar manner as described for e.g. Examples 9 and 13. $^1$H NMR (400 MHz, CDCl$_3$): δ 3.27 (s, 3H), 6.66-6.71 (m, 4H), 7.12-7.26 (m, 5H); $^{13}$C NMR (100 MHz, CDCl$_3$): δ 24.2, 111.1, 115.1, 115.3, 123.8, 123.9, 124.5, 128.2, 129.0, 129.2, 129.3, 131.1, 131.2, 131.8, 131.9, 158.6, 159.0, 161.1; $^{13}$C NMR (100 MHz, CDCl$_3$): δ 24.2, 111.1, 123.8, 123.9, 124.5, 128.2, 129.2, 129.3, 131.2, 131.8, 131.9, 158.6, 159.0, 161.1; Mass Spectrum: M−H$^+$ 331.

Example 48

2-[(6-Aminopyridin-3-yl)methyl]-4-[(4-morpholin-4-ylphenyl)amino]-5-phenylisothiazol-3(2H)-one 1,1-dioxide The title compound was prepared from tert-butyl (5-{[4-[(4-morpholin-4-ylphenyl)amino]-1,1-dioxido-3-oxo-5-phenylisothiazol-2(3H)-yl]methyl}pyridin-2-yl)carbamate and 4-morpholino-4-ylaniline in a similar manner as described for e.g. Examples 9 and 13. $^1$H NMR (400 MHz, DMSO): δ 3.10-3.13 (m, 4H), 3.52-3.69 (m, 2H), 3.71-3.73 (m, 4H), 6.14 (d, 1H), 6.88-6.91 (m, 1H), 6.98-7.00 (m, 2H), 7.39-7.43 (m, 5H), 7.46-7.47 (m, 1H), 7.70-7.37 (m, 2H); Mass Spectrum: M−H$^+$ 490.

Example 49

N-({4-[(2-Butyl-1,1-dioxido-3-oxo-5-phenyl-2,3-dihydroisothiazol-4-yl)amino]phenyl}sulfonyl)acetamide The title compound was prepared from 2-butyl-4-chloro-5-phenylisothiazol-3(2H)-one 1,1-dioxide and N-[(4-aminophenyl)sulfonyl]acetamide in a similar manner as described for e.g. Examples 6-9, 22-25, 28 and 32-35. $^1$H NMR (500 MHz, CD$_3$CN): δ 1.00 (t, 3H), 1.43-1.52 (m, 2H), 1.78-1.85 (m, 2H), 1.94 (s, 3H), 3.76 (t, 2H), 6.88-6.92 (m, 2H), 7.16-7.24 (m, 4H), 7.29-7.34 (m, 1H), 7.54-7.57 (m, 2H), 8.03 (bs, 1H), 9.26 (bs, 1H).

Example 50

Ethyl 5-[(2-butyl-1,1-dioxido-3-oxo-5-phenyl-2,3-dihydroisothiazol-4-yl)amino]-3-methyl-1-benzothiophene-2-carboxylate The title compound was prepared from 2-butyl-4-chloro-5-phenylisothiazol-3(2H)-one 1,1-dioxide and ethyl 5-amino-3-methyl-1-benzothiophene-2-carboxylate in a similar manner as described for e.g. Examples 6-9, 22-25, 28 and 32-35. $^1$H NMR (400 MHz, d-THF): δ 8.85 (bs, 1H), 7.61 (d, 1H), 7.19 (dd, 1H), 7.17-7.13 (m, 2H), 7.09-7.01 (m, 3H), 6.97-6.95 (m, 1H), 4.35-4.28 (m, 2H), 3.76 (t, 2H), 2.34 (s, 3H), 1.89-1.80 (m, 2H), 1.54-1.44 (m, 2H), 1.35 (t, 3H), 1.01 (t, 3H); Mass Spectrum: M−H$^+$ 498.

Example 51

5-[(2-Butyl-1,1-dioxido-3-oxo-5-phenyl-2,3-dihydroisothiazol-4-yl)amino]-1-benzofuran-2-carboxylic acid A mixture of 2-butyl-4-chloro-5-phenylisothiazol-3(2H)-one 1,1-dioxide (1.000 g, 3.336 mmol), tert-butyl 5-amino-1-benzofuran-2-carboxylate (0.778 g, 3.336 mmol) and TEA (0.340 ml, 2.471 mmol) in MeCN (5 ml) was heated in a microwave reactor at 160° C. for 1.5 h. The reaction mixture was evaporated and the residue was purified by flash chromatography using 5:1 DCM/EtOAc (+1% AcOH) as eluent to give the title compound (0.425 g, 29%). $^1$H NMR (500 MHz CD$_3$OD); δ 13.54 (bs, 1H), 9.63 (s, 1H), 7.34 (s, 1H), 7.29 (d, 1H), 7.14-6.97 (m, 6H), 3.71 (t, 2H), 1.75 (qnt, 2H), 1.42 (sex, 2H), 0.95 (t, 2H); Mass Spectrum: M–H$^+$ 439

Example 52 tert-Butyl 5-[(2-butyl-1,1-dioxido-3-oxo-5-phenyl-2, 3-dihydroisothiazol-4-yl)amino]-1-benzofuran-2-carboxylate A mixture of 2-butyl-4-chloro-5-phenylisothiazol-3(2H)-one 1,1-dioxide (1.000 g, 3.336 mmol), tert-butyl 5-amino-1-benzofuran-2-carboxylate (0.778 g, 3.336 mmol) and TEA (0.340 ml, 2.471 mmol) in MeCN (5 ml) was heated in a microwave reactor at 160° C. for 1.5 h.

The reaction mixture was evaporated and the residue was purified by flash chromatography using 12-100% EtOAc in petroleum ether 40-60° C. as eluent to give the title compound (0.171 g, 10%). $^1$H NMR (500 MHz CDCl$_3$); δ 7.32-7.26 (m, 1H), 7.26-7.18 (m, 1H), 7.16-7.10 (m, 3H), 7.10-7.04 (m, 2H), 6.94 (d, 1H), 6.86 (dd, 1H), 3.81 (t, 2H), 1.94-1.86 (m, 2H), 1.63 (s, 9H), 1.58-1.44 (m, 2H), 1.02 (t, 3H); $^{13}$C NMR (125 MHz CDCl$_3$): 159.8, 159.0, 153.0, 148.2, 132.2, 129.5, 129.4, 128.3, 127.2, 124.9, 122.5, 116.3, 112.6, 112.3, 111.2, 83.2, 40.5, 30.5, 28.4, 20.3, 13.8; Mass Spectrum: M–H$^+$ 495.

Example 53

2-(2-Methoxyethyl)-4-[(3-morpholin-4-yl-1H-1,2,4-triazol-5-yl)amino]-5-phenylisothiazol-3(2H)-one 1,1-dioxide The title compound was prepared from 4-chloro-2-(2-methoxyethyl)-5-phenylisothiazol-3(2H)-one 1,1-dioxide and 3-morpholin-4-yl-1H-1,2,4-triazol-5-amine in a similar manner as described for Example 13. $^1$H NMR (400 MHz, CD$_3$CN): δ 7.49-7.61 (m, 5H), 5.71 (bs, 2H), 3.94 (t, 2H), 3.71 (t, 2H), 3.58-3.62 (m, 4H), 3.37 (s, 3H), 3.10-3.14 (m, 4H); Mass Spectrum: M+H$^+$

Example 54

Ethyl 5-{[2-(2-methoxyethyl)-1,1-dioxido-3-oxo-5-phenyl-2,3-dihydroisothiazol-4-yl]amino}-3-methyl-1-benzothiophene-2-carboxylate The title compound was prepared from 4-chloro-2-(2-methoxyethyl)-5-phenylisothiazol-3(2H)-one 1,1-dioxide and ethyl 5-amino-3-methyl-1-benzothiophene-2-carboxylate in a similar manner as described for Examples 9 and 13. $^1$H NMR (400 MHz, THF-d$_8$): δ 1.35 (t, 3H), 2.34 (s, 3H), 3.38 (s, 3H), 3.72 (t, 2H), 3.92 (t, 2H), 4.29-4.34 (m, 2H), 6.95-6.97 (m, 1H), 7.01-7.10 (m, 3H), 7.14-7.21 (m, 3H), 7.61 (d, 1H), 8.89 (bs, 1H); Mass Spectrum: M+H$^+$ 501.

Example 55

4-[(5-cyclohexyl-2-methoxyphenyl)amino]-2-(2-methoxyethyl)-5-phenylisothiazol-3(2H)-one 1,1-dioxide The title compound was prepared from 4-chloro-2-(2-methoxyethyl)-5-phenylisothiazol-3(2H)-one 1,1-dioxide and 5-cyclohexyl-2-methoxyaniline in a similar manner as described for Examples 9 and 13. $^1$H NMR (400 MHz, CD$_3$CN): δ 0.92-1.05 (m, 2H), 1.08-1.33 (m, 3H), 1.41-1.49 (m, 2H), 1.62-1.76 (m, 3H), 2.05-2.15 (m, 1H), 3.38 (s, 3H), 3.70-3.75 (m, 5H), 3.91 (t, 2H), 6.41 (d, 1H), 6.70 (d, 1H), 6.79-6.83 (m, 1H), 7.12-7.22 (m, 4H), 7.24-7.30 (m, 1H), 7.55 (bs, 1H); Mass Spectrum: M+H$^+$ 471.

Example 56

4-[(4-Hydroxyphenyl)amino]-2-(2-methoxyethyl)-5-phenylisothiazol-3(2H)-one 1,1-dioxide The title compound was prepared from 4-chloro-2-(2-methoxyethyl)-5-phenylisothiazol-3(2H)-one 1,1-dioxide and 4-aminophenol in a similar manner as described for Examples 9 and 13. $^1$H NMR (400 MHz, CD$_3$CN): δ 3.37 (s, 3H), 3.72 (t, 2H), 3.90 (t, 2H), 6.40-6.45 (m, 2H), 6.65-6.71 (m, 2H), 6.82 (bs, 1H), 7.10-7.20 (m, 4H), 7.23-7.29 (m, 1H), 7.63 (bs, 1H); Mass Spectrum: M–H$^+$ 373.

Example 57

4-(1H-Benzimidazol-2-ylamino)-2-butyl-5-phenylisothiazol-3(2H)-one 1,1-dioxide

The title compound was prepared from 2-butyl-4-chloro-5-phenylisothiazol-3(2H)-one 1,1-dioxide and 2-amino-1H-benzimidazole in a similar manner as described for e.g. Examples 6-9, 22-25, 28 and 32-35. $^1$H NMR (500 MHz, CD$_3$CN): δ 1.00 (t, 3H), 1.43-1.53 (m, 2H), 1.76-1.85 (m, 2H), 3.71 (t, 2H), 7.12-7.19 (m, 4H), 7.34-7.68 (m, 5H), 8.03-8.06 (m, 2H).

Example 58

2-[(6-Aminopyridin-3-yl)methyl]-4-{[4-(difluoromethoxy)phenyl]amino}-5-phenylisothiazol-3(2H)-one 1,1-dioxide The title compound was prepared from tert-butyl (5-{[4-{[4-(difluoromethoxy)phenyl]amino}-1,1-dioxido-3-oxo-5-phenylisothiazol-2(3H)-yl]methyl}pyridin-2-yl)carbamate and 4-(difluoromethoxy)aniline in a similar manner as described for e.g. Example 5. $^1$H NMR (400 MHz, DMSO): δ 3.57-3.71 (m, 2H), 5.77 (s, 2H), 6.15 (d, 1H), 6.91 (d, 1H), 7.23-7.28 (m, 2H), 7.38-7.48 (m, 6H), 7.86 (d, 1H); Mass Spectrum: M+H$^+$ 473.

Example 59

2-Methyl-4-[(6-morpholin-4-ylpyridin-3-yl)amino]-5-phenylisothiazol-3(2H)-one 1,1-dioxide The title compound was prepared from 4-chloro-2-methyl-5-phenylisothiazol-3(2H)-one 1,1-dioxide and 6-morpholin- 4-ylpyridin-3-amine in a similar manner as described for Examples 9 and 13. $^1$H NMR (400 MHz, CD$_3$CN): δ 3.20 (s, 3H), 3.26-3.30 (m, 4H), 3.65-3.70 (m, 4H), 6.31 (d, 1H), 6.94-6.99 (m, 1H), 7.11-7.22 (m, 4H), 7.25-7.30 (m, 1H), 7.58 (bs, 1H), 7.71 (d, 1H); Mass Spectrum: M−H$^+$ 399.

Example 60

2-Butyl-5-phenyl-4-(1,2,3,4-tetrahydroisoquinolin-6-ylamino)isothiazol-3(2H)-one 1,1-dioxide A mixture of tert-butyl 6-[(2-butyl-1,1-dioxido-3-oxo-5-phenyl-2,3-dihydroisothiazol-4-yl)amino]-3,4-dihydroisoquinoline-2(1H)-carboxylate (example 24) (0.585 g, 1.144 mmol) in DCM (10 ml) and TFA (2 ml) was stirred at rt for 2.5 h. The reaction mixture was basified by addition of saturated aqueous NaHCO$_3$. The organic phase was washed with saturated aqueous NaHCO$_3$ and brine. The mixture was evaporated and the residue was purified by flash chromatography using 0-20% MeOH in DCM as eluent to give the title compound (0.315 g, 67%). $^1$H NMR (500 MHz DMSO-d$_6$); δ 9.44 (bs, 1H), 7.26 (td, 1H), 7.19 (td, 2H), 7.05 (d, 2H), 6.76-6.68 (m, 3H), 6.29 (s, 1H), 3.78 (s, 2H), 3.69 (t, 2H), 2.86 (t, 2H), 2.27 (t, 3H), 1.78-1.68 (m, 2H), 1.46-1.36 (m, 2H), 0.93 (t, 3H); $^{13}$C NMR (125 MHz CDCl3): 159.5, 134.4, 134.3, 130.7, 129.6, 129.5, 128.3, 126.6, 125.4, 122.9, 119.9, 111.2, 46.9, 43.1, 40.5, 30.5, 28.1, 20.3, 13.8: Mass Spectrum: M+H$^+$ 412.

Example 61

5-[(2-Butyl-1,1-dioxido-3-oxo-5-phenyl-2,3-dihydroisothiazol-4-yl)amino]-1H-isoindole-1,3(2H)-dione The title compound was prepared from 2-butyl-4-chloro-5-phenylisothiazol-3(2H)-one 1,1-dioxide and 5-amino-1H-isoindole-1,3(2H)-dione in a similar manner as described for e.g. Examples 6-9, 22-25, 28 and 32-35. $^1$H NMR (500 MHz, CD$_3$CN): δ 1.00 (t, 3H), 1.44-1.54 (m, 2H), 1.78-1.86 (m, 2H), 3.77 (t, 2H), 7.06-7.31 (m, 6H), 7.36-7.52 (m, 2H).

Example 62

2-Butyl-4-[(2,5-diethoxy-4-morpholin-4-ylphenyl)amino]-5-phenylisothiazol-3(2H)-one 1,1-dioxide The title compound was prepared from 2-butyl-4-chloro-5-phenylisothiazol-3(2H)-one 1,1-dioxide and 2,5-diethoxy-4-morpholin-4-ylaniline in a similar manner as described for e.g. Examples 6-9, 22-25, 28 and 32-35. $^1$H NMR (400 MHz, CD$_3$CN): δ 7.46 (bs, 1H), 7.27-7.22 (m, 1H), 7.18-7.09 (m, 4H), 6.25 (d, 2H), 3.86-3.80 (m, 2H), 3.76-3.70 (m, 6H), 3.53-3.47 (m, 2H), 2.91-2.87 (m, 4H), 1.85-1.77 (m, 2H), 1.52-1.42 (m, 2H), 1.36 (t, 3H), 1.22 (t, 3H), 0.99 (t, 3H); Mass Spectrum: M+H$^+$ 530.

Example 63

2-(2-Methoxyethyl)-4-[(4-morpholin-4-ylphenyl)amino]-5-phenylisothiazol-3(2H)-one 1,1-dioxide The title compound was prepared from 4-chloro-2-(2-methoxyethyl)-5-phenylisothiazol-3(2H)-one 1,1-dioxide and 4-morpholin-4-ylaniline in a similar manner as described for Examples 9 and 13. $^1$H NMR (400 MHz, CD$_3$CN): δ 2.92-2.97 (m, 4H), 3.38 (s, 3H), 3.70-3.75 (m, 6H), 3.90 (t, 2H), 6.51-6.56 (m, 2H), 6.68-6.72 (m, 2H), 7.08-7.16 (m, 4H), 7.22-7.27 (m, 1H), 7.67 (bs, 1H); Mass Spectrum: M+H$^+$ 444.

Example 64

4-{[4-(Difluoromethoxy)phenyl]amino}-2-(2-methoxyethyl)-5-phenylisothiazol-3(2H)-one 1,1-dioxide The title compound was prepared from 4-chloro-2-(2-methoxyethyl)-5-phenylisothiazol-3(2H)-one 1,1-dioxide and 4-(difluoromethoxy)aniline in a similar manner as described for Examples 9 and 13. $^1$H NMR (400 MHz, CD$_3$CN): δ 3.38 (s, 3H), 3.72 (t, 2H), 3.91 (t, 2H), 6.57 (t, 1H), 6.74-6.79 (m, 2H), 6.81-6.86 (m, 2H), 7.10-7.20 (m, 4H), 7.25-7.30 (m, 1H), 7.80 (bs, 1H); Mass Spectrum: M+H$^+$ 425.

Example 65

2-Ethyl-4-[(4-morpholin-4-ylphenyl)amino]-5-[4-(trifluoromethyl)phenyl]isothiazol-3(2H)-one 1,1-dioxide The title compound was prepared from 4-chloro-2-ethyl-5-[4-(trifluoromethyl)phenyl]isothiazol-3(2H)-one 1,1-dioxide and 4-morpholin-4-ylaniline in a similar manner as described for Example 11. $^1$H NMR (500 MHz, CDCl$_3$): δ 1.51 (t, 3H), 2.98-3.01 (m, 4H), 3.81-3.83 (m, 4H), 3.88 (q, 2H), 6.52 (d, 2H), 6.64 (d, 2H), 7.22 (d, 2H), 7.36 (d, 2H).

Example 66

6-[(2-Butyl-1,1-dioxido-3-oxo-5-phenyl-2,3-dihydroisothiazol-4-yl)amino]-N-methyl-3,4-dihydroisoquinoline-2(1H)-carboxamide Methylisocyante (0.014 g, 0.243 mmol) was added to a mixture of 2-butyl-5-phenyl-4-(1,2,3,4-tetrahydroisoquinolin-6-ylamino)isothiazol-3(2H)-one 1,1-dioxide (example 60) (0.100 g, 0.243 mmol) and TEA (0.040 ml, 0.292 mmol) in THF (2 ml). EtOAc was added, and the mixture was washed with brine, evaporated and the residue was purified by flash chromatography (Horizons Biotage) using 80-95% EtOAc in petroleum ether 40-60° C. as eluent to give the title compound (0.088 g, 77%). $^1$H NMR (500 MHz CDCl$_3$); δ 7.28-7.20 (m, 1H), 7.20-7.14 (m, 4H), 6.85 (d, 1H), 6.66 (dd, 1H), 6.33 (s, 1H), 4.39 (s, 3H), 3.80 (t, 2H), 3.41 (t, 3H), 2.86 (d, 3H), 2.41 (t, 2H), 1.92-1.84 (m, 2H), 1.56-1.44 (m, 2H), 1.02 (t, 2H); $^{13}$C NMR (125 MHz CDCl$_3$): 159.5, 158.3, 135.5, 134.4, 130.8, 130.4, 129.6, 129.4, 128.3, 126.6, 125.4, 122.3, 120.1, 111.2, 45.3, 41.2, 40.5, 30.5, 28.9, 27.9, 20.3, 13.8; Mass Spectrum: M+H$^+$ 469.

Example 67

4-{[4-(Difluoromethoxy)phenyl]amino}-2-methyl-5-phenylisothiazol-3(2H)-one 1,1-dioxide The title compound was prepared from 4-chloro-2-methyl-5-phenylisothiazol-3(2H)-one 1,1-dioxide and 4-(difluoromethoxy)aniline in a similar manner as described for Examples 9 and 13. $^1$H NMR (400 MHz, CDCl$_3$): δ 3.28 (s, 3H), 6.15-6.52 (m, 1H), 6.66-6.77 (m, 4H), 7.11-7.27 (m, 5H); Mass Spectrum: M−H$^+$ 379.

Example 68

There is no Example 68.

Example 69

2-tert-Butyl-4-[(4-hydroxyphenyl)amino]-5-phenyl-isothiazol-3(2H)-one 1,1-dioxide 4-{[4-(Benzyloxy)phenyl]amino}-2-tert-butyl-5-phenyl-isothiazol-3(2H)-one 1,1-dioxide (0.330 g, 0.71 mmol) was dissolved in dry DCM (40 ml). Boron trifluoride diethyl etherate (1.01 g, 7.13 mmol) and dimethyl sulfide (0.443 g, 7.13 mmol) were added and the reaction mixture was stirred at rt for 41 h. The solvent was evaporated and the residue was dissolved in EtOAc (150 ml) The mixture was washed with water (200 ml), dried (MgSO$_4$), filtered and evaporated. The residue was purified by silica gel column chromatography using a heptane and EtOAc (70:30) as eluant to give the title compound (0.111 g, 42%). $^1$H NMR (500 MHz, CD$_3$OD): δ 7.21-7.16 (m, 1H), 7.13-7.05 (m 4H), 6.63-6.59 (m, 2H), 6.40-6.36 (m, 2H), 1.74 (s, 9H); $^{13}$C NMR (125 MHz, CD$_3$OD): δ 161.2, 155.9, 133.9, 130.7, 130.2, 129.5, 128.8, 126.8, 125.5, 115.7, 62.3, 27.9; Mass Spectrum: M+H$^+$ 373.

Biological Activity

Co-Activator Recruitment Assay

The Ligand Binding Domain (LBD) of human LXRalpha (amino acid 205-447) and LXRbeta (amino acid 216-461) was produced by recombinant techniques in E. coli. A fragment of the human Steroid Receptor Co-Activator-1 (SRC-1) was produced as a synthetic peptide. An anti-6×His-antibody coupled with Europium (Eu$^{3+}$) was used to recognize the His-tag on the LXR-LBD and Allophycocyanin (APC) coupled to streptavidin was used to recognize the biotinylated SRC-1. Agonist binding to LXRalpha or LXRbeta enhances the affinity of LXR towards SRC-1 and thereby brings Eu$^{3+}$ and APC in close proximity. Eu$^{3+}$ is excited at 337 nm and emitts light at 620 nm. This emission, when in close proximity, excites APC to emit light at 665 nm.

Compounds (10 mM) in DMSO were diluted (⅓) in DMSO in 10 concentrations. This dilution plates were further diluted in buffer {20 mM [Tris(hydroxymethyl)aminomethane] pH 7.5, 0.125% CHAPS {3-[(3-Cholamidopropyl)dimethylammonio]-1-propanesulfonate}, 2 mM DTT (Dithiothreitol) and 0.05% BSA (Bovine Serum Albumin)} in order to reduce DMSO concentration, 0.5 µl to 13.5 µl. To this, 6 µl assay mix was added, giving an maximal assay concentration of 83 µM, and the plates (384-well V-groove plates) were incubated at room temperature for 60 to 80 min.

The assay mix has the following final concentrations; LXRalpha mix: 0.06 µg/mL Eu-labelled anti-6×His Ab, 1.15 g/mL Streptavidin APC, 30 nM SRC-1 peptide and 0.9 µg/mL LXRalpha in buffer and LXRbeta mix; 0.06 µg/mL Eu-labelled anti-6×His Ab, 1.15 µg/1 mL Streptavidin APC, 90 nM SRC-1 peptide and 0.2 µg/mL LXRbeta in buffer. Time-resolved fluorescence readings were done in a Wallac Victor reader at 665 nm followed by reading at 615 nm. The LXR ligand, 22-R Hydroxycholesterol or an internal compound at 50 µM was used as the 100% control.

Transactivation Assay

Expression vectors were prepared by inserting the ligand binding domain cDNA (complementary DNA) of human LXRalpha (amino acid 205-447) and LXRbeta (amino acid 216-461) in frame with, 3' to the yeast GAL4 transcription factor DNA binding domain and the nuclear localization signal from the T-antigen of Polyoma Virus in the eucaryotic expression vector pSG5 (Stratagene). The resulting expression vectors pSGGAL-LXRalpha and pSGGAL-LXRbeta were used in cotransfection experiments together with the pGL3 luciferase reporter plasmid containing a minimal SV40 promoter (Promega) and five copies of the UAS GAL4 recognition site. 2.5 µg pSGGAL-LXRalpha or beta were mixed with 251 g pGL3 5×UAS and 22.5 µg pBluscript (Stratagene) in 0.95 mL ice cold PBS containing approx. 4-9 milj. U2/OS osteosarcoma cells. After a five minute incubation on ice the cell/DNA mixture was electroporated in 0.4 cm cuvettes at 960 µF, 230 V using a BioRad electroporator and diluted to 0.32 milj cells/mL in complete DMEM [Dulbecco's Modified Eagle Medium w/o phenol red, (Gibco 11880-028) including 10% FBS (Foetal Bovine Serum), 1% PEST (Penicillin Streptomycin), 20 mM Hepes, 2 mM L-Glutamine and 0.36% Glucose Gibco 31966-021] medium. Cells from at least two electroporations were pooled in order to avoid variations between different electroportations. 25 µl diluted, electroporated cells, were seeded into 384-well plates (0.8×10$^4$ cells/well) and the cells were allowed to adhere for 2 h at 37° C., 5% CO$_2$ in a cell culture incubator. Compounds (10 mM) in DMSO were diluted (1/3) in DMSO in 10 concentrations. This dilution plates were further diluted in complete DMEM w/o phenol red (2.5 l1 to 97.5 µl) in order to reduce DMSO concentration. 7 µl of this was added to the electroporated cells in 384-well plates and incubation was continued for 48 h in a cell culture incubator, after which cells were lysed by adding 32 µl/well LucLite luciferase substrate. Luciferase activity was measured as Luminescence in the Wallac Victor reader after 15 min. incubation at room temperature. The LXR ligand, Tularik T0901317, or an internal standard, at 1 µM was used as the 100% control.

In Vivo Assay

Separation of the desired antiatherogenic and the undesired lipogenic effects of LXR ligands was tested in normal C57 BL6 mice where the test agents are administered for three days (4 doses) in different or fixed oral doses. Gavage was performed once daily about noon, except the last dose that was given at 0700 hours, 3 hours before anaesthesia. 30 Mice were used in each screen and these were divided into five groups with six animals in each. One group was control group and the remaining 4 groups were treated with test agents in fixed or different doses. The test agents were given by gavage once daily for three days in four doses totally.

Blood samples were then obtained under anaesthesia for determination of plasma levels of TG. The liver was removed for determination of liver weight and TG content. 20-50 mg tissue, liver or intestine (first 2-3 cm distal the stomach) was snap-frozen in liquid nitrogen at necropsy for later analysis of any up regulation of LXR target genes, primarily ABCA1, ABCG1, SREBP1c and FAS. The tissues are kept in a –80° C. freezer until analysis.

Stainless steel beads (Cat. No. 69989, QIAGEN) were added to collection micro tubes, one bead per tube, (Cat. No. 19560, QIAGEN), while the tubes were kept on dry ice. Tissues were transferred to the collection micro tubes after which 750 µl QIAzol (Cat. No. 79306, QIAGEN) was added and then the tubes were placed in a Mixer Mill and homogenized for 2×5 minutes at 25 Hz. After homogenization the 96-well plate was centrifuged at 6000×g for one minute at 4° C. in a Sigma 4K-15C centrifuge. 150 µl chloroform was added to all samples, which were shaken vigorously for 15 seconds and incubated at room temperature for 2-3 minutes and centrifuged again at 6000×g for 15 minutes. 2001 of the upper aqueous phase was transferred to Square-well tubes (Cat. No. 19573, QIAGEN) and one volume of 70% ethanol was added and mixed by pipetting up and down. After a 10 minute incubation on ice 2501 samples was loaded onto the wells of a 96-well culture cluster plate (Cat. No. 3595, Corning Incorporated) RNA was purified using an ABI Prism 6700 or ABI Prism 6100 according to the manufacturers recommendations. RNA was eluted in 150 μl with a concentration of 50-200 ng/μl and 10 μl of this was analyzed by agarose gel electrophoresis (non denaturating 1% TBE gel) to verify RNA quality. cDNA synthesis was performed using the High-Capacity Archive Kit (Cat. No 4322171, Applied Biosystems) according to the manufacturers recommendations, by random primers, in a total reaction volume of 50 μl/sample.

Gene expression mRNA levels were determined by real-time PCR (7500 Real-time PCR system, Applied Biosystems). Taqman universal PCR master mix (Cat. No. 4305719, Applied Biosystems) was used in a 25 μl reaction containing 400 nM of each target primer, 100 nM of each of the control primers (36B4), 200 nM of the target probe, 100 nM of the control probe (36B4) and 2.5-10 ng of sample cDNA. The threshold cycles (Ct) for the endogenous control gene 36B4 and target genes were determined and relative mRNA levels were calculated using the comparative Ct method and expressed as fold induction.

The following primer and probes were used: ABCA1 Forward; 5'-AAGGGTTTCTTTGCTCAGATTGTC-3' (SEQ ID NO:1), ABCA1 Reverse; 5'-TGCCAAAGGGTGGCACA-3' (SEQ ID NO:2), ABCA1 Probe; 5'-FAM-CCAGCT-GTCTTTGTTTGCATTGCCC-TAMRA-3' (SEQ ID NO:3), ABCG1 Forward; 5'-CCATGAATGCCAGCAGCTACT-3' (SEQ ID NO:4), ABCG1 Reverse; 5'-CACTGACACGCA-CACGGACT-3' (SEQ ID NO:5) ABCG1 Probe, 5'-FAM-TGCCGCAATGACGGAGCCC-TAMRA-3' (SEQ ID NO:6) FAS Forward; 5'-GGCATCATTGGGCACTCCTT 3 (SEQ ID NO: 7), FAS Reverse; 5'-GCTGCAAGCACAGC-CTCTCT-3' (SEQ ID NO:8) FAS Probe; 5'-FAM-CCATCT-GCATAGCCACAGGCAACCTC-TAMRA-3' (SEQ ID NO:9), SREBP1c Forward; 5'-GGAGCCATGGATTGCA-CATT-3' (SEQ ID NO:10), SREBP1c Reverse; 5'-CCT-GTCTCACCCCCAGCATA-3' (SEQ ID NO:11), SREBP 1 c Probe; 5'-FAM-CAGCTCATCAACAACCAAGACAGT-GACTTCC-TAMRA-3' (SEQ ID NO:12), 36B4 Forward; 5'-GAGGAATCAGATGAGGATATGGGA-3' (SEQ ID NO:13), 36B4 Reverse; 5'-AAGCAGGCTGACTTGGT-TGC-3' (SEQ ID NO:14), 36B4 Probe; 5'-VIC-TCG-GTCTCTCGACTAATCCCGCCAA-TAMRA-3' (SEQ ID NO: 15) From dose-response relationships, selectivity values (relative potencies) were determined to discriminate between the primary intestinal up regulation of LXR target genes and the unwanted plasma and hepatic TG elevations, respectively.

The compounds of formula I have an $EC_{50}$ of less than 50 μmol/l for LXRα and/or β in coactivator recruitment assays and/or reporter gene assays. For example, the compounds of Example 13 and Example 14 have $EC_{50}$'s for LXRα of 0.27 μmol/l and 0.075 μmol/l in the coactivator recruitment assays, respectively, and the compounds of Example 4 and Example 9 have $EC_{50}$'s for LXR α of 0.15 μmol/l and 0.32 μmol/l in the reporter gene assay, respectively.

In addition the compounds of the present invention exhibit favourable pharmacological effects in vivo.

The compounds of the present invention also have a promising toxicological profile

---

The invention claimed is:

1. A compound of general formula (I)

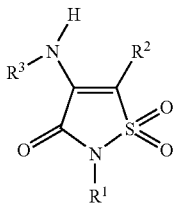

formula (I)

or a pharmaceutically acceptable salt thereof, wherein:

R$^1$ represents:

X which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$ or NR$^a$C(O)NR$^a$R$^a$;

cycloalkyl or heterocyclyl each optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

phenyl or heteroaryl each optionally substituted by one or more of the following independently selected from: halogen, OH, CN, NO$_2$, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

cycloalkylY or heterocyclylY wherein cycloalkyl or heterocyclyl each optionally is substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

phenylY or heteroarylY wherein phenyl or heteroaryl each optionally is substituted by one or more of the following independently selected from: halogen, OH, CN, NO$_2$, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O) OR$^a$, OC(O)R$^b$, SO$_2$NR$^a$R$^a$, NR$^a$SO$_2$R$^b$, NR$^a$C(O) OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

R$^2$ represents:

phenyl which is optionally substituted by one or more of the following independently selected from: halogen, OH, CN, NO$_2$, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O) OR$^a$, OC(O)R$^b$, SO$_2$NR$^a$R$^a$, NR$^a$SO$_2$R$^b$, NR$^a$C(O) OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$;

R$^3$ represents:

aryl or Het$^1$ wherein aryl or Het$^1$ each optionally is substituted by one or more of the following independently selected from: halogen, OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, Q, Het$^2$, R, Het$^3$, QZ, Het$^2$Z, RZ, Het$^3$Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O) OR$^a$, OC(O)R$^b$, NR$^a$SO$_2$R$^b$, SO$_2$NR$^a$R$^a$, NR$^a$C(O) OR$^b$, OC(O)NR$^a$R$^a$ or NR$^a$C(O)NR$^a$R$^a$;

Het$^4$ or T wherein Het$^4$ or T each optionally is substituted on the aromatic ring by one or more of the following independently selected from: halogen, OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, Q, Het$^2$, R, Het$^3$, QZ, Het$^2$Z, RZ, Het$^3$Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$, and wherein Het$^4$ or T each optionally is substituted on the non-aromatic ring by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, thioxo, Q, Het$^2$, R, Het$^3$, QZ, Het$^2$Z, RZ, Het$^3$Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O) R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O) NR$^a$R$^a$ or NR$^a$C(O)NR$^a$R$^a$;

and further wherein:
- X represents a straight or branched, saturated or unsaturated alkyl group having 1 to 6 carbon atoms wherein said alkyl group may optionally be interrupted by one of the following: O, S, $SiR^bR^b$, S(O), $SO_2$, C(O), $NR^a$, OC(O), C(O)O, $NR^aC(O)$, $C(O)NR^a$, $SO_2NR^a$ or $NR^aSO_2$;
- Y binds to nitrogen in 2-position in the isothiazol-3(2H)-one 1,1-dioxide, and represents a straight or branched, saturated or unsaturated alkylene group having 1 to 3 carbon atoms wherein said alkylene group may optionally be interrupted or ended by one of the following: O, S, $SiR^bR^b$, S(O), $SO_2$, C(O), OC(O), C(O)O, $NR^cC(O)$, $C(O)NR^c$, $NR^c$ and/or Y is optionally substituted by one or more of the following independently selected from: OH, F, CN, $NR^aR^a$, $C_1$-$C_4$alkyl, $OR^b$, $SR^b$, $SiR^bR^bR^b$, $S(O)R^b$ or $SO_2R^b$;
- Z binds to aryl, $Het^1$, $Het^4$ or T and one of the following: Q, $Het^2$, R or $Het^3$, and represents a straight or branched, saturated or unsaturated alkylene group having 1 to 6 carbon atoms wherein said alkylene group may optionally be interrupted or ended by one of the following: O, S, $SiR^bR^b$, S(O), $SO_2$, C(O), OC(O), C(O)O, $NR^aC(O)$, $C(O)NR^a$, $NR^a$, $SO_2NR^a$, $NR^aSO_2$, or is one of the following: O, S, $SiR^bR^b$, S(O), $SO_2$, C(O), OC(O), C(O)O, $NR^aC(O)$, $C(O)NR^a$, $NR^a$, $SO_2NR^a$, $NR^aSO_2$ and/or Z is optionally substituted by one or more of the following independently selected from: OH, F, CN, $NR^cR^c$, $C(O)R^c$, $OR^b$, $SR^c$, $SiR^bR^bR^b$, $S(O)R^c$, $SO_2R^c$, phenyl, phenyl$C_1$-$C_3$alkyl, or $C_1$-$C_4$alkyl which is optionally substituted by one or more of the following independently selected from: F, OH, $NR^aR^a$, $SR^b$, $SiR^bR^bR^b$, $S(O)R^b$, $SO_2R^b$, $OR^b$;
- Q represents a saturated or unsaturated non-aromatic monocyclic ring composed of 3, 4, 5, 6, 7 or 8 carbon atoms, which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$;
- R represents a phenyl group which is optionally substituted by one or more of the following independently selected from: halogen, OH, CN, $NO_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$;
- aryl represents a phenyl group which binds to nitrogen in 4-position on the isothiazol-3(2H)-one 1,1-dioxide;
- T binds to nitrogen in 4-position on the isothiazol-3(2H)-one 1,1-dioxide, and represents an aromatic or partly aromatic bicyclic ring composed of 8, 9 or 10 carbon atoms, and where it is the aromatic part of the bicarbocyclic ring that binds to nitrogen in 4-position on the isothiazol-3(2H)-one 1,1-dioxide;
- $Het^1$ binds to nitrogen in 4-position on the isothiazol-3 (2H)-one 1,1-dioxide, and represents an aromatic 5 or 6 membered monocyclic ring in which one or more of the atoms in the ring is an element other than carbon independently selected from one or more of for example nitrogen, oxygen and sulfur;
- $Het^2$ represents a saturated or unsaturated non-aromatic 3, 4, 5, 6, 7, 8, 9 or 10 membered monocyclic ring in which one or more of the atoms in the ring is an element other than carbon independently selected from one or more of for example nitrogen, oxygen or sulfur, and wherein the ring optionally is substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$;
- $Het^3$ represents an aromatic 5 or 6 membered monocyclic ring in which one or more of the atoms in the ring is an element other than carbon independently selected from one or more of for example nitrogen, oxygen and sulfur, and which is substituted by one or more of the following independently selected from: halogen, OH, CN, $NO_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$;
- $Het^4$ binds to nitrogen in 4-position on the isothiazol-3 (2H)-one 1,1-dioxide, and represents an aromatic or partly aromatic 8, 9 or 10 membered bicyclic ring system in which one or more of the atoms in the ring optionally is an element other than carbon independently selected from one or more of for example nitrogen, oxygen and sulfur, and where it is the aromatic part of the bicyclic ring that binds to nitrogen in 4-position on the isothiazol-3(2H)-one 1,1-dioxide;
- $R^a$ independently represents H or a straight or branched, saturated or unsaturated $C_1$-$C_4$alkyl chain optionally substituted by one or more F;
- $R^b$ independently represents a straight or branched, saturated or unsaturated $C_1$-$C_4$alkyl chain optionally substituted by one or more F; and
- $R^c$ independently represents H or a straight or branched, saturated or unsaturated $C_1$-$C_3$alkyl chain optionally substituted by one or more F.

2. A compound according to claim 1 or a pharmaceutically acceptable salt thereof,
wherein:
- $R^1$ represents:
  - X which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$ or $C(O)R^b$;

cycloalkyl or heterocyclyl each optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$ or $C(O)R^b$;

phenyl or heteroaryl each optionally substituted by one or more of the following independently selected from: halogen, OH, CN, $NO_2$, $NR^aR^a$, $OR^b$, $SR^b$, $SiR^bR^bR^b$, $S(O)R^b$, $SO_2R^b$, $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$ or $C(O)R^b$;

cycloalkylY or heterocyclylY wherein cycloalkyl or heterocyclyl each optionally is substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$ or $C(O)R^b$;

phenylY or heteroarylY wherein phenyl or heteroaryl each optionally is substituted by one or more of the following independently selected from: halogen, OH, CN, $NO_2$, $NR^aR^a$, $OR^b$, $SR^b$, $SiR^bR^bR^b$, $S(O)R^b$, $SO_2R^b$, $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$ or $C(O)R^b$;

$R^2$ represents:
phenyl which is optionally substituted by one or more of the following independently selected from: halogen, OH, CN, $NO_2$, $NR^aR^a$, $OR^b$, $SR^b$, $SiR^bR^bR^b$, $S(O)R^b$, $SO_2R^b$, $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$ or $C(O)R^b$.

3. A compound according to claim 2 or a pharmaceutically acceptable salt thereof, wherein $R^1$ represents X which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$ or $NR^aC(O)NR^aR^a$.

4. A compound according to claim 3 or a pharmaceutically acceptable salt thereof, wherein $R^1$ represents X which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$ or $C(O)R^b$.

5. A compound according to claim 1 or a pharmaceutically acceptable salt thereof, wherein $R^3$ represents aryl or $Het^1$ wherein aryl or $Het^1$ each is substituted by one of the following: Q, $Het^2$, R or $Het^3$ and wherein aryl or $Het^1$ each is optionally substituted by one or more of the following independently selected from: halogen, OH, CN, $NO_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

6. A compound according to claim 1 or a pharmaceutically acceptable salt thereof, wherein $R^3$ represents aryl or $Het^1$ wherein aryl or $Het^1$ each optionally is substituted by one or more of the following independently selected from: halogen, OH, CN, $NO_2$, $NR^aR^a$, $OR^b$, $SR^b$, $SiR^bR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, QZ, $Het^2Z$, RZ, $Het^3Z$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

7. A compound according to claim 1 or a pharmaceutically acceptable salt thereof, wherein $R^3$ represents $Het^4$ or T wherein $Het^4$ or T each optionally is substituted on the aromatic ring by one or more of the following independently selected from: halogen, OH, CN, $NO_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, Q, $Het^2$, R, $Het^3$, QZ, $Het^2Z$, RZ, $Het^3Z$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$, and wherein $Het^4$ or T each optionally is substituted on the non-aromatic ring by one or more of the following independently selected from: F, OH, CN, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, thioxo, Q, $Het^2$, R, $Het^3$, QZ, $Het^2Z$, RZ, $Het^3Z$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

8. A compound according to claim 2 or a pharmaceutically acceptable salt thereof, wherein $R^3$ represents aryl or $Het^1$ wherein aryl or $Het^1$ each is substituted by one of the following: Q, $Het^2$, R or $Het^3$ and wherein aryl or $Het^1$ each is optionally substituted by one or more of the following independently selected from: halogen, OH, CN, $NO_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

9. A compound according to claim 2 or a pharmaceutically acceptable salt thereof, wherein $R^3$ represents aryl or $Het^1$ wherein aryl or Het¹ each optionally is substituted by one or more of the following independently selected from: halogen, OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, QZ, Het²Z, RZ, Het³Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

10. A compound according to claim 2 or a pharmaceutically acceptable salt thereof, wherein R³ represents Het⁴ or T wherein Het⁴ or T each optionally is substituted on the aromatic ring by one or more of the following independently selected from: halogen, OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, Q, Het², R, Het³, QZ, Het²Z, RZ, Het³Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$, and wherein Het⁴ or T each optionally is substituted on the non-aromatic ring by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, thioxo, Q, Het², R, Het³, QZ, Het²Z, RZ, Het³Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

11. A compound according to claim 3 or a pharmaceutically acceptable salt thereof, wherein R³ represents aryl or Het¹ wherein aryl or Het¹ each is substituted by one of the following: Q, Het², R or Het³ and wherein aryl or Het¹ each is optionally substituted by one or more of the following independently selected from: halogen, OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

12. A compound according to claim 3 or a pharmaceutically acceptable salt thereof, wherein R³ represents aryl or Het¹ wherein aryl or Het¹ each optionally is substituted by one or more of the following independently selected from: halogen, OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, QZ, Het²Z, RZ, Het³Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

13. A compound according to claim 3 or a pharmaceutically acceptable salt thereof, wherein R³ represents Het⁴ or T wherein Het⁴ or T each optionally is substituted on the aromatic ring by one or more of the following independently selected from: halogen, OH, CN, NO$_2$, NR$^a$R$^a$, OR$^{b1}$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, Q, Het², R, Het³, QZ, Het²Z, RZ, Het³Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$, and wherein Het⁴ or T each optionally is substituted on the non-aromatic ring by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, thioxo, Q, Het², R, Het³, QZ, Het²Z, RZ, Het³Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

14. A compound according to claim 4 or a pharmaceutically acceptable salt thereof, wherein R³ represents aryl or Het¹ wherein aryl or Het¹ each is substituted by one of the following: Q, Het², R or Het³ and wherein aryl or Het¹ each is optionally substituted by one or more of the following independently selected from: halogen, OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

15. A compound according to claim 4 or a pharmaceutically acceptable salt thereof, wherein R³ represents aryl or Het¹ wherein aryl or Het¹ each optionally is substituted by one or more of the following independently selected from: halogen, OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, QZ, Het²Z, RZ, Het³Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

16. A compound according to claim 4 or a pharmaceutically acceptable salt thereof, wherein R³ represents Het⁴ or T wherein Het⁴ or T each optionally is substituted on the aromatic ring by one or more of the following independently selected from: halogen, OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, Q, Het², R, Het³, QZ, Het²Z, RZ, Het³Z, or C₁-C₄alkyl which is optionally substituted by one or more of the following independently selected from: F, OH, CN, NR$^a$R$^a$, OR$^b$, SR$^b$, SiR$^b$R$^b$R$^b$, S(O)R$^b$, SO₂R$^b$, C(O)R$^b$, C(O)NR$^a$R$^a$, NR$^a$C(O)R$^b$, C(O)OR$^a$, OC(O)R$^b$, NR$^a$SO₂R$^b$, SO₂NR$^a$R$^a$, NR$^a$C(O)OR$^b$, OC(O)NR$^a$R$^a$ or NR$^a$C(O)NR$^a$R$^a$, and wherein Het⁴ or T each optionally is substituted on the non-aromatic ring by one or more of the following independently selected from: F, OH, CN, NR$^a$R$^a$, OR$^b$, SR$^b$, SiR$^b$R$^b$R$^b$, S(O)R$^b$, SO₂R$^b$, C(O)R$^b$, phenylC₁alkyl, C(O)NR$^a$R$^a$, NR$^a$C(O)R$^b$, C(O)OR$^a$, OC(O)R$^b$, SO₂NR$^a$R$^a$, NR$^a$SO₂R$^b$, NR$^a$C(O)OR$^b$, OC(O)NR$^a$R$^a$, NR$^a$C(O)NR$^a$R$^a$, thioxo, Q, Het², R, Het³, QZ, Het²Z, RZ, Het³Z, or C₁-C₄alkyl which is optionally substituted by one or more of the following independently selected from: F, OH, CN, NR$^a$R$^a$, OR$^b$, SR$^b$, SiR$^b$R$^b$R$^b$, S(O)R$^b$, SO₂R$^b$, C(O)R$^b$, C(O)NR$^a$R$^a$, NR$^a$C(O)R$^b$, C(O)OR$^a$, OC(O)R$^b$, NR$^a$SO₂R$^b$, SO₂NR$^a$R$^a$, NR$^a$C(O)OR$^b$, OC(O)NR$^a$R$^a$ or NR$^a$C(O)NR$^a$R$^a$.

17. A compound according to claim 1 in which:
R¹ is selected from methyl, ethyl, isopropyl, n-butyl, tert-butyl, 2-methoxyethyl, 6-aminopyridin-3-ylmethyl, 6-difluoromethoxyphenyl or 6-difluoromethoxybenzyl;
R² is selected from phenyl, 3-chlorophenyl, 4-chlorophenyl or 4-trifluoromethylphenyl; and
R³ is selected from 4-methoxyphenyl, 4-hydroxyphenyl, 4-isopropoxyphenyl, 4-difluoromethoxyphenyl, 4-trifluoromethoxyphenyl, 4-fluorophenyl, 4-hydroxymethylphenyl, 1-benzyloxyphenyl, 4-cyclohexyloxyphenyl, 4-morpholin-4-ylphenyl, 4-piperidin-1-ylphenyl, 4-pyrrolidin-1-ylphenyl, 4-azepan-1-ylphenyl, 4-benzylpiperazin-1-ylphenyl, 4-(tertbutoxycarbonylamino)phenyl, 4-(N-acetylsulfonamide)phenyl, 2-dimethylaminocarbonyl-1-benzofuran-5-yl, 2-acetyl-1-benzofuran-5-yl, 2-tertbutoxycarbonyl-1-benzofuran-5-yl, 2-carboxy-1-benzofuran-5-yl, 1-benzofuran-5-yl, 2-ethoxycarbonyl-3-methyl-1-benzothiophene-5-yl, 1H-indol-5-yl, 6-morpholin-4-ylpyridin-3-yl, 6-methoxypyridin-3-yl, 5-cyclohexyl-2-methoxyphenyl, 3-chloro-4-morpholin-4-ylphenyl, 2,5-diethoxy-4-morpholin-4-ylphenyl, 2-acetyl-1,2,3,4-tetrahydroisoquinolin-6-yl, 2-methylaminocarbonyl-3,4-dihydroisoquinoline-2(1H)-6-yl, 1,2,3,4-tetrahydroisoquinolin-6-yl, 2-tertbutoxycarbonyl-3,4-dihydroisoquinoline-2(1H)-6-yl, 5,6,7,8-tetrahydronaphtalen-1-yl, 2-thioxo-2,3-dihydro-1,3-benzothiazol-6-yl, 1H-isoindole-1,3(2H)-dione-5-yl, 1H-benzimidazol-2-yl, 1H-1,2,4-triazol-3-yl, 3-morpholin-4-yl-1H-1,2,4-triazol-5-yl or 5-methyl-1-phenyl-pyrazol-3-yl.

18. A compound selected from one or more of the following:
2-tert-butyl-4-[(4-morpholin-4-ylphenyl)amino]-5-phenylisothiazol-3(2H)-one 1,1-dioxide
2-tert-butyl-4-[(4-methoxyphenyl)amino]-5-phenyl-isothiazol-3(2H)-one 1,1-dioxide
2-tert-butyl-5-phenyl-4-[(4-piperidin-1-ylphenyl)amino]isothiazol-3(2H)-one 1,1-dioxide
2-tert-butyl-4-[(4-isopropoxyphenyl)amino]-5-phenyl-isothiazol-3(2H)-one 1,1-dioxide
2-tert-butyl-5-phenyl-4-[(4-pyrrolidin-1-ylphenyl)amino]isothiazol-3(2H)-one 1,1-dioxide
tert-butyl {4-[(2-tert-butyl-1,1-dioxido-3-oxo-5-phenyl-2,3-dihydroisothiazol-4-yl)amino]phenyl}carbamate
4-[(4-isopropoxyphenyl)amino]-2-isopropyl-5-phenyl-isothiazol-3(2H)-one 1,1-dioxide
2-isopropyl-5-phenyl-4-[(4-piperidin-1-ylphenyl)amino]isothiazol-3(2H)-one 1,1-dioxide
4-[(4-azepan-1-ylphenyl)amino]-2-tert-butyl-5-phenyl-isothiazol-3(2H)-one 1,1-dioxide
2-isopropyl-4-[(4-morpholin-4-ylphenyl)amino]-5-phenylisothiazol-3(2H)-one 1,1-dioxide
2-butyl-4-[(4-methoxyphenyl)amino]-5-phenylisothiazol-3(2H)-one 1,1-dioxide
4-[(2-acetyl-1-benzofuran-5-yl)amino]-2-butyl-5-phenyl-isothiazol-3(2H)-one 1,1-dioxide
2-tert-butyl-4-[(6-morpholin-4-ylpyridin-3-yl)amino]-5-phenylisothiazol-3(2H)-one 1,1-dioxide
2-butyl-4-{[4-(difluoromethoxy)phenyl]amino}-5-phenylisothiazol-3(2H)-one 1,1-dioxide
2-butyl-4-[(4-morpholin-4-ylphenyl)amino]-5-phenyl-isothiazol-3(2H)-one 1,1-dioxide
tert-butyl 6-[(2-butyl-1,1-dioxido-3-oxo-5-phenyl-2,3-dihydroisothiazol-4-yl)amino]-3,4-dihydroisoquinoline-2(1H)-carboxylate
2-butyl-4-[(3-chloro-4-morpholin-4-ylphenyl)amino]-5-phenylisothiazol-3(2H)-one 1,1-dioxide
2-butyl-5-(3-chlorophenyl)-4-[(4-morpholin-4-ylphenyl)amino]isothiazol-3(2H)-one 1,1-dioxide
2-ethyl-4-[(4-morpholin-4-ylphenyl)amino]-5-phenyl-isothiazol-3(2H)-one 1,1-dioxide
4-[(2-acetyl-1,2,3,4-tetrahydroisoquinolin-6-yl)amino]-2-butyl-5-phenylisothiazol-3(2H)-one 1,1-dioxide
2-butyl-4-[(4-hydroxyphenyl)amino]-5-phenylisothiazol-3(2H)-one 1,1-dioxide
2-butyl-4-(1H-indol-5-ylamino)-5-phenylisothiazol-3(2H)-one 1,1-dioxide
5-[(2-butyl-1,1-dioxido-3-oxo-5-phenyl-2,3-dihydroisothiazol-4-yl)amino]-N,N-dimethyl-1-benzofuran-2-carboxamide
2-[4-(difluoromethoxy)benzyl]-4-[(4-morpholin-4-ylphenyl)amino]-5-phenylisothiazol-3(2H)-one 1,1-dioxide
2-butyl-5-(3-chlorophenyl)-4-{[4-(difluoromethoxy)phenyl]amino}isothiazol-3(2H)-one 1,1-dioxide
2-butyl-5-phenyl-4-{[4-(trifluoromethoxy)phenyl]amino}isothiazol-3(2H)-one 1,1-dioxide
2-butyl-4-{[4-(hydroxymethyl)phenyl]amino}-5-phenyl-isothiazol-3(2H)-one 1,1-dioxide
4-{[4-(benzyloxy)phenyl]amino}-2-butyl-5-phenyl-isothiazol-3(2H)-one 1,1-dioxide
4-{[4-(4-benzylpiperazin-1-yl)phenyl]amino}-2-butyl-5-phenylisothiazol-3(2H)-one 1,1-dioxide
2-[4-(difluoromethoxy)benzyl]-4-[(4-methoxyphenyl)amino]-5-phenylisothiazol-3(2H)-one 1,1-dioxide
4-(1-benzofuran-5-ylamino)-2-butyl-5-phenylisothiazol-3(2H)-one 1,1-dioxide
2-butyl-5-(4-chlorophenyl)-4-{[4-(difluoromethoxy)phenyl]amino}isothiazol-3(2H)-one 1,1-dioxide
2-butyl-5-phenyl-4-(1H-1,2,4-triazol-3-ylamino)isothiazol-3(2H)-one 1,1-dioxide
2-butyl-4-[(5-methyl-1-phenyl-1H-pyrazol-3-yl)amino]-5-phenylisothiazol-3(2H)-one 1,1-dioxide
2-butyl-4-[(6-methoxypyridin-3-yl)amino]-5-phenyl-isothiazol-3(2H)-one 1,1-dioxide
4-[(2-acetyl-1-benzofuran-5-yl)amino]-2-(2-methoxyethyl)-5-phenylisothiazol-3(2H)-one 1,1-dioxide
2-[4-(difluoromethoxy)benzyl]-4-{[4-(difluoromethoxy)phenyl]amino}-5-phenylisothiazol-3(2H)-one 1,1-dioxide
2-butyl-5-phenyl-4-[(2-thioxo-2,3-dihydro-1,3-benzothiazol-6-yl)amino]isothiazol-3(2H)-one 1,1-dioxide
2-methyl-4-[(4-morpholin-4-ylphenyl)amino]-5-phenyl-isothiazol-3(2H)-one 1,1-dioxide
4-[(4-methoxyphenyl)amino]-2-methyl-5-phenylisothiazol-3(2H)-one 1,1-dioxide 4-[(4-cyclohexylphenyl)amino]-2-(2-methoxyethyl)-5-phenylisothiazol-3(2H)-one 1,1-dioxide
4-[(2-acetyl-1-benzofuran-5-yl)amino]-2-methyl-5-phenylisothiazol-3(2H)-one 1,1-dioxide
2-(2-methoxyethyl)-5-phenyl-4-(5,6,7,8-tetrahydronaphthalen-1-ylamino)isothiazol-3(2H)-one 1,1-dioxide
4-(1H-indol-5-ylamino)-2-(2-methoxyethyl)-5-phenylisothiazol-3(2H)-one 1,1-dioxide
4-[(4-fluorophenyl)amino]-2-methyl-5-phenylisothiazol-3(2H)-one 1,1-dioxide
2-[(6-aminopyridin-3-yl)methyl]-4-[(4-morpholin-4-ylphenyl)amino]-5-phenylisothiazol-3(2H)-one 1,1-dioxide
N-({4-[(2-butyl-1,1-dioxido-3-oxo-5-phenyl-2,3-dihydroisothiazol-4-yl)amino]phenyl}sulfonyl)acetamide
ethyl 5-[(2-butyl-1,1-dioxido-3-oxo-5-phenyl-2,3-dihydroisothiazol-4-yl)amino]-3-methyl-1-benzothiophene-2-carboxylate
5-[(2-butyl-1,1-dioxido-3-oxo-5-phenyl-2,3-dihydroisothiazol-4-yl)amino]-1-benzofuran-2-carboxylic acid
tert-butyl 5-[(2-butyl-1,1-dioxido-3-oxo-5-phenyl-2,3-dihydroisothiazol-4-yl)amino]-1-benzofuran-2-carboxylate
4-[(2-acetyl-1-benzofuran-5-yl)amino]-2-ethyl-5-[4-(trifluoromethyl)phenyl]isothiazol-3(2H)-one 1,1-dioxide
2-(2-methoxyethyl)-4-[(3-morpholin-4-yl-1H-1,2,4-triazol-5-yl)amino]-5-phenylisothiazol-3(2H)-one 1,1-dioxide
ethyl 5-{[2-(2-methoxyethyl)-1,1-dioxido-3-oxo-5-phenyl-2,3-dihydroisothiazol-4-yl]amino}-3-methyl-1-benzothiophene-2-carboxylate
4-[(5-cyclohexyl-2-methoxyphenyl)amino]-2-(2-methoxyethyl)-5-phenylisothiazol-3(2H)-one 1,1-dioxide
4-[(4-hydroxyphenyl)amino]-2-(2-methoxyethyl)-5-phenylisothiazol-3(2H)-one 1,1-dioxide
4-(1H-benzimidazol-2-ylamino)-2-butyl-5-phenylisothiazol-3(2H)-one 1,1-dioxide
2-[(6-aminopyridin-3-yl)methyl]-4-{[4-(difluoromethoxy)phenyl]amino}-5-phenylisothiazol-3(2H)-one 1,1-dioxide
2-methyl-4-[(6-morpholin-4-ylpyridin-3-yl)amino]-5-phenylisothiazol-3(2H)-one 1,1-dioxide
2-butyl-5-phenyl-4-(1,2,3,4-tetrahydroisoquinolin-6-ylamino)isothiazol-3(2H)-one 1,1-dioxide
5-[(2-butyl-1,1-dioxido-3-oxo-5-phenyl-2,3-dihydroisothiazol-4-yl)amino]-1H-isoindole-1,3(2H)-dione
2-butyl-4-[(2,5-diethoxy-4-morpholin-4-ylphenyl)amino]-5-phenylisothiazol-3(2H)-one 1,1-dioxide
2-(2-methoxyethyl)-4-[(4-morpholin-4-ylphenyl)amino]-5-phenylisothiazol-3(2H)-one 1,1-dioxide
4-{[4-(difluoromethoxy)phenyl]amino}-2-(2-methoxyethyl)-5-phenylisothiazol-3(2H)-one 1,1-dioxide
2-ethyl-4-[(4-morpholin-4-ylphenyl)amino]-5-[4-(trifluoromethyl)phenyl]isothiazol-3(2H)-one 1,1-dioxide
6-[(2-butyl-1,1-dioxido-3-oxo-5-phenyl-2,3-dihydroisothiazol-4-yl)amino]-N-methyl-3,4-dihydroisoquinoline-2(1H)-carboxamide
4-{[4-(difluoromethoxy)phenyl]amino}-2-methyl-5-phenylisothiazol-3(2H)-one 1,1-dioxide
4-[(2-acetyl-1-benzofuran-5-yl)amino]-2-ethyl-5-[4-(trifluoromethyl)phenyl]isothiazol-3(2H)-one 1,1-dioxide
or a pharmaceutically acceptable salt or solvate thereof, or a solvate of such a salt.

19. A process for the preparation of a compound according to claim 1, comprising reacting (a) a compound of formula (VI),

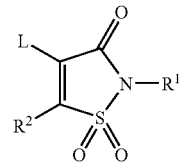

(VI)

wherein $R^1$ and $R^2$ are as defined in claim 1 and L is a leaving group, with a compound of formula (VII),

$R^3NH_2$ (VII)

wherein $R^3$ is as defined in claim 1, optionally in the presence of an inert organic solvent, or (b) a compound of formula (X),

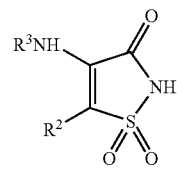

(X)

wherein $R^2$ and $R^3$ are as defined in claim 1, either with an alkylating agent, or with $R^1OH$, wherein $R^1$ is as defined in claim 1, using Mitsunobu conditions.

20. A compound of general formula (V),(VI), (IX) or (X)

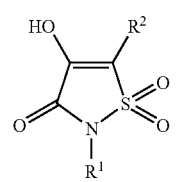

(V)

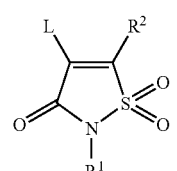

(VI)

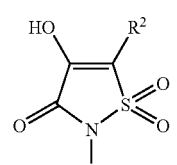

(IX)

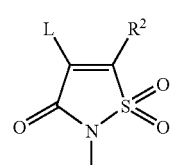

(X)

or a pharmaceutically acceptable salt thereof, wherein $R^1$ is defined as in claim 1, $R^2$ is defined as in claim 1, and L is a suitable leaving group, with the proviso that the following compounds are excluded:

- 4-hydroxy-5-phenylisothiazol-3(2H)-one 1,1-dioxide,
- 5-(4-aminophenyl)-4-hydroxy-2-methylisothiazol-3(2H)-one 1,1-dioxide,
- 4-hydroxy-2-methyl-5-(4-nitrophenyl)isothiazol-3(2H)-one 1,1-dioxide,
- 4-hydroxy-2-methyl-5-phenylisothiazol-3(2H)-one 1,1-dioxide,
- 5-(3,4-dichlorophenyl)-4-hydroxyisothiazol-3(2H)-one 1,1-dioxide,
- 2-benzyl-4-hydroxy-5-phenylisothiazol-3(2H)-one 1,1-dioxide, and
- 4-hydroxy-2-(4-methylphenyl)-5-phenylisothiazol-3(2H)-one 1,1-dioxide.

21. A pharmaceutical formulation comprising a compound according to claim 1, or a suitable pharmaceutically acceptable salt thereof, and a pharmaceutically acceptable adjuvant, diluent and/or carrier.

22. A process according to claim 19 wherein the leaving group is Cl, Br, I, p-toluensulfonate, methanesulfonate or trifluoromethanesulfonate.

23. A process according to claim 19 wherein the inert organic solvent is dimethylformamide.

24. A process according to claim 19 wherein the alkylating agent is $R^1L$, wherein $R^1$ is defined as in claim 1 and L is a leaving group.

25. A process according to claim 24 wherein L is Cl, Br, I, p-toluensulfonate, methanesulfonate or trifluoromethanesulfonate.

26. A compound according to claim 20 wherein L is Cl, Br, I, p-toluensulfonate, methanesulfonate or trifluoromethanesulfonate.

* * * * *

UNITED STATES PATENT AND TRADEMARK OFFICE
CERTIFICATE OF CORRECTION

PATENT NO. : 7,582,629 B2
APPLICATION NO. : 11/813481
DATED : September 1, 2009
INVENTOR(S) : Boström et al.

Page 1 of 1

It is certified that error appears in the above-identified patent and that said Letters Patent is hereby corrected as shown below:

Column 130, Claim 6, Line 14, "$SiR^bR^bR^bR^b$" should read --$SiR^bR^bR^b$--.

Column 132, Claim 13, Line 7, "$OR^{b1}$" should read --$OR^b$--.

Signed and Sealed this

Eighth Day of December, 2009

David J. Kappos
*Director of the United States Patent and Trademark Office*